US010925867B2

(12) United States Patent
Mulligan et al.

(10) Patent No.: US 10,925,867 B2
(45) Date of Patent: Feb. 23, 2021

(54) IMMUNOTHERAPEUTIC DOSING REGIMENS COMPRISING POMALIDOMIDE AND AN ANTI-CS1 ANTIBODY FOR TREATING CANCER

(71) Applicant: Bristol-Myers Squibb Company, Princeton, NJ (US)

(72) Inventors: Christopher Lee Mulligan, Bordentown, NJ (US); Justin Blake Bartlett, Basking Ridge, NJ (US); Michael Darron Robbins, Lebanon, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 393 days.

(21) Appl. No.: 15/738,412

(22) PCT Filed: Jun. 28, 2016

(86) PCT No.: PCT/US2016/039723
§ 371 (c)(1),
(2) Date: Dec. 20, 2017

(87) PCT Pub. No.: WO2017/003990
PCT Pub. Date: Jan. 5, 2017

(65) Prior Publication Data
US 2018/0185348 A1    Jul. 5, 2018

Related U.S. Application Data

(60) Provisional application No. 62/262,574, filed on Dec. 3, 2015, provisional application No. 62/239,965, filed on Oct. 11, 2015, provisional application No. 62/185,968, filed on Jun. 29, 2015.

(51) Int. Cl.
| | |
|---|---|
| *A61K 31/454* | (2006.01) |
| *A61K 31/573* | (2006.01) |
| *C07K 16/28* | (2006.01) |
| *A61K 39/395* | (2006.01) |
| *A61P 35/00* | (2006.01) |
| *A61K 39/00* | (2006.01) |

(52) U.S. Cl.
CPC .......... *A61K 31/454* (2013.01); *A61K 31/573* (2013.01); *A61K 39/3955* (2013.01); *A61K 39/39558* (2013.01); *A61P 35/00* (2018.01); *C07K 16/2803* (2013.01); *A61K 2039/505* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,811,097 | A | 9/1998 | Allison et al. |
| 5,855,887 | A | 1/1999 | Allison et al. |
| 5,977,318 | A | 11/1999 | Linsley et al. |
| 6,051,227 | A | 4/2000 | Allison et al. |
| 6,207,156 | B1 | 3/2001 | Kuchroo et al. |
| 6,316,471 | B1 | 11/2001 | Muller et al. |
| 6,476,052 | B1 | 11/2002 | Muller et al. |
| 6,682,736 | B1 | 7/2004 | Hanson et al. |
| 6,984,720 | B1 | 1/2006 | Korman et al. |
| 7,041,499 | B2 | 5/2006 | Mathew et al. |
| 7,109,003 | B2 | 9/2006 | Hanson et al. |
| 7,132,281 | B2 | 11/2006 | Hanson et al. |
| 7,709,610 | B2 | 5/2010 | Williams et al. |
| 8,158,653 | B2 | 4/2012 | Muller et al. |
| 8,198,262 | B2 | 6/2012 | Zeldis |
| 8,673,939 | B2 | 3/2014 | Zeldis |
| 8,735,428 | B2 | 5/2014 | Zeldis |
| 8,828,427 | B2 | 9/2014 | Tutino et al. |
| 10,034,872 | B2 | 7/2018 | Thakurta et al. |
| 2002/0039581 | A1 | 4/2002 | Carreno et al. |
| 2002/0086014 | A1 | 7/2002 | Korman et al. |
| 2005/0201994 | A1 | 9/2005 | Korman et al. |
| 2008/0124332 | A1* | 5/2008 | Afar .................... A61K 31/704 424/138.1 |
| 2016/0051530 | A1* | 2/2016 | Thakurta ............ C07K 16/2803 424/451 |

FOREIGN PATENT DOCUMENTS

| | | |
|---|---|---|
| EP | 1212422 | 6/2002 |
| WO | WO 98/42752 | 10/1998 |
| WO | WO 00/37504 | 6/2000 |
| WO | WO 2001/014424 | 3/2001 |
| WO | WO 2004/035607 | 4/2004 |
| WO | WO2004/043377 | 5/2004 |
| WO | WO 2004/100898 | 11/2004 |
| WO | WO 2005/10238 | 2/2005 |
| WO | WO 2006/121168 | 11/2006 |
| WO | WO 2008/019376 | 2/2008 |

(Continued)

OTHER PUBLICATIONS

Lacy et al. (Leukemia, 2010, 24:1934-1939) (Year: 2010).*
Hanaizi et al. (The Oncologist, 2015, 20:329-334) (Year: 2015).*
Rhee (Molecular Cancer Therapy, 2009, 8:2616-2624) (Year: 2009).*
Anderson, K. C., et al. (2007). "Clinically relevant end points and new drug approvals for myeloma." *Leukemia* 22(2): 231-239.
Badros A. et al., "A phase II study of anti PD-I antibody pembrolizumab, pomalidomide and dexamethasone in patients with relapsed/refractory multiple myeloma (RRMM)", Blood: 26:Abstract 506 (2015) http://www.bloodjournal.org/content/126/23/506.
Balasa, B. et al., "Elotuzumab enhances natural killer cell activation and myeloma cell killing through interleukin-2 and TNF-a pathways", Cancer Immunol. Immunother., 64:61-73 (2015).

(Continued)

*Primary Examiner* — Peter J Reddig
(74) *Attorney, Agent, or Firm* — Paul D. Golian

(57) ABSTRACT

The invention described herein relates to therapeutic dosing regimens and combinations thereof for use in enhancing the therapeutic efficacy of anti-CS1 antibodies in combination with one or more immunotherapeutic agents.

3 Claims, 23 Drawing Sheets

Figure 1:
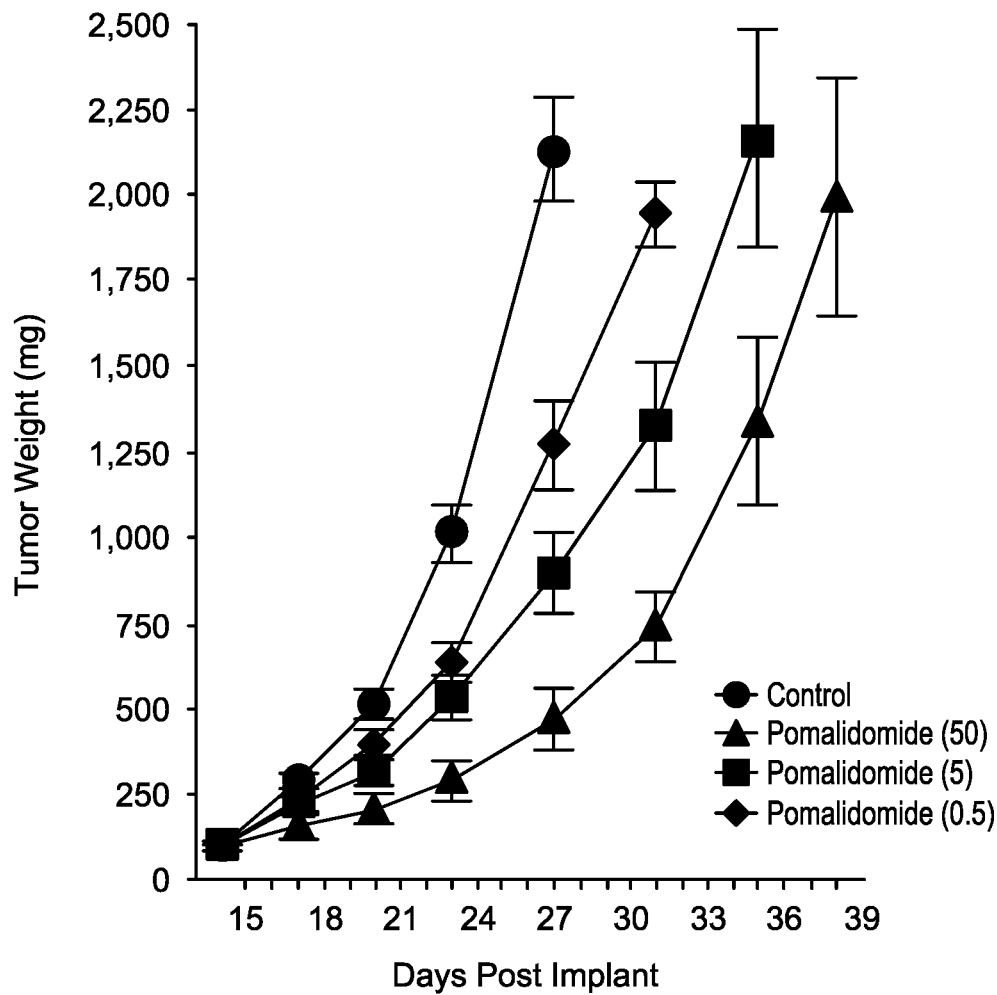

Specification includes a Sequence Listing.

(56) References Cited

FOREIGN PATENT DOCUMENTS

| WO | WO 2008/019378 | 2/2008 |
|---|---|---|
| WO | WO 2008/019379 | 2/2008 |
| WO | WO 2010/051391 | 5/2010 |
| WO | WO 2011/053321 | 5/2011 |
| WO | WO 2011/053322 | 5/2011 |
| WO | WO 2016/029004 | 2/2016 |
| WO | WO 2016/070089 | 5/2016 |

OTHER PUBLICATIONS

Bhat, R. et al., J. Leukoc. Biol., 79:417-424 (2006).
Boles et al., Immunogenetics, 52:302-307 (2001).
Bouchon et al., J. Immunol., 167:5517-5521 (2001).
Brenner et al., Blood, 111:2521-2526 (2008).
Camacho et al., J. Clin. Oncology, 22(145):Abstract No. 2505 (2004).
Cavo et al., Lancet, 376:2075-2085 (2010).
Collins et al., Cancer Immunol. Immunother., 62(12)1 841-1849(2013).
Cruz-Munoz ME, et al., Influence of CRACC, a SLAM family receptor coupled to the adaptor EAT-2, on natural killer cell 20 function. Nat Immunol. Mar. 2009; 10(3):297-305.
DeVita VT, Lawrence TS, and Rosenberg SA. Cancer: Principles and 5 Practice of Oncology 9th edition. Chapter 136; pp. 1999-1999.Wolters Kluwer/ Lippincott, Williams, and Wilkins 2011.
Dimopoulos, M.A.et al., Pomalidomide in Combination with Low-Dose Dexamethasone: Demonstrates a Significant Progression Free Survival and Overall Survival Advantage, in Relapsed/Refractory MM: A Phase 3, Multicenter, Randomized, Open-Label Study; Blood; 120: LBA-6 http://www.bloodjournal.org/content/120/21/LBA-6.
Dingli et al. Flow cytometric detection of circulating myeloma cells before transplantation in patients with multiple myeloma: a simple risk stratification system. Blood. Apr 15, 2006; 107(8): 3384-3388.
Dornan D, et al. Effect of FCGR2A and FCGR3A variants on CLL outcome. Blood. Nov. 18, 2010; 116(20):4212-22.
Durie BG, et al.; International uniform response criteria for multiple myeloma. Leukemia 2006; 20: 1467-1473.
Fischer, A. et al., Curr. Opin. Immunol., 19:348-353 (2007).
Glavey S, et al.; Dissecting the Mechanisms of Activity of SLAMF7 and the Targeting Antibody Elotuzumab in Multiple Myeloma. Blood 2014 124: Abstract 3431 http://www.bloodjournal.org/content/124/21/3431.
Gorgun et al., Lenalidomide Enhances Immune Checkpoint Blockade-Induced Immune Response in Multiple Myeloma, Clin Cancer Res.Oct. 15, 2015;21(20):4607-18.
Greenway, A. D., Impact of Elotuzumab Therapy on Circulating and Ex Vivo Activated/Expanded Autologous Natural Killer (Auto-ENK) Cell Activity. Blood, 122(21), 5389. (2013). http://www.bloodjournal.org/content/122/21/5389.
Greipp PR, et al., International Staging System for Multiple Myeloma. J Clin Oncology 2005 23:3412-3420.
Gross S. et al., "Automated Enumeration and Characterization of Circulating Multiple Myeloma Cells in Blood", Oral and Poster Abstracts, ASH. Session 651. Myeloma—Biology and Pathophysiology.
Guo H, et al. Immune cell inhibition by SLAMF7 is mediated by mechanism requiring Src kinases, CD45 and SHIP-1 defective in multiple myeloma cells. Mol Cell Biol. Jan. 2015; 35(1):41-51.
Harousseau et al., J. Clin. Oncol., 28:4621-4629 (2010).
Hatjiharissi E, et al. Increased natural killer cell expression of CD16, augmented binding and ADCC activity to rituximab among individuals expressing the FcgammaRIIIa-158 V/V and V/F polymorphism. Blood. Oct. 2007 I; 110(7):2561-2564.
Hsi, E.D. et al., Clin. Cancer Res., 14:2775-2784 (2008).
Hurwitz et al. , Proc. Natl. Head. Sci. USA, 95(17):10067-10071(1998).
Jakubowiak et al., J. Clin. Oncol., 30(16):1960-1965 (2012).
Jemal A. et al., Cancer Statistics. CA Cancer JClin 2005; 55: 10-30.
Jinushi M, et al., MHC class I chain-related protein A antibodies and shedding are associated with the progression of multiple myeloma. Proc Natl Acad Sci USA. Jan. 29, 2008; 105(4):1285-90.
Kim JR, et al. CSI (SLAMF7) inhibits production of proinflammatory cytokines by activated monocytes. Inflamm Res. Aug. 2013; 62(8):765-72.
Kristinsson et al., J. Clin. Oncol., 25:1993-1999 (2007).
Kumar et al., Blood, 111:2516-2520 (2008).
Kumar, S. and S. V. Rajkumar (2006). "Thalidomide and lenalidomide in the treatment of multiple myeloma." European Journal of Cancer 42(11): 1612-1622.
Lacy et al., ASH Abstract 4780 (2014).
Lacy et al., Blood, 118(11):2970-2975(2011).
Lacy et al., Am. J. Hematol., 85(2):95-96 (2009).
Lee, J.K. et al., J. Immunol., 179:4672-5 4678 (2007).
Lonial et al., J. Clin. Oncol., 30:1953-1959 (2012).
Lonial et al., J. Clin. Oncol., 31 (2013) (Suppl., Abstr. 8542); http://ascopubs.org/doi/abs/10.1200/jco.2013.31.15_suppl.8542.
Lonial S, et al. Elotuzumab Therapy for Relapsed or Refractory Multiple Myeloma. N Engl JMed 373:621-631 (2015).
Ludwig H, Beksac M, Blade J, et al. Current multiple myeloma treatment strategies with novel agents: a European perspective. The Oncologist. 2010; 15:6-25.
Mokyr et al., Cancer Res. , 58:5301-5304 (1998).
Murphy et al., Biochem. J., 361:431-436 (2002).
Perez-Quintero Lai, et. al. EAT-2, a SAP-like adaptor, controls NK cell activation through phospholipase Cy, Ca++, and Erk, leading to granule polarization. JExp Med. Apr. 7, 2014; 211(4):727-42.
Pratt, Guy. Histone deacetylase inhibitors in multiple myeloma. The Lancet Oncology, vol. 14, Issue 11, 1038-1039.
Raab et al., Lancet, 374:324-339 (2009).
Rajkumar et al., J. Clin. Oncol., 26:2171-2177 (2008).
Rajkumar et al., Lancet Oncol., 11:29-37 (2010).
Rajkumar SV et al.; Consensus recommendations for the uniform reporting of clinical trials: report of the International Myeloma Workshop Consensus Panel 1 Blood. May 5, 2011; 117(18):4691-5.
Rajkumar SVet al.; Phase III clinical trial of thalidomide plus dexamethasone compared with dexamethasone alone in newly diagnosed multiple myeloma: A clinical trial coordinated by the Eastern Cooperative Oncology group. JClin Oncol 2006; 24(3):431-436.
Reeder et al., Leukemia, 23:1337-1341 (2009).
Rhee, F. et al., Mol. Cancer Ther., 8(9):2616-2624 (2009).
Richardson, MD, et al. Final Results for the Phase Ib/2 Study of Elotuzumab in Combination with Lenalidomide and Dexamethasone in Patients with Relapsed/Refractory Multiple Myeloma. American Society of Hematology Abstract, 2014 http://www.bloodjournal.org/content/124/21/302.
Richardson, P. G., et al. (2005). "Bortezomib or High-Dose Dexamethasone for Relapsed Multiple Myeloma." New England Journal of Medicine 352(24): 2487-2498.
Richardson et al. , Blood, 121(11):1961-1967(2013).
Richardson et al. , N. Eng. J. Med. , 348:2609-2617 (2003).
Richardson et al., Blood (ASH Annual Meeting Abstracts), 116:986 (2010); http://www.bloodjournal.org/content/116/21/986.
Richardson et al., Blood, 116:679-686 (2010).
Richardson PG, Siegel DS, Vij R, et al. Pomalidomide alone or in combination with lowdose dexamethasone in relapsed and refractory multiple myeloma: a randomized phase 2 study. Blood, Mar. 20, 2014; 123(12):1826-32.
San Miguel J, et al., Pomalidomide plus lowdose dexamethasone versus high-dose dexamethasone alone for patients with relapsed and refractory multiple myeloma (MM-003): a randomized, open-label, phase 3 trial. Lancet Oncol. Oct. 2013; 14(11):1055-66.
San Miguel et al., ASCO Meeting Library, 164962-176, Jun. 6, 2016, https://meetinglibrary.asco.org/content/164962-176.
Sonneveld et al., Blood (ASH Annual Meeting Abstracts), 116:23 (2010); http://www.bloodjournal.org/content/116/21/40.
Tai et al., Blood, 112:1329-1337 (2008).
Tai, Y.T. et al., Blood, 113(18):4309-4318 (Apr. 30, 2009).
Tricot, G. et al., Blood, 86:4250-4252 (1995).

(56) References Cited

OTHER PUBLICATIONS

Tuscano JM, et. al. Lenalidomide plus rituximab can produce durable clinical responses in patients with relapsed or refractory, indolent non-Hodgkin lymphoma. Br JHaematol. May 2014; 165(3):375-81.
Veillette, A., Immunol. Rev., 214:22-34 (2006).
Von Lilienfeld-Toal et al. Reduced immune effector cell NKG2D expression and increased levels of soluble NKG2D ligands in multiple myeloma may not be causally linked. Cancer Immunol Immunother. Jun. 2010; 59(6):829-39.
Von Lilienfield-Toal et al., *Eur. J. Haematol.*, 81:247-252 (2008).
Weisel, K. et al., Analysis of Patients With Refractory or Relapsed and Refractory Multiple Myeloma and Renal Impairment Treated With Pomalidomide + Low-Dose Dexamethasone in the Phase 3b STRATUS Trial (MM-010), Abstract, European Hematology Association, Jun. 2015, p. 286.
Weng WK, Levy R. Two immunoglobulin G fragment C receptor polymorphisms independently predict response to rituximab in patients with follicular lymphoma. JClin Oncol. Nov. 2003 I; 21(21):3940-7.
Xie Z, et al., Plasma membrane proteomics identifies biomarkers associated with MMSET overexpression in T(4;14) multiple myeloma. Oncotarget. Jul. 2013; 4(7):1008-18.
Zonder et al., Blood, 120(3):552-559 (2012).
Kastritis et al.; Targeted Oncology, 2009, 4(1), pp. 23-36.
Dimopoulos, et al.; New England Journal of Medicine, 379: 19, pp. 1811-1822 (2018).
Mateos, et al.; British Journal of Haematology, 175, pp. 448-456 (2016).

\* cited by examiner

SEQUENCE LISTING

<160> NUMBER OF SEQ ID NOS: 5

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly

```
                1               5                  10                 15
Asp Arg Val Thr Ile Thr Cys Lys Ala Ser Gln Asp Val Gly Ile Ala
                    20                  25                 30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                    85                  90                  95

Thr Phe Gly Gln Gly Thr Lys Val Glu Ile Lys
                100                 105
```

<210> SEQ ID NO 2
<211> LENGTH: 119
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
                100                 105                 110

Thr Leu Val Thr Val Ser Ser
        115
```

<210> SEQ ID NO 3
<211> LENGTH: 9
<212> TYPE: PRT
<213> ORGANISM: Homo sapiens

<400> SEQUENCE: 3

```
Ile Met Asp Gln Val Pro Phe Ser Val
1               5
```

<210> SEQ ID NO 4
<211> LENGTH: 9
<212> TYPE: PRT
<213> ORGANISM: Homo sapiens

<400> SEQUENCE: 4

```
Tyr Leu Glu Pro Gly Pro Val Thr Val
1               5
```

<210> SEQ ID NO 5
<211> LENGTH: 334
<212> TYPE: PRT
<213> ORGANISM: Homo sapiens

<400> SEQUENCE: 5

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val
                325                 330

IMMUNOTHERAPEUTIC DOSING REGIMENS COMPRISING POMALIDOMIDE AND AN ANTI-CS1 ANTIBODY FOR TREATING CANCER

This application claims benefit to provisional application U.S. Ser. No. 62/185,968 filed Jun. 29, 2015; to provisional application U.S. Ser. No. 62/239,965 filed Oct. 11, 2015, and to provisional application U.S. Ser. No. 62/262,574 filed Dec. 3, 2015 under 35 U.S.C. § 119(e). The entire teachings of the referenced application are incorporated herein by reference.

SEQUENCE LISTING

The specification further incorporates by reference the Sequence Listing submitted via EFS on Dec. 20, 2017. The Sequence Listing text file, identified as 20171220_ST25_12585USPCT.txt, is 5494 bytes and was created on Dec. 20, 2017.

FIELD OF THE INVENTION

The invention described herein relates to therapeutic dosing regimens and combinations thereof for use in enhancing the therapeutic efficacy of anti-CS1 antibodies in combination with one or more immunotherapeutic agents.

BACKGROUND OF THE INVENTION

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Cancer can occur in any tissue or organ of the body. Plasma cell neoplasms, including multiple myeloma, "Solitary" myeloma of bone, extramedullary plasmacytoma, plasma cell leukemia, macroglobulinemia (including Waldenstrom's macroglobulinemia), heavy-chain disease, primary amyloidosis, monoclonal gammopathy of unknown significance (MGUS) are associated with increased expression of immunoglobulins. Chronic lymphocytic leukemia (CLL), a non-plasma cell neoplasm, is also associated with high levels of immunoglobulin expression.

Increased expression of immunoglobulin can also be seen in malignant diseases. Like autoimmune disorders, the etiology of cancer is similarly multi-factorial in origin. Cancer, which is the second leading cause of death in the United States, has been linked to mutations in DNA that cause unrestrained growth of cells. Genetic predisposition plays a large role in the development of many cancers, combined with environmental factors, such as smoking and chemical mutagenesis.

Myelomas are tumors of plasma cells derived from a single clone, which typically originates in secondary lymphoid tissue and then migrates into and resides in bone marrow tissue. Myelomas commonly affect the bone marrow and adjacent bone structures, with primary symptoms of bone pain and pathological fractures or lesions (osteolytic bone lesions), abnormal bleeding, anemia and increased susceptibility to infections. Advanced stages of the disease include renal failure, skeletal deformities, compaction of the spinal cord, and hypercalcemia. Myeloma affects bone cells by inducing osteoclast resorption of bone, hence decimating bone structure and increasing calcium concentration in plasma. The etiology of myelomas is currently unknown. Linkage to radiation damage, mutations in oncogenes, familial causes and abnormal IL6 expression have been postulated.

Multiple myelomas are plasma cell tumors with multiple origins. Multiple myelomas account for nearly 10% of all plasma cell malignancies, and are the most common bone tumor cancer in adults, with an annual incident rate of 3 to 4 cases per 100,000 people with a median age at diagnosis of between 63 and 70 years. In the United States, multiple myelomas are the second most common hematologic malignancy after Non-Hodgkin's Lymphoma, with approximately 50,000 cases in the United States alone, and approximately 13,500 new reported cases every year. In Europe, the incidence of multiple myelomas is 6 cases per 100,000 people per year. The prognosis outlook for patients diagnosed with multiple myelomas is grim, with only several months to a year for patients with advanced forms of the disease.

Traditional treatment regions for myeloma and multiple myelomas (henceforth referred to as "myeloma") consist of chemotherapy, radiation therapy, and surgery. In addition, bone marrow transplantation is recommended for patients who are otherwise in good health. The cure rate for patients approaches 30%, and is the only method known that can cure myelomas. However, for individuals who are older or cannot tolerate bone marrow transplantation procedures, chemotherapy is most appropriate.

Recently, important advances in multiple myeloma therapies such as the introduction of autologous stem cell transplantation (ASCT) and the availability of thalidomide, lenalidomide (immunomodulatory drugs or IMiDs) and bortezomib have changed the management of these patients and have allowed an increase in overall survival (OS) (Kristinsson et al., *J Clin. Oncol.*, 25:1993-1999 (2007); Brenner et al., *Blood*, 111:2521-2526 (2008); and Kumar et al., *Blood*, 111:2516-2520 (2008)). Patients younger than 60 years have a 10-year survival probability of ~30% (Raab et al., *Lancet*, 374:324-339 (2009)). Thalidomide (Rajkumar et al., *J. Clin. Oncol.*, 26:2171-2177 (2008)), lenalidomide (Rajkumar et al., *Lancet Oncol.*, 11:29-37 (2010)); or bortezomib (Harousseau et al., *J. Clin. Oncol.*, 28:4621-4629 (2010)), in combination with dexamethasone as part of an induction therapy regimen before ASCT has led to rates of nearly CR of 8%, 15% and 16%, respectively; whereas three-drug induction schedules of bortezomib-dexamethasone plus doxorubicin (Sonneveld et al., *Blood* (ASH Annual Meeting Abstracts), 116:23 (2010)), cyclophosphamide (Reeder et al., *Leukemia*, 23:1337-1341 (2009)), thalidomide (Cavo et al., *Lancet*, 376:2075-2085 (2010)); or lenalidomide (Richardson et al., *Blood*, 116:679-686 (2010)), permits achievement rates of nearly CR of 7%, 39%, 32% and 57%, respectively. However, despite these advances, almost all multiple myeloma patients relapse.

The appearance of abnormal antibodies, known as M-protein, is a diagnostic indicator of multiple myeloma. The increased production of M-protein has been linked to hyperviscosity syndrome in multiple myelomas, causing debilitating side effects, including fatigue, headaches, shortness of breath, mental confusion, chest pain, kidney damage and failure, vision problems and Raynaud's phenomenon (poor blood circulation, particularly fingers, toes, nose and ears). Cryoglobulinemia occurs when M-protein in the blood forms particles under cold conditions. These particles can block small blood vessels and cause pain and numbness in the toes, fingers, and other extremities during cold weather. Prognostic indicators, such as chromosomal deletions, elevated levels of beta-2 microglobulin, serum creatinine levels and IgA isotyping have also been studied. Tricot, G. et al., "Poor Prognosis in Multiple Myeloma", *Blood*, 86:4250-4252 (1995).

Pomalidomide, is a potent, second-generation IMiD. It has shown activity in multiple myeloma, while achieving a better toxicity profile relative to lenalidomide and thalidomide (Lacy et al., *Am. J. Hematol.*, 85(2):95-96 (2009)). In Ph II clinical trials, the overall response rate of 63% was observed with a median progression free survival of 11.6 months in patients who were administered pomalidomide with 33% of those patients achieving a very good response rate (VGPR) or complete response (CR) (Lacy et al. (2009)). This compares to a 40%-50% response rate for lenalidomide treated patients (von Lilienfield-Toal et al., *Eur. J. Haematol.*, 81:247-252 (2008)), and 38% response rate for patients treated with bortezomib (Richardson et al., *N Eng. J. Med.*, 348:2609-2617 (2003)). POMALYST® was approved by the United States FDA in 2013 for the treatment of patients with advanced multiple myeloma whose disease progressed after being treated with other cancer drug.

Elotuzumab is a humanized monoclonal IgG1 antibody directed against CS-1, a cell surface glycoprotein, which is highly and uniformly expressed in multiple myeloma. Elotuzumab induces significant antibody-dependent cellular cytotoxicity (ADCC) against primary multiple myeloma cells in the presence of peripheral lymphocytes (Tai et al., *Blood*, 112:1329-1337 (2008)). Results of three studies that evaluated the safety and efficacy of this drug administered alone (Zonder et al., *Blood*, 120(3):552-559 (2012)), in combination with bortezomib (Jakubowiak et al., *J. Clin. Oncol.*, 30(16):1960-1965 (Jun. 1, 2012)), or lenalidomide and low-dose dexamethasone (Lonial et al., *J. Clin. Oncol.*, 30:1953-1959 (2012); and Richardson et al., *Blood* (ASH Annual Meeting Abstracts), 116:986 (2010) for the treatment of patients with relapsed or refractory multiple myeloma, have been reported. All three combinations showed a manageable safety profile and encouraging activity. For example, a Phase I/II study evaluating the safety and efficacy of elotuzumab in combination with lenalidomide and low-dose dexamethasone for the treatment of relapsed or refractory multiple myeloma demonstrated a 33 month PFS as well as a 92% response rate for patients receiving the 10 mg/kg dose (Lonial et al., *J. Clin. Oncol.*, 31(Suppl.), Abstr. 8542) (2013)). Phase III clinical trials of lenalidomide/dexamethasone with or without elotuzumab in previously untreated multiple myeloma patients is ongoing, while another phase III trial designed to evaluate this same combination in the first line setting is also ongoing.

Elotuzumab demonstrates a dual mechanism that includes direct NK cell activation and NK cell-mediated ADCC. Regarding NK cell activation activity, elotuzumab has been shown to activate NK cells by up-regulation of CD69 and granzyme B expression in a manner independent of the Fc portion of the antibody (see Collins et al., *Cancer Immunol. Immunother.*, 62(12):1841-1849 (2013)). Thus is further supported by Elotuzumabs ability to modulate NK cell function and killing of human MM cell lines in the absence of CD16 binding (a critical component for ADCC). Additionally elotuzumab can activate (induction of IFNγ) primary NK cells and a NK cell line deficient in CD16 supporting the role elotuzumab plays in the direct activation of NK cells through SLAMF7 in the presence of EAT-2 and independent of CD16-mediated ADCC. Thus, this is consistent with the role of SLAMF7 as a co-activating receptor on NK cells (Cruz-Munoz et al., *Nat. Immunol.*, 10(3):297-305 (2009)). Lastly, the mechanism of action of elotuzumab shows that NK cell-mediated ADCC (antibody dependent cellular cytotoxicity) is a major component to the activity observed in vitro (Tai et al., *Blood*, 112:1329-1337 (2008); and Hsi et al., *Clin. Cancer Res.*, 14(9):2775-2784 (2008)).

The present inventors have discovered, for the first time, that administration of a therapeutically effective amount of pomalidomide with a therapeutically effective amount of an anti-CS1 antibody and dexamethasone, results in synergistic regressions of multiple myeloma cells and tumors, thus establishing this combination as a potential treatment option for multiple myeloma patients.

SUMMARY OF THE INVENTION

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said cancer is selected from the group consisting of: myeloma, multiple myeloma, relapsed multiple myeloma, refractory multiple myeloma, and smoldering multiple myeloma, among others.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said cancer is selected from the group consisting of: myeloma, multiple myeloma, relapsed multiple myeloma, refractory multiple myeloma, and smoldering multiple myeloma, wherein said anti-CS1 antibody is elotuzumab.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose between about 10 mg/kg to 20 mg/kg.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle for cycles 1 and 2, and then administered at a dose of 10 mg/kg on days 1 and 15 every 28 days per cycle for cycles 3 and beyond.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose between about 10 mg/kg to 20 mg/kg, and wherein pomalidomide is administered at a dose between about 1 mg to 4 mg.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg, and wherein pomalidomide is administered at a dose of 4 mg.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, and wherein pomalidomide is administered at a dose of 4 mg daily.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, and wherein pomalidomide is administered at a dose of 4 mg daily for 21 days over a 28-day cycle.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle, and wherein pomalidomide is administered at a dose of 4 mg daily for 21 days over a 28-day cycle.

The present invention provides a method for treating a patient with multiple myeloma comprising the administration of a combination therapeutic regiment comprising: (i) a therapeutically effective amount of an of an anti-CS1 antibody; and (ii) a therapeutically effective amount of pomalidomide, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle for cycles 1 and 2, and then administered at a dose of 10 mg/kg on days 1 and 15 every 28 days per cycle for cycles 3 and beyond, and wherein pomalidomide is administered at a dose of 4 mg daily for 21 days over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said cancer is selected from the group consisting of: myeloma, multiple myeloma, relapsed multiple myeloma, refractory multiple myeloma, and smoldering multiple myeloma, among others.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said cancer is selected from the group consisting of: myeloma, multiple myeloma, relapsed multiple myeloma, refractory multiple myeloma, and smoldering multiple myeloma, wherein said anti-CS1 antibody is elotuzumab.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose between about 10 mg/kg to 20 mg/kg, wherein pomalidomide is administered at a dose between about 1 mg to 4 mg, and wherein dexamethasone is administered at a dose between about 28 mg to 40 mg for oral administration, or at a dose of about 8 mg for IV administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg, wherein pomalidomide is administered at a dose of 4 mg, and wherein dexamethasone is administered at a dose of 28 mg for oral administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg, wherein pomalidomide is administered at a dose of 4 mg, and wherein dexamethasone is administered at a dose of 40 mg for oral administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg, wherein pomalidomide is administered at a dose of 4 mg, and wherein dexamethasone is administered at a dose of 8 mg for IV administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily, and wherein dexamethasone is administered at a dose of 28 mg daily for oral administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily, and wherein dexamethasone is administered at a dose of 40 mg daily for oral administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily, and wherein dexamethasone is administered at a dose of 8 mg weekly for IV administration.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily for 21 days over a 28-day cycle, and wherein dexamethasone is administered at a dose of 28 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily for 21 days over a 28-day cycle, and wherein dexamethasone is administered at a dose of 40 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg every three weeks, wherein pomalidomide is administered at a dose of 4 mg daily for 21 days over a 28-day cycle, and wherein dexamethasone is administered at a dose of 8 mg weekly for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle, wherein pomalidomide is administered at a dose of 4 mg daily for 21 days over a 28-day cycle, and wherein dexamethasone is administered at a dose of 28 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle, wherein pomalidomide is administered at a dose of 4 mg daily for 21 days over a 28-day cycle, and wherein dexamethasone is administered at a dose of 40 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle, wherein pomalidomide is administered at a dose of 4 mg daily for 21 days over a 28-day cycle, and wherein dexamethasone is administered at a dose of 8 mg weekly for IV administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle for cycles 1 and 2, and then administered at a dose of 10 mg/kg on days 1 and 15 every 28 days per cycle for cycles 3 and beyond, wherein pomalidomide is administered at a dose of 4 mg daily for 21 days over a 28-day cycle, and wherein dexamethasone is administered at a dose of 28 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle for cycles 1 and 2, and then administered at a dose of 10 mg/kg on days 1 and 15 every 28 days per cycle for cycles 3 and beyond, wherein pomalidomide is administered at a dose of 4 mg daily for 21 days over a 28-day cycle, and wherein dexamethasone is administered at a dose of 40 mg daily for oral administration over a 28-day cycle.

The present invention provides a method for treating a patient with multiple myeloma comprising the administration of a combination therapeutic regiment comprising: (i) a therapeutically effective amount of an of an anti-CS1 antibody; (ii) a therapeutically effective amount of pomalidomide; and (iii) a therapeutically acceptable mount of dexamethasone, wherein said combination results in the synergistic reduction in tumor burden, tumor regression, tumor development, reduction in M-protein levels, plasma cells, and/or regression of said cancer, wherein said anti-CS1 antibody is elotuzumab and is administered at a dose of 10 mg/kg on days 1, 8, 15, and 22 every 28 days per cycle for cycles 1 and 2, and then administered at a dose of 10 mg/kg on days 1 and 15 every 28 days per cycle for cycles 3 and beyond, wherein pomalidomide is administered at a dose of 4 mg daily for 21 days over a 28-day cycle, and wherein dexamethasone is administered at a dose of 8 mg weekly for oral administration over a 28-day cycle.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and (b) pomalidomide.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and (b) pomalidomide;

wherein the anti-CS1 antibody is administered at a dose between about 10 mg/kg to 20 mg/kg; and wherein pomalidomide is administered at a dose between about 1 mg to 4 mg.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and (b) pomalidomide;

wherein the anti-CS1 antibody is administered at a dose of about 10 mg/kg; and wherein pomalidomide is administered at a dose of about 4 mg.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and (b) pomalidomide;

wherein the anti-CS1 antibody is administered at a dose of about 10 mg/kg once every 21 days for each 28-day cycle; and wherein pomalidomide is administered at a dose of about 4 mg daily for 21 days for each 28-day cycle.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and (b) pomalidomide;

wherein the anti-CS1 antibody is administered at a dose of about 10 mg/kg on days 1, 8, 15, and 21 for each 28-day cycle; and wherein pomalidomide is administered at a dose of about 4 mg daily for 21 days for each 28-day cycle.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;

(b) pomalidomide; and (c) dexamethasone.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;

(b) pomalidomide; and (c) dexamethasone;

wherein the anti-CS1 antibody is administered at a dose between about 10 mg/kg to 20 mg/kg; and wherein pomalidomide is administered at a dose between about 1 mg to 4 mg; and wherein dexamethasone is administered at a dose between 28 mg to 40 mg for oral administration, or at a dose of about 8 mg for IV administration.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;

(b) pomalidomide; and (c) dexamethasone;

wherein the anti-CS1 antibody is administered at a dose of about 10 mg/kg; and wherein pomalidomide is administered at an oral dose of about 4 mg; and wherein dexamethasone is administered at an oral dose of about 28 mg.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;

(b) pomalidomide;

(c) dexamethasone; and wherein the anti-CS1 antibody is administered at a dose of about 10 mg/kg; and wherein pomalidomide is administered at an oral dose of about 4 mg; and wherein dexamethasone is administered at an oral dose of about 28 mg.

In another aspect, methods of treating multiple myeloma in a human patient are provided, the methods comprising administering to the patient, an effective amount of:

(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg; and
wherein pomalidomide is administered at an oral dose of about 4 mg; and
wherein dexamethasone is administered at a dose of about 8 mg via IV.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg once every 21 days for each 28-day cycle; and
wherein pomalidomide is administered at an oral dose of about 4 mg daily for 21 days for each 28-day cycle; and
wherein dexamethasone is administered at an oral dose of about 28 mg daily for each 28-day cycle.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg once every 21 days for each 28-day cycle; and
wherein pomalidomide is administered at an oral dose of about 4 mg daily for 21 days for each 28-day cycle; and
wherein dexamethasone is administered at an oral dose of about 40 mg daily for each 28-day cycle.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg once every 21 days for each 28-day cycle; and
wherein pomalidomide is administered at an oral dose of about 4 mg daily for 21 days for each 28-day cycle; and
wherein dexamethasone is administered at an IV dose of about 8 mg weekly for each 28-day cycle.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg on days 1, 8, 15, and 21 for each 28-day cycle; and
wherein pomalidomide is administered at a dose of about 4 mg daily for 21 days for each 28-day cycle; and
wherein dexamethasone is administered at an oral dose of about 28 mg daily for each 28-day cycle.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg on days 1, 8, 15, and 21 for each 28-day cycle; and
wherein pomalidomide is administered at a dose of about 4 mg daily for 21 days for each 28-day cycle; and
wherein dexamethasone is administered at an oral dose of about 40 mg daily for each 28-day cycle.

In another aspect, methods of treating multiple myeloma in a human patient are provided, the methods comprising administering to the patient, an effective amount of:
  (a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
  (b) pomalidomide; and
  (c) dexamethasone;
wherein the anti-CS1 antibody is administered at a dose of about 10 mg/kg on days 1, 8, 15, and 21 for each 28-day cycle; and
wherein pomalidomide is administered at a dose of about 4 mg daily for 21 days for each 28-day cycle; and
wherein dexamethasone is administered at an IV oral dose of about 8 mg weekly for each 28-day cycle.

In certain embodiments, each dose of pomalidomide is administered at about 1, 2, 3, or 4 mg orally. In a preferred embodiment, each dose of the anti-CS1 antibody is administered at 4 mg orally. In other embodiments, each dose of the anti-CS1 antibody is administered at about 0.1, 0.3, 1, 3, 6, 10 or 20 mg/kg body weight. In a preferred embodiment, each dose of the anti-CS1 antibody is administered at 10 mg/kg. In other embodiments, each dose of dexamethasone is administered orally at about 28 mg or 40 mg, or 8 mg via IV. In a preferred embodiment, each dose of dexamethasone is administered at 28 mg/kg orally or 8 mg via IV.

In one embodiment, pomalidomide and the anti-CS1 antibody are administered at the following doses:
  (a) 1 mg pomalidomide and 10 mg/kg of anti-CS1 antibody;
  (b) 2 mg pomalidomide and 10 mg/kg of anti-CS1 antibody;
  (c) 3 mg pomalidomide and 10 mg/kg of anti-CS1 antibody; or (d) 4 mg pomalidomide and 10 mg/kg of anti-CS1 antibody.

In one embodiment, pomalidomide, the anti-CS1 antibody, and dexamethasone are administered at the following doses:
(a) 1 mg pomalidomide, 10 mg/kg of anti-CS1 antibody, and 28 mg dexamethasone;
(b) 2 mg pomalidomide, 10 mg/kg of anti-CS1 antibody, and 28 mg dexamethasone;
(c) 3 mg pomalidomide, 10 mg/kg of anti-CS1 antibody, and 28 mg dexamethasone; or
(d) 4 mg pomalidomide, 10 mg/kg of anti-CS1 antibody, and 28 mg dexamethasone.

In one embodiment, pomalidomide, the anti-CS1 antibody, and dexamethasone are administered at the following doses:
(a) 1 mg pomalidomide, 10 mg/kg of anti-CS1 antibody, and 40 mg dexamethasone;
(b) 2 mg pomalidomide, 10 mg/kg of anti-CS1 antibody, and 40 mg dexamethasone;
(c) 3 mg pomalidomide, 10 mg/kg of anti-CS1 antibody, and 40 mg dexamethasone; or
(d) 4 mg pomalidomide, 10 mg/kg of anti-CS1 antibody, and 40 mg dexamethasone.

In one embodiment, pomalidomide, the anti-CS1 antibody, and dexamethasone are administered at the following doses:
(a) 1 mg pomalidomide, 10 mg/kg of anti-CS1 antibody, and 8 mg dexamethasone IV;
(b) 2 mg pomalidomide, 10 mg/kg of anti-CS1 antibody, and 8 mg dexamethasone IV;
(c) 3 mg pomalidomide, 10 mg/kg of anti-CS1 antibody, and 8 mg dexamethasone IV; or
(d) 4 mg pomalidomide, 10 mg/kg of anti-CS1 antibody, and 8 mg dexamethasone IV.

In one embodiment, the anti-CS1 antibody and pomalidomide are administered as a first ("front") line of treatment (e.g., the initial or first treatment). In another embodiment, the anti-CS1 antibody and pomalidomide are administered as a second line of treatment (e.g., after initial treatment with the same or a different therapeutic, including after relapse and/or where the first treatment has failed).

In one embodiment, the anti-CS1 antibody, pomalidomide, and dexamethsone are administered as a first ("front") line of treatment (e.g., the initial or first treatment). In another embodiment, the anti-CS1 antibody, pomalidomide, and dexamethsone are administered as a second line of treatment (e.g., after initial treatment with the same or a different therapeutic, including after relapse and/or where the first treatment has failed).

The efficacy of the treatment methods provided herein can be assessed using any suitable means. In one embodiment, the treatment produces at least one therapeutic effect selected from the group consisting of complete response, very good partial response, partial response, and stable disease. In another embodiment, administration of pomalidomide and an anti-CS1 antibody has a synergistic effect on treatment compared to administration of either therapy alone.

The efficacy of the treatment methods provided herein can be assessed using any suitable means. In one embodiment, the treatment produces at least one therapeutic effect selected from the group consisting of complete response, very good partial response, partial response, and stable disease. In another embodiment, administration of pomalidomide, an anti-CS1 antibody, and dexamethasone has a synergistic effect on treatment compared to administration of either therapy alone.

Also provided are compositions comprising:
(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and
(b) pomalidomide.

Also provided are compositions comprising:
(a) an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
(b) pomalidomide; and
(c) dexamethasone The present invention provides a method for treating a multiple myeloma patient that has progressed after receiving an initial treatment comprising the administration of a combination therapeutic regiment in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination stops said progression and effectively treats said patients multiple myeloma.

The present invention provides a method for treating a multiple myeloma patient that has progressed after receiving an initial treatment comprising the administration of a combination therapeutic regiment in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination stops said progression and effectively treats said patients multiple myeloma, wherein said anti-CS1 antibody is elotuzumab.

The present invention provides a method for treating a multiple myeloma patient that has progressed after receiving an initial treatment comprising the administration of a combination therapeutic regiment in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination stops said progression and effectively treats said patients multiple myeloma, wherein said anti-CS1 antibody is elotuzumab, and wherein pomalidomide is administered at a dosage of about 4 mg, said elotuzumab is administered at a dosage of about 10 mg/kg, and dexamethasone is administered either orally at a dose of about 28 mg to 40 mg, or via IV at a dose of about 8 mg.

The present invention provides a method for treating a multiple myeloma patient that has progressed after receiving an initial treatment comprising the administration of a combination therapeutic regiment in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination stops said progression and effectively treats said patients multiple myeloma, wherein said anti-CS1 antibody is elotuzumab, and wherein pomalidomide is administered at a dosage of about 4 mg daily for 21 days, said anti-CS1 antibody is administered at a dosage of about 10 mg/kg once every three weeks, and dexamethasone is administered either orally at a dose of about 28 mg to 40 mg daily for 21 days, or via IV at a dose of about 8 mg weekly.

The present invention provides a method for treating a multiple myeloma patient that is resistant to lenalidomide comprising the administration of a combination therapeutic regimen in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination overcomes said patients lenalidomide resistance and effectively treats said patients multiple myeloma.

The present invention provides a method for treating a multiple myeloma patient that is resistant to lenalidomide comprising the administration of a combination therapeutic regimen in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination overcomes said patients lenalidomide resistance and effectively treats said patients multiple myeloma, wherein said anti-CS1 antibody is elotuzumab.

The present invention provides a method for treating a multiple myeloma patient that is resistant to lenalidomide comprising the administration of a combination therapeutic regimen in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination overcomes said patients lenalidomide resistance and effectively treats said patients multiple myeloma, wherein said anti-CS1 antibody is elotuzumab, and wherein pomalidomide is administered at a dosage of about 4 mg, said anti-CS1 antibody is administered at a dosage of about 10 mg/kg, and dexamethasone is administered either orally at a dose of about 28 mg to 40 mg, or via IV at a dose of about 8 mg.

The present invention provides a method for treating a multiple myeloma patient that is resistant to lenalidomide comprising the administration of a combination therapeutic regimen in which each component of said combination is separately administered, comprising: (i) a therapeutically effective amount of pomalidomide; (ii) a therapeutically effective amount of an anti-CS1 antibody; and (iii) a therapeutically acceptable amount of dexamethasone, wherein said combination overcomes said patients lenalidomide resistance and effectively treats said patients multiple myeloma, wherein said anti-CS1 antibody is elotuzumab, and wherein pomalidomide is administered at a dosage of about 4 mg daily for 21 days, said anti-CS1 antibody is administered at a dosage of about 10 mg/kg once every three weeks, and dexamethasone is administered either orally at a dose of about 28 mg to 40 mg daily for 21 days, or via IV at a dose of about 8 mg weekly.

The present invention provides a method for treating a multiple myeloma patient comprising the administration of a combination therapeutic regimen in which each component of said combination is separately administered, comprising: (i) a therapeutically effective amount of pomalidomide; (ii) a therapeutically effective amount of anti-CS1 antibody; and (iii) a therapeutically acceptable amount of dexamethasone, wherein said combination effectively treats said patients multiple myeloma, wherein said immunomodulatory agent is administered at a dosage of about 4 mg, said anti-CS1 antibody is administered at a dosage of about 10 mg/kg (optionally at 20 mg/kg), and dexamethasone is administered either orally at a dose of about 28 mg to 40 mg, or via IV at a dose of about 8 mg.

The present invention provides a method for treating a multiple myeloma patient comprising the administration of a combination therapeutic regimen in which each component of said combination is separately administered, comprising: (i) a therapeutically effective amount of pomalidomide; (ii) a therapeutically effective amount of anti-CS1 antibody; and (iii) a therapeutically acceptable amount of dexamethasone, wherein said combination effectively treats said patients multiple myeloma, wherein said immunomodulatory agent is administered at a dosage of about 4 mg, said anti-CS1 antibody is administered at a dosage of about 10 mg/kg (optionally at 20 mg/kg), and dexamethasone is administered either orally at a dose of about 28 mg to 40 mg, or via IV at a dose of about 8 mg, wherein said immunomodulatory agent is administered at a dosage of about 4 mg daily for 21 days, said anti-CS1 antibody is administered at a dosage of about 10 mg/kg once every three weeks, and dexamethasone is administered either orally at a dose of about 28 mg to 40 mg daily for 21 days, or via IV at a dose of about 8 mg weekly in an overall 28 day dosing cycle, and optionally wherein said anti-CS1 antibody is administered at a dose of about 20 mg/kg in subsequent dosing cycles other than the first cycle.

The present invention provides a method for treating a multiple myeloma patient comprising the administration of a combination therapeutic regimen in which each component of said combination is separately administered, comprising: (i) a therapeutically effective amount of pomalidomide; (ii) a therapeutically effective amount of anti-CS1 antibody; and (iii) a therapeutically acceptable amount of dexamethasone, wherein said combination effectively treats said patients multiple myeloma, wherein said immunomodulatory agent is administered at a dosage of about 4 mg, said anti-CS1 antibody is administered at a dosage of about 10 mg/kg (optionally at 20 mg/kg), and dexamethasone is administered either orally at a dose of about 28 mg to 40 mg, or via IV at a dose of about 8 mg, wherein said immunomodulatory agent is administered at a dosage of about 4 mg daily for 21 days, said anti-CS1 antibody is administered at a dosage of about 10 mg/kg once every three weeks, and dexamethasone is administered either orally at a dose of about 28 mg to 40 mg daily for 21 days, or via IV at a dose of about 8 mg weekly in an overall 28 day dosing cycle, and optionally wherein said anti-CS1 antibody is administered at a dose of about 20 mg/kg beginning with dosing cycle 3 and continuing at that dose in subsequent dosing cycles.

The present invention provides a method for treating a multiple myeloma patient comprising the administration of a combination therapeutic regimen in which each component of said combination is separately administered, comprising: (i) a therapeutically effective amount of pomalidomide; (ii) a therapeutically effective amount of anti-CS1 antibody; and (iii) a therapeutically acceptable amount of dexamethasone, wherein said combination effectively treats said patients multiple myeloma, wherein said immunomodulatory agent is administered at a dosage of about 4 mg, said anti-CS1 antibody is administered at a dosage of about 10 mg/kg (optionally at 20 mg/kg), and dexamethasone is administered either orally at a dose of about 28 mg to 40 mg, or via IV at a dose of about 8 mg, wherein said immunomodulatory agent is administered at a dosage of about 4 mg daily for 21 days, said anti-CS1 antibody is administered at a dosage of about 10 mg/kg once every three weeks, and dexamethasone is administered either orally at a dose of about 28 mg to 40 mg daily for 21 days, or via IV at a dose of about 8 mg weekly in an overall 28 day dosing cycle for cycles 1 and 2, and optionally wherein said anti-CS1 antibody is administered at a dose of about 20 mg/kg beginning with dosing cycle 3 and continuing at that dose in subsequent dosing cycles.

BRIEF DESCRIPTION OF THE FIGURES/DRAWINGS

FIG. 1. Antitumor Activity of pomalidomide treatment on OPM2 Multiple Myeloma Xenograft. Pomalidomide was administered at either 0.5 mg/kg, 5 mg/kg, or 50 mg/kg. Mice with established OPM2 xenograft tumors were randomized into groups (8 mice/group). Group one was left untreated (control, circles), group two treated with pomalidomide (50 mg/kg, triangles), group three treated with pomalidomide (5 mg/kg, squares), group four treated with pomalidomide (0.5 mg/kg, diamonds). All treatment sets were dosed daily for 5 days orally starting on d14 and then again for 5 days on d21. The data are presented as means+/−standard deviation. From this experiment the suboptimal 5 mg/kg dose was chosen as the dose to use in combination studies with elotuzumab and/or dexamethasone.

Figure 2A:
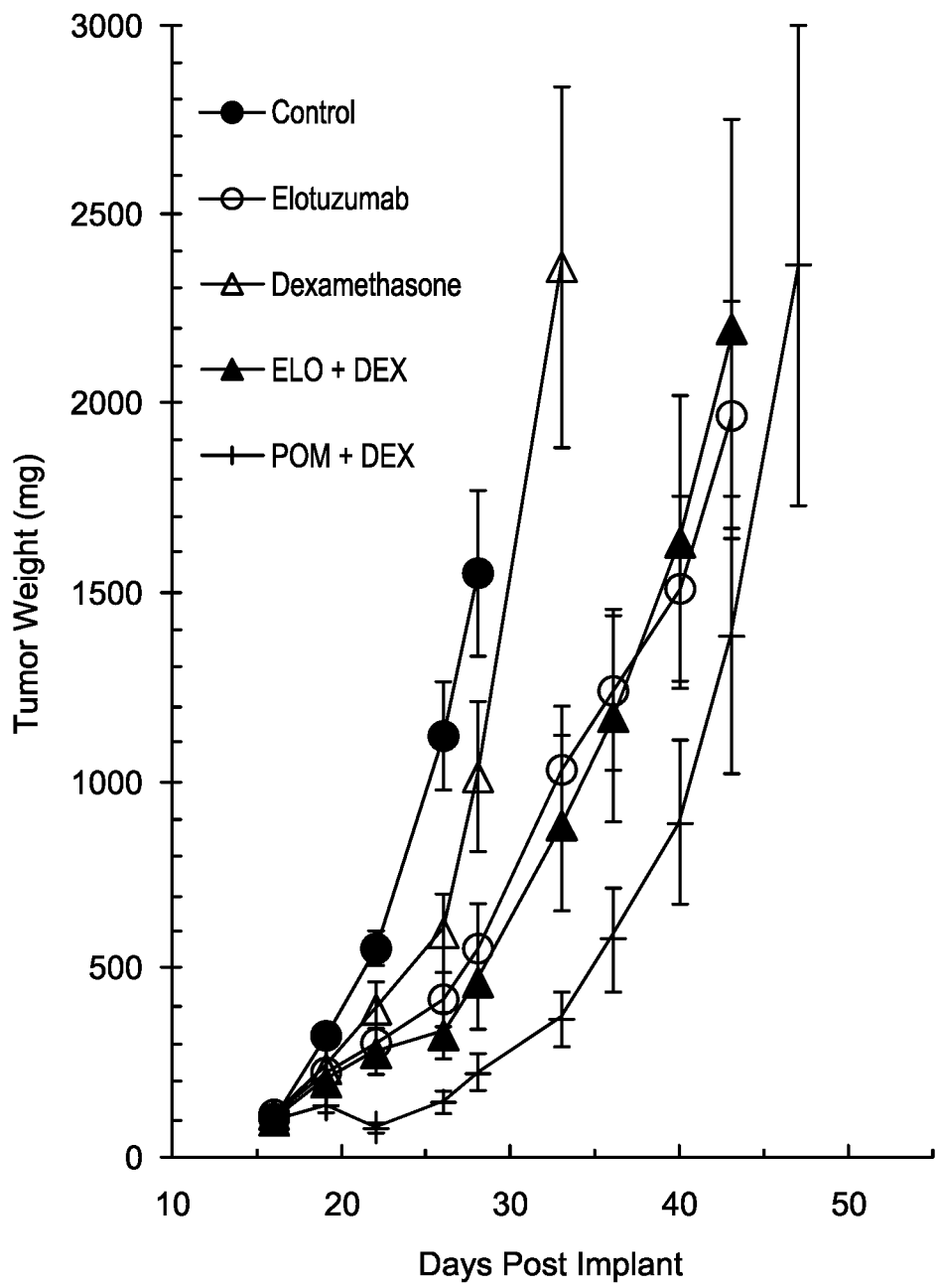
Figure 2B:
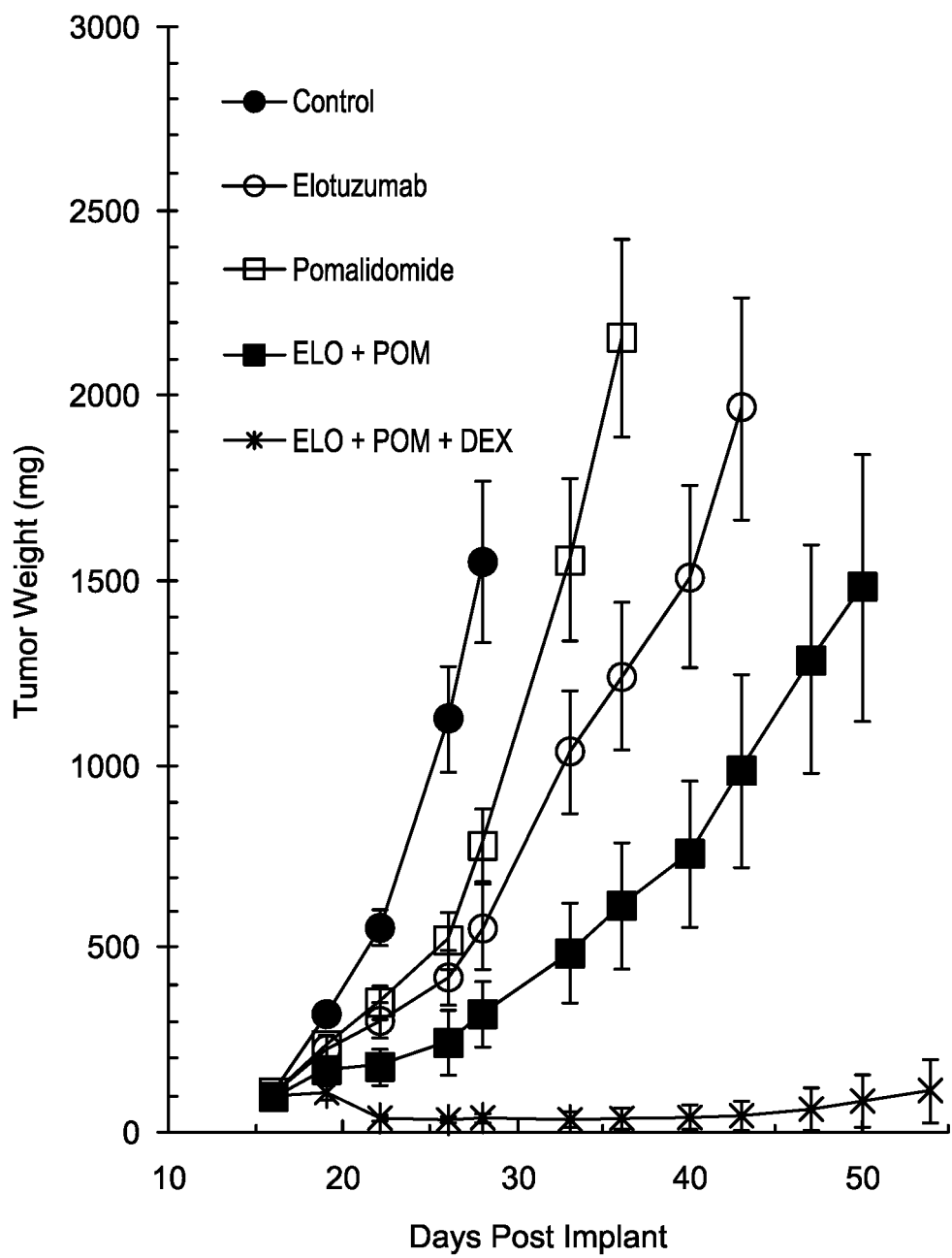
Figure 3A:
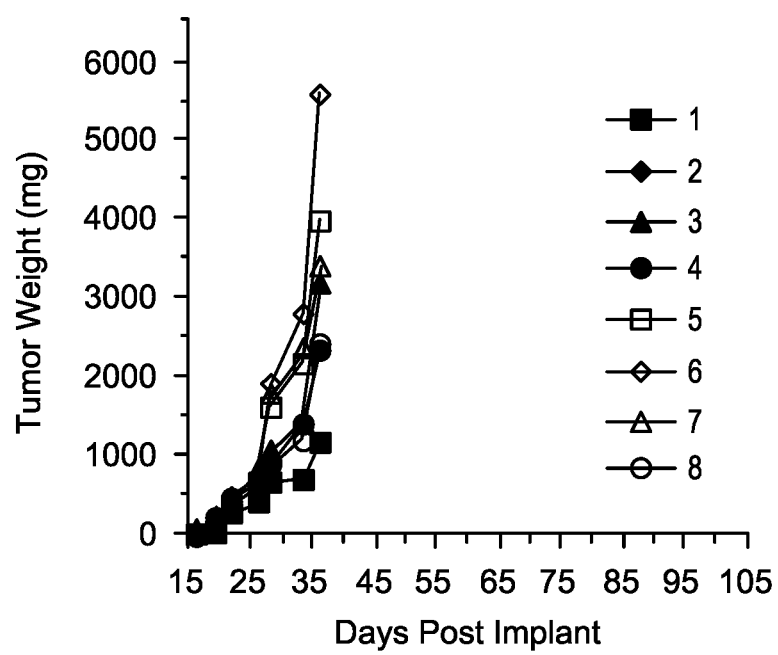
Figure 3B:
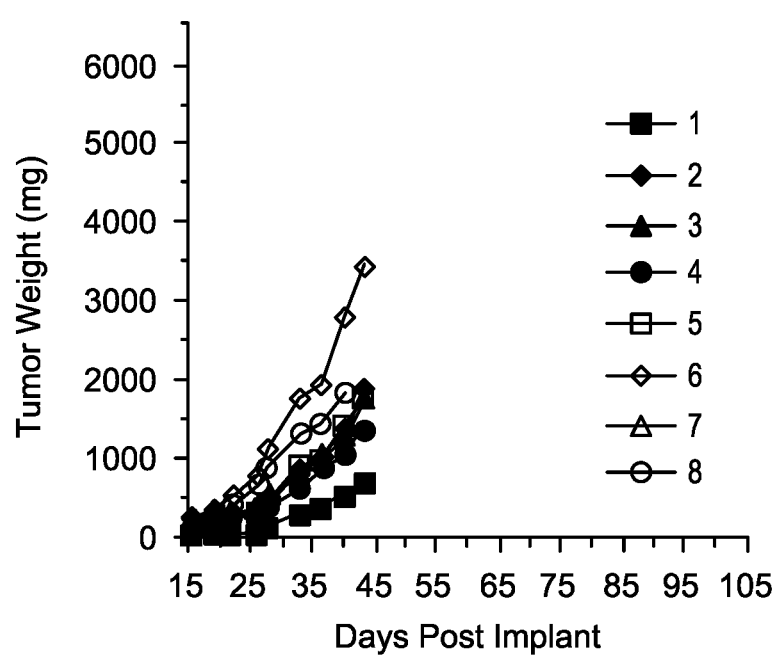
Figure 3C:
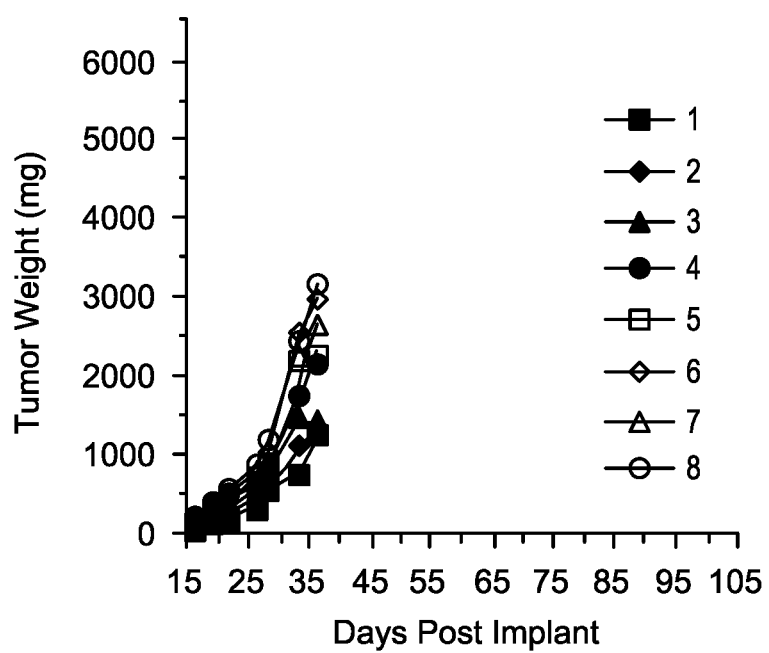
Figure 3D:
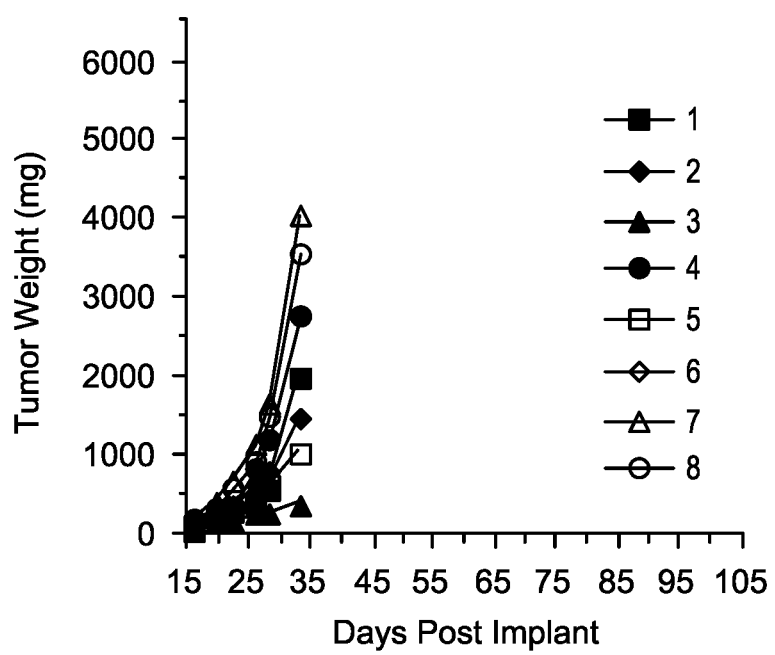
Figure 3E:
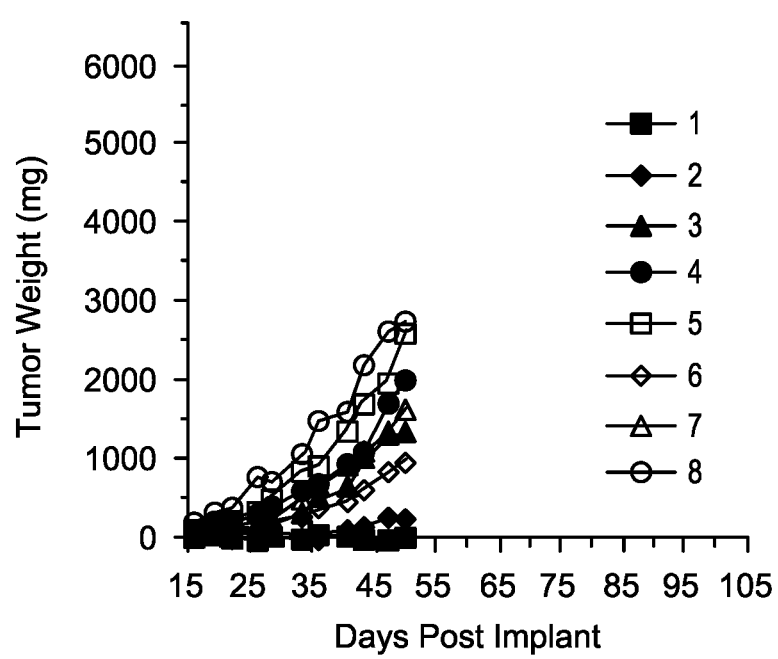
Figure 3F:
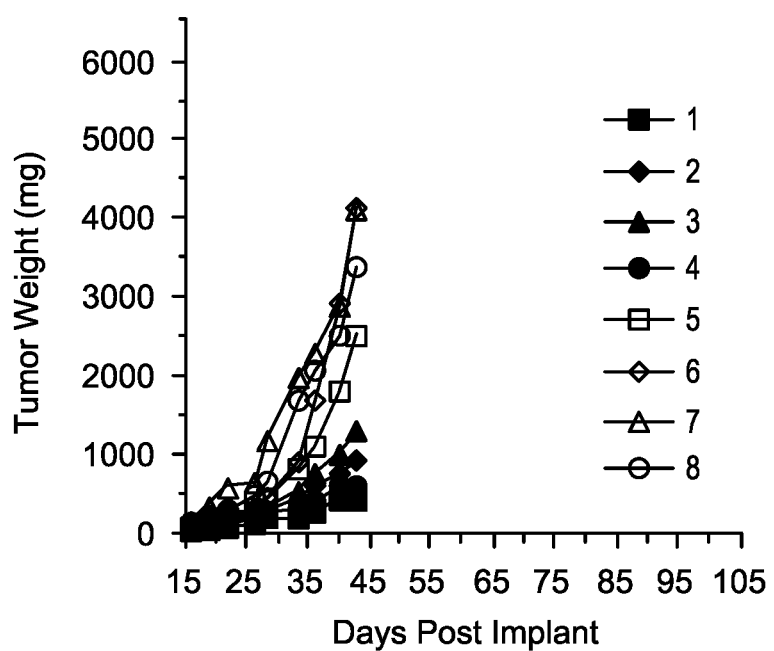
Figure 3G:
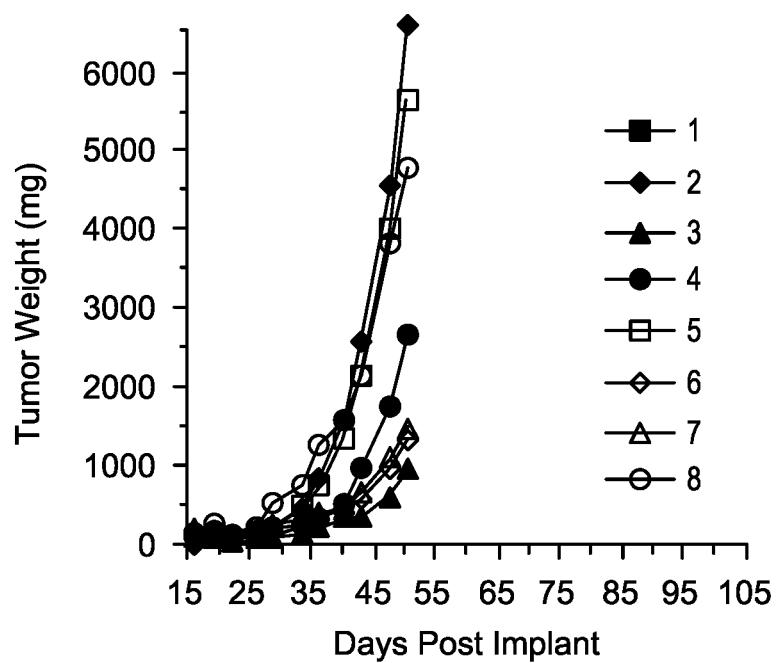
Figure 3H:
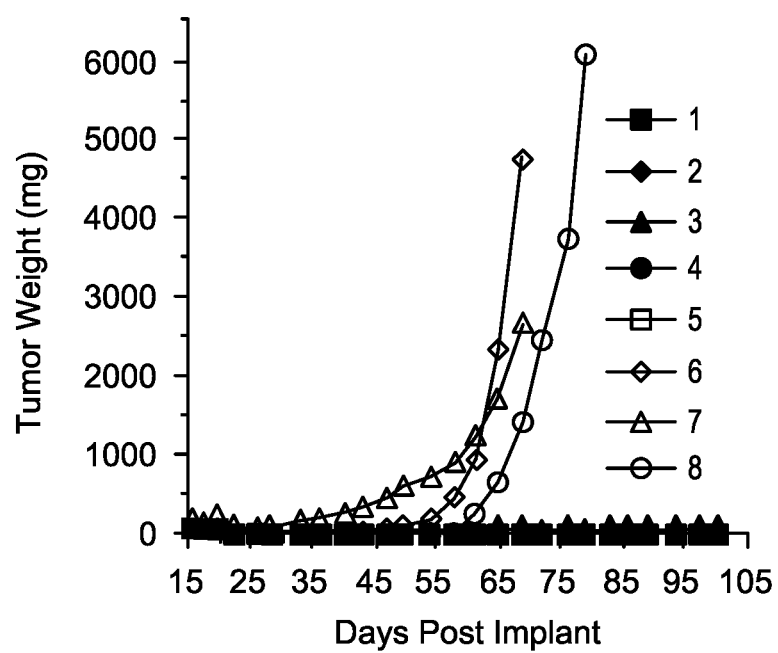

FIGS. 2A-B. Study #1 (OPM2-15), Antitumor Activity of Elotuzumab Efficacy in Combination with Pomalidomide and Dexamethasone in OPM2 Multiple Myeloma Xenograft. Mice with established OPM2 xenograft tumors were randomized into 2 groups with 8 mice per group and were administered one of the following sets of regimens: (A) Control group was left untreated (filled circles), elotuzumab (0.5 mg/kg, twice weekly IP for 7 doses starting d16, open circles), dexamethasone (5 mg/kg, daily IP for 7 doses starting on d16, open triangles), elotuzumab plus dexamethasone combination (filled triangles), pomalidomide (5 mg/kg, daily for 5 days orally starting on d16 and then again for 5 days on d23) plus dexamethasone combination (dashes); or (B) Control group was left untreated (filled circles), elotuzumab (0.5 mg/kg, twice weekly IP for 7 doses starting d16, open circles), pomalidomide (5 mg/kg, daily for 5 days orally starting on d16 and then again for 5 days on d23, open squares), elotuzumab (0.5 mg/kg, twice weekly IP for 10 doses starting d16) plus pomalidomide combination (filled squares), elotuzumab (10 doses) plus pomalidomide plus dexamethasone combination (x's). The data are presented as means+/−standard deviation. As shown, the triple combination of elotuzumab, pomalidomide, and dexamethasone resulted in synergistic inhibition of tumor growth in the OPM-2 tumor model compared to either agent alone.

FIGS. 3A-H. Study #1 (OPM2-15), Anti Tumor Activity of Elotuzumab, Pomalidomide, and Dexamethasone as Single Agent and Combination Treatment in OPM2 Multiple Myeloma Xenograft tumor model. Mice with established OPM2 xenograft tumors were randomized into groups with 8 mice per group and were administered one of the following regimens: (A): untreated (control); (B): elotuzumab; (C): pomalidomide; (D): dexamethasone; (E): elotuzumab plus pomalidomide; (F): elotuzumab plus dexamethasone; (G): pomalidomide plus dexamethasone; or (H): elotuzumab plus pomalidomide plus dexamethasone. Data represent tumor weight measured in individual animals. Dosing route and regimen are described in FIG. 2 and Example 1. As shown, tumor growth was significantly inhibited only in the mice that were administered the triple combination of elotuzumab, pomalidomide, and dexamethasone.

Figure 4A:
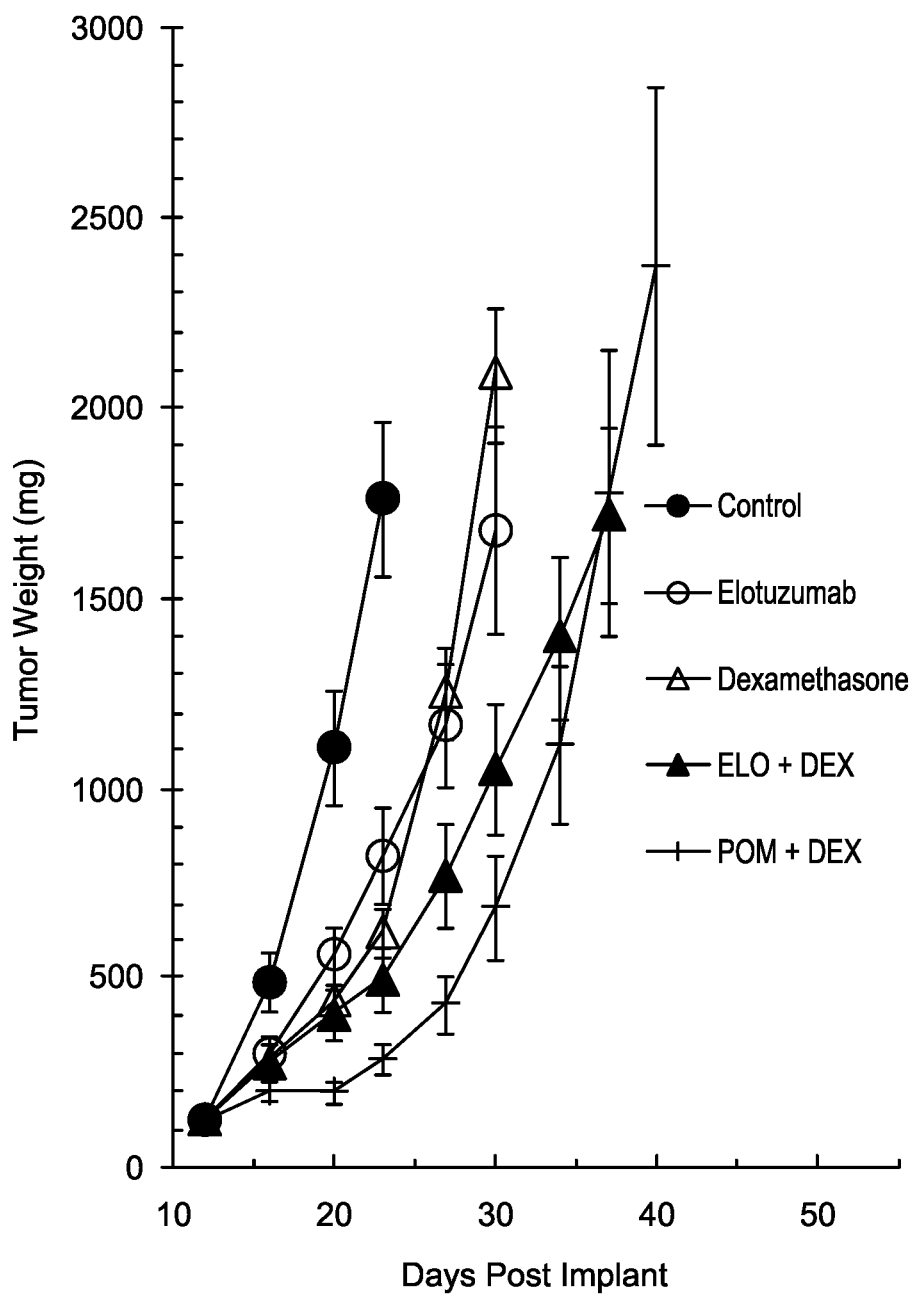
Figure 4B:
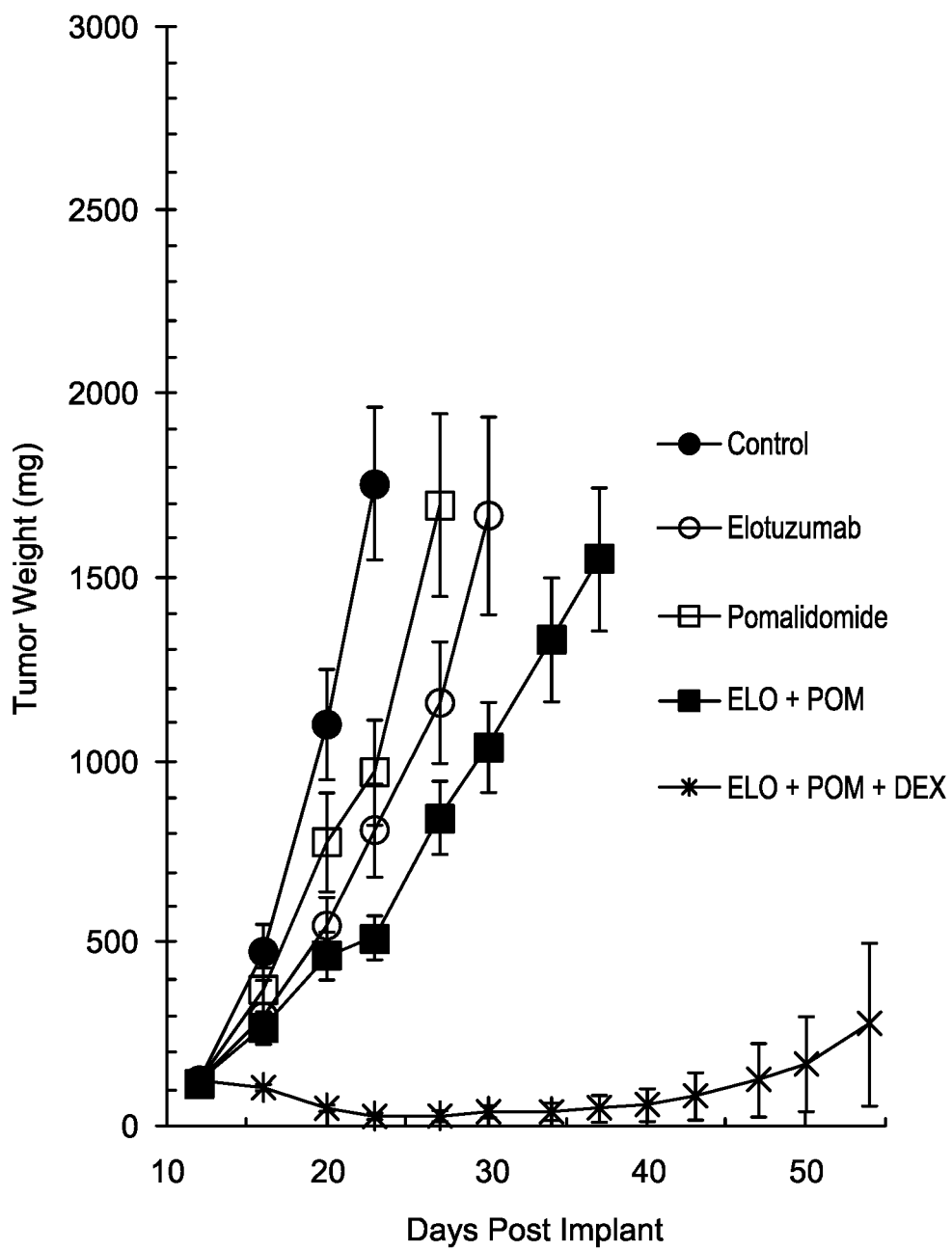
Figure 5A:
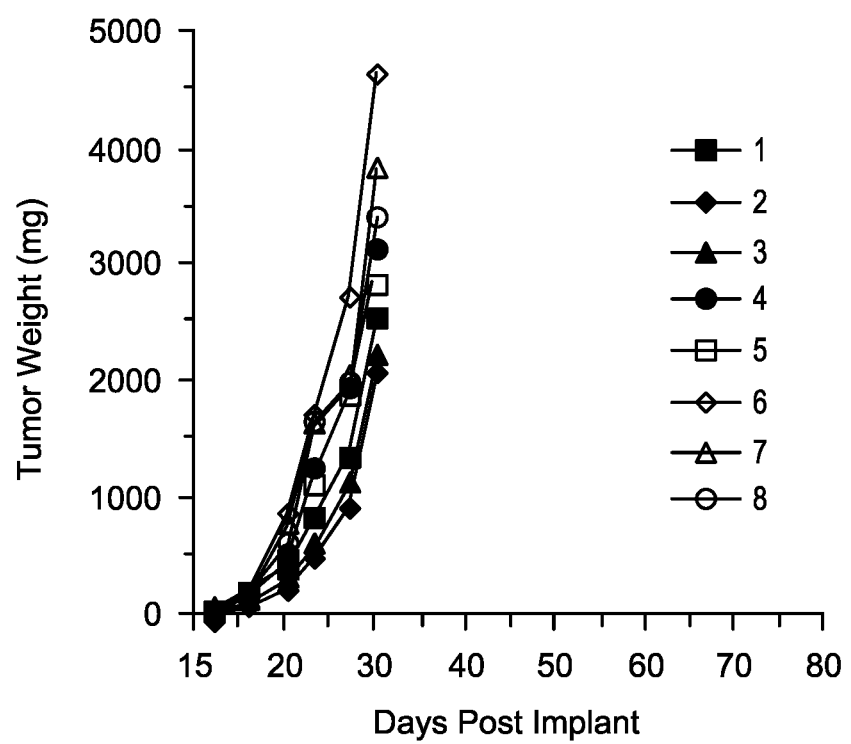
Figure 5B:
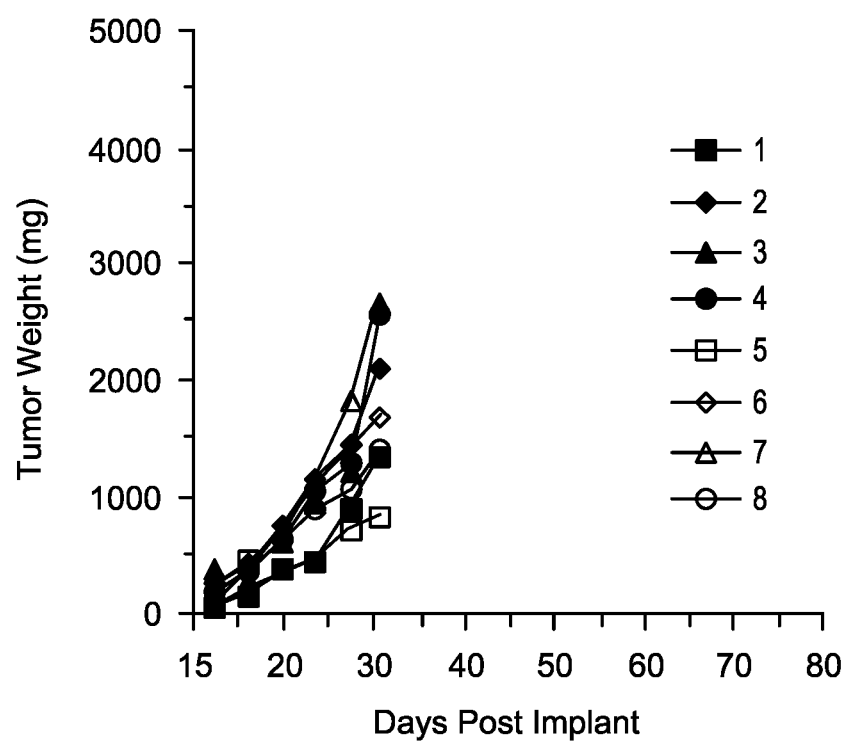
Figure 5C:
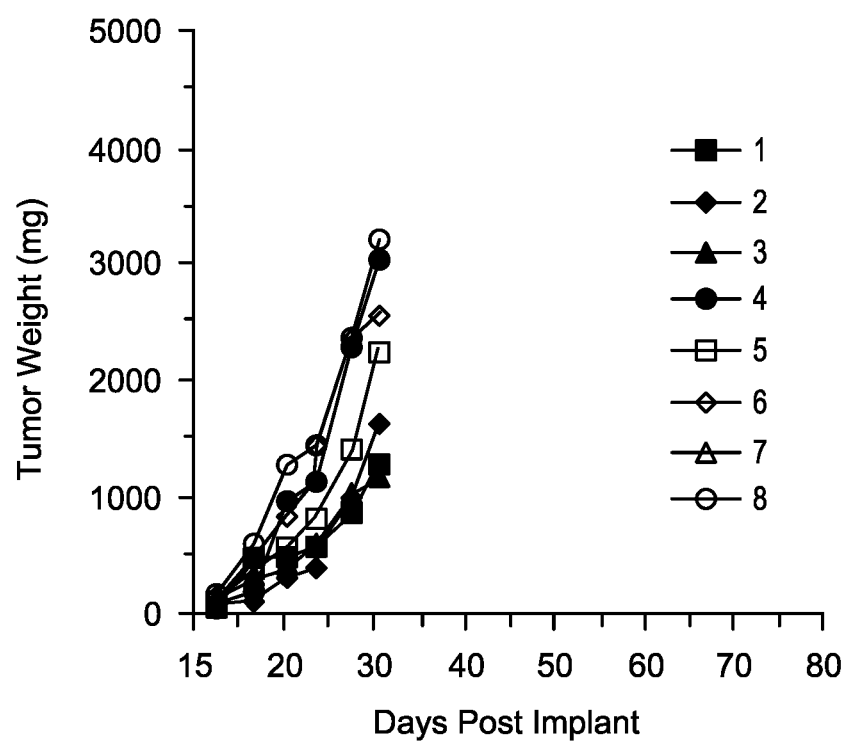
Figure 5D:
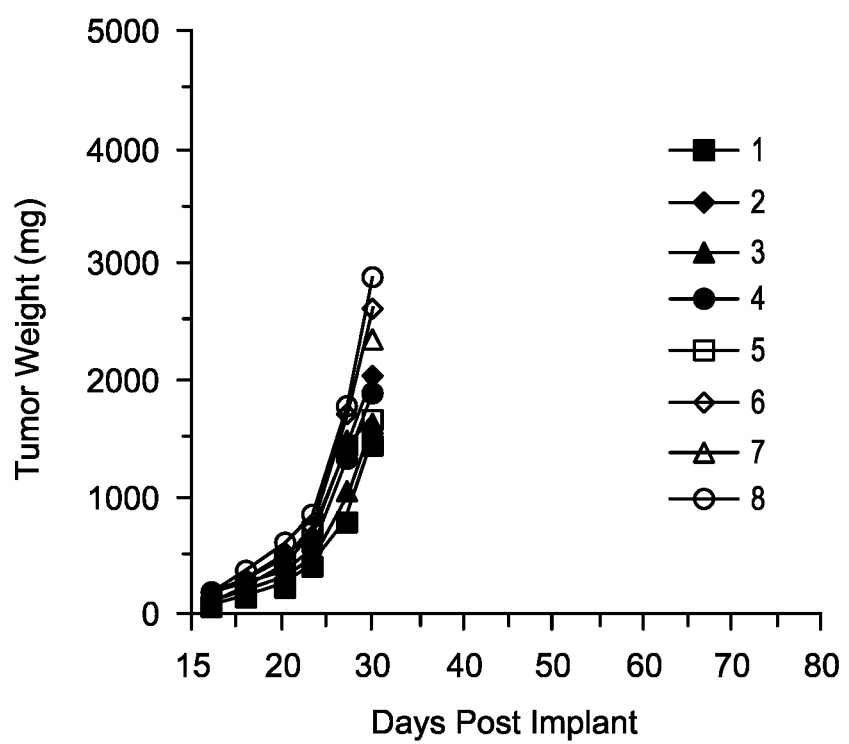
Figure 5E:
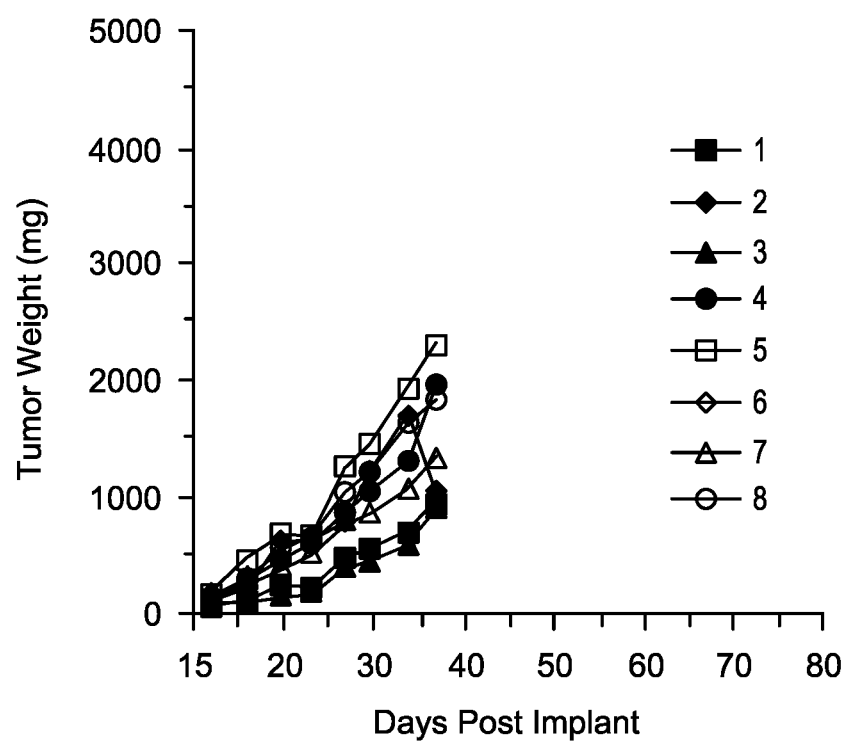
Figure 5F:
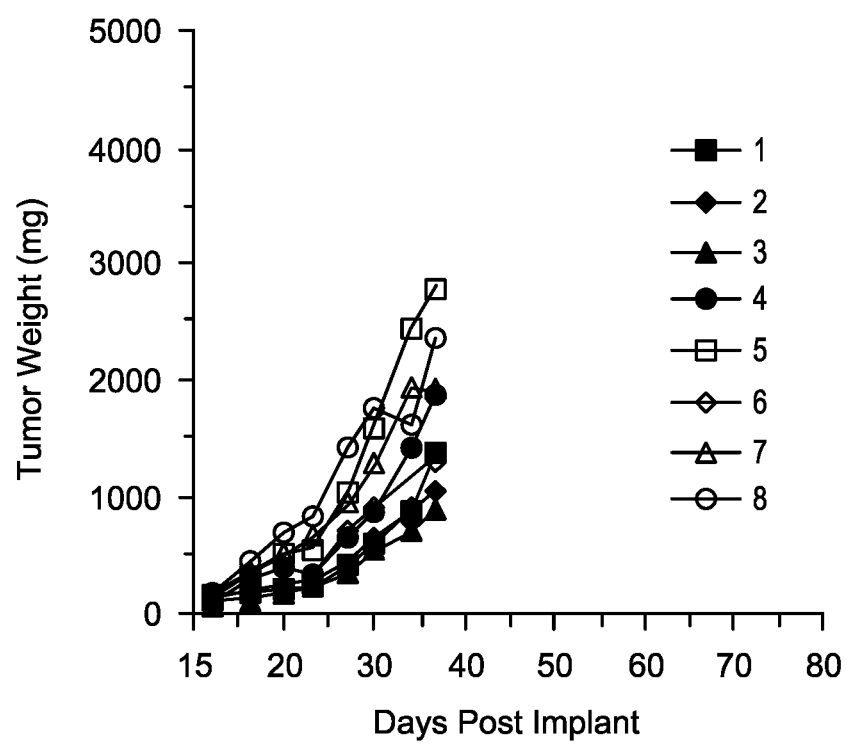
Figure 5G:
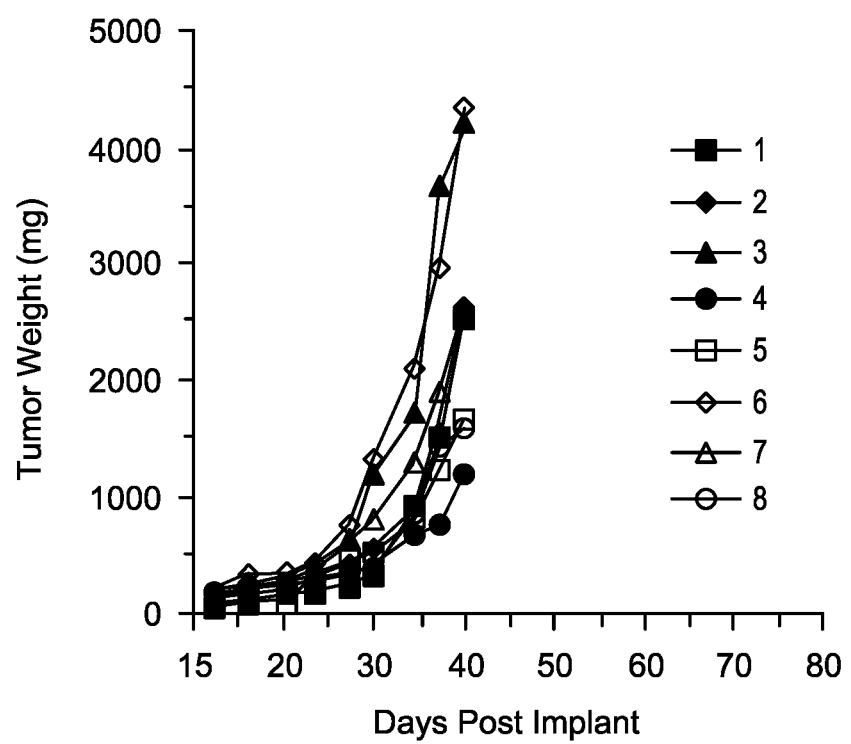
Figure 5H:
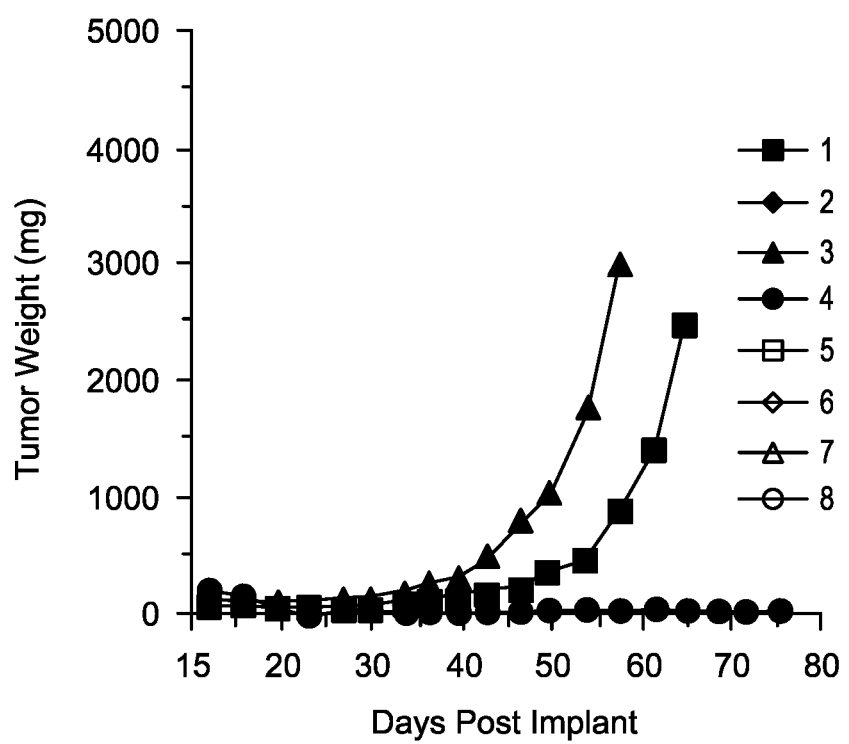

FIGS. 4A-B. Study #2 (OPM2-16), Antitumor Activity, Elotuzumab Efficacy in Combination with Pomalidomide and Dexamethasone in OPM2 Multiple Myeloma Xenograft. Mice with established OPM2 xenograft tumors were randomized into 2 groups with 8 mice per group and were administered one of the following sets of regimens: (A) Control group was left untreated (filled circles), elotuzumab (0.5 mg/kg, twice weekly IP for 6 doses starting d12, open circles), dexamethasone (5 mg/kg, daily IP for 7 doses starting on d12, open triangles), elotuzumab (0.5 mg/kg, twice weekly IP for 8 doses starting d12) plus dexamethasone combination (filled triangles), pomalidomide (5 mg/kg, daily for 5 days orally starting on d12 and then again for 5 days on d19) plus dexamethasone combination (dashes); or (B) Control group was left untreated (filled circles), elotuzumab (0.5 mg/kg, twice weekly IP for 6 doses starting d12, open circles), pomalidomide (5 mg/kg, daily for 5 days orally starting on d12 and then again for 5 days on d19, open squares), elotuzumab (0.5 mg/kg, twice weekly IP for 8 doses starting d12) plus pomalidomide combination (filled squares), elotuzumab (0.5 mg/kg, twice weekly IP for 8 doses starting d12) plus pomalidomide plus dexamethasone combination (x's). The data are presented as means+/−standard deviation. As shown, the triple combination of elotuzumab, pomalidomide, and dexamethasone resulted in synergistic inhibition of tumor growth in the OPM-2 tumor model compared to either agent alone.

FIGS. 5A-H. Study #2 (OPM2-16), Anti Tumor Activity of Elotuzumab, Pomalidomide, and Dexamethasone as Single Agent and Combination Treatment in OPM2 Multiple Myeloma Xenograft tumor model. Mice with established OPM2 xenograft tumors were randomized into groups with 8 mice per group and were administered one of the following regimens: (A): untreated (control); (B): elotuzumab; (C): pomalidomide; (D): dexamethasone; (E): elotuzumab plus pomalidomide; (F): elotuzumab plus dexamethasone; (G): pomalidomide plus dexamethasone; or (H): elotuzumab plus pomalidomide plus dexamethasone. Data represent tumor weight measured in individual animals. Dosing route and regimen are described in FIG. 4 and Example 1. As shown, tumor growth was significantly inhibited only in the mice that were administered the triple combination of elotuzumab, pomalidomide, and dexamethasone.

Figure 6:
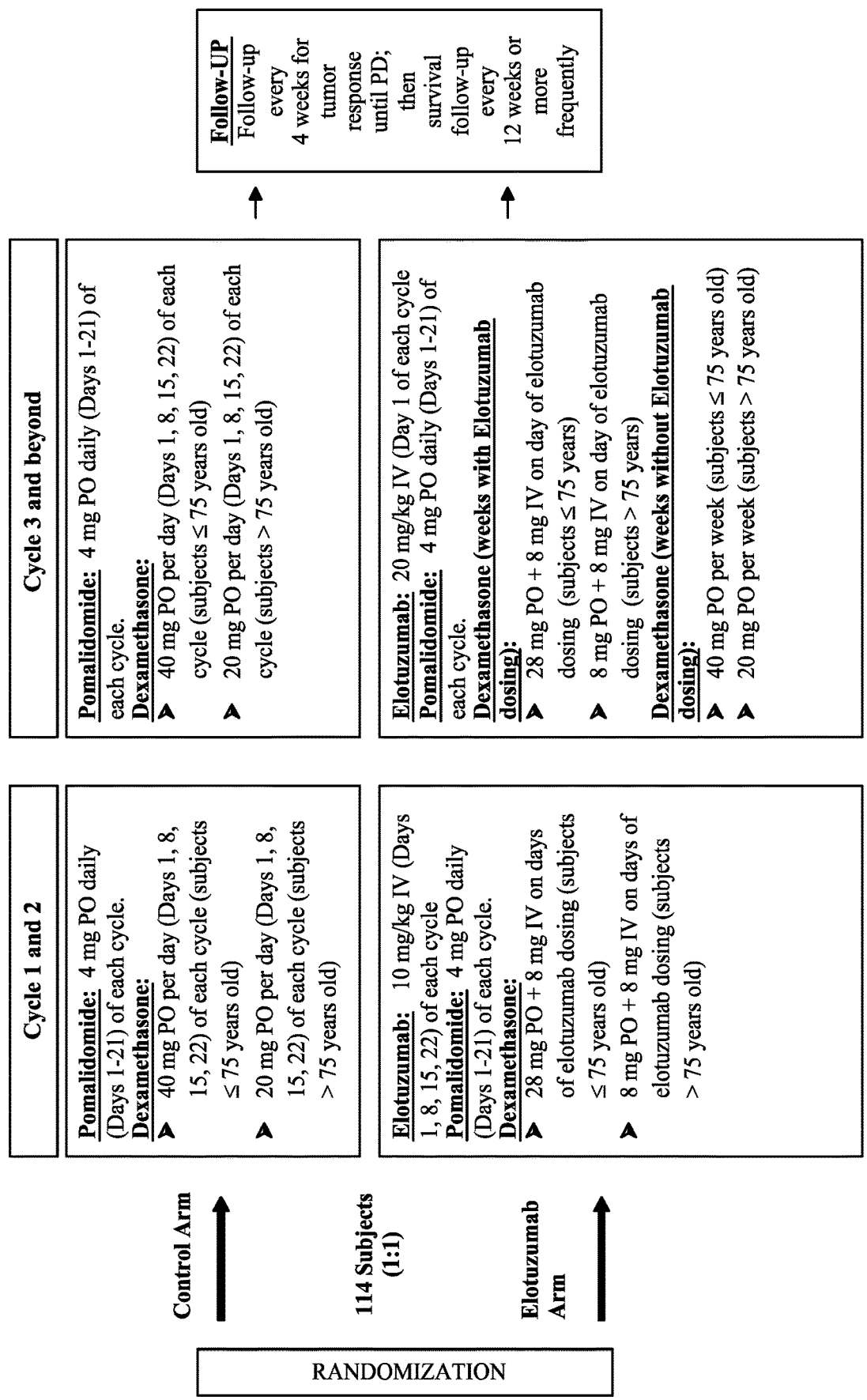

FIG. 6. Schema for CA204125, an Open Label, Randomized Phase 2 Trial Investigating the Combination of Pomalidomide/Dexamethasone With or Without Elotuzumab in relapsed and refractory Multiple Myeloma.

Figure 7:
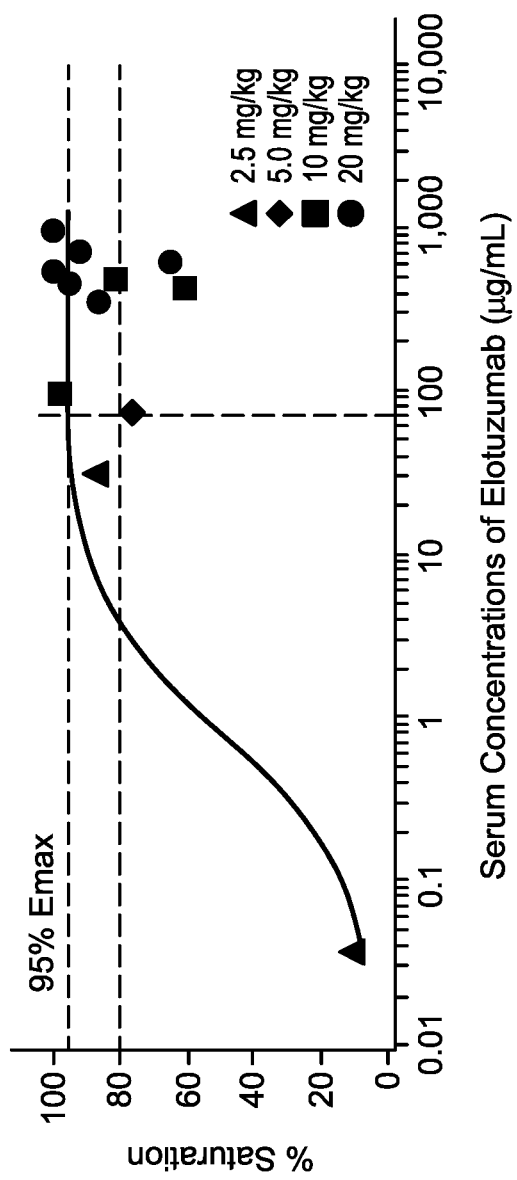

FIG. 7. Saturation of SLAMF7 Target on Bone Marrow Myeloma Samples from Subjects Treated in a Phase 2 Study of Elotuzumab and Lenalidomide/Dexamethasone (HuLuc63).

DETAILED DESCRIPTION OF THE INVENTION

The present invention is based on data from preclinical studies conducted in female SCID mice (6-8 weeks old) that were implanted SC (subcutaneous implantation) with the multiple myeloma cell line OPM-2 which were treated with Elotuzumab IP (intraperitoneal administration) alone, treated with pomalidomide alone, treated with dexamethasone alone, or treated in combination with each other. The results demonstrated for the first time that the combination of pomalidomide and elotuzumab demonstrated better efficacy than either of the agents alone. In addition, combination of pomalidomide and dexamethasone also demonstrated better efficacy than either of the agents alone. Surprisingly, however, the triple combination of elotuzumab, pomalidomide, and dexamethasone elicited complete tumor regressions in 8 of 16 the treated mice, and partial tumor regressions in 5 of 16 treated mice. Importantly, complete tumor regressions were not observed for any other treatment tested demonstrating the significance of the triple combination. All treatments were well tolerated, with no significant changes in body weights or overt signs of clinical toxicity. Based on these results, the triple combination was selected for clinical evaluation.

The teachings of the present invention are believed to be the first association between the administration of an anti-CS1 agent in combination with pomalidomide with increased, and in some cases synergistic, outcomes in terms of efficacy, safety, and tolerability.

In addition, the teachings of the present invention are believed to be the first association between the administration of an anti-CS1 agent in combination with pomalidomide and dexamethasone, with synergistic outcomes in terms of efficacy, safety, and tolerability.

The phrase "an anti-CS1 cycle" or "cycle of an anti-CS1 agent" or "cycles of a therapeutically effective amount of an anti-CS1 antibody" is meant to encompass either one or more dosing cycle(s) of an anti-CS1 agent, or one or more dosing cycle(s) of a combination comprising one or more anti-CS1 agent(s).

For the purposes of the present invention, "one or more cycles of an anti-CS1 dosing cycle" and/or "one or more dosing cycles of an anti-CS1 agent" and/or "one or more cycles of an anti-CS1 dosing cycle" and/or "one or more dosing cycles of an anti-CS1 agent" means at least 1, at least 2, at least 3, at least 4, at least 5, at least 6, at least 7, at least 8, at least 9, or at least 10 cycles of primary treatment with either agent(s), followed by one or more optional maintenance cycles of either agent(s). The maintenance cycle(s) may follow a similar number of cycles as outlined for the primary therapy, or may be significantly longer or shorter in terms of cycle number, depending upon the patient's disease and/or severity.

The phrase "concurrent dosing regimen", generally refers to treating a patient with one or more therapies at either the same time or within a short period after each other. For example, a concurrent dosing regimen may entail treating a patient with elotuzumab and pomalidomide at essentially the same time, or may entail treating a patient with elotuzumab, pomalidomide, and dexamethasone at essentially the same time.

The phrase "sequential dosing regimen", generally refers to treating a patient with at least two agents in a specific order, wherein one cycle of a first agent is administered after the cycle of another agent. In addition, the phrase "sequential dosing regimen" also encompasses the phrase "phased dosing regimen" as it is traditionally referred to in the pharmaceutical arts. In one context, "sequential dosing regimen" refers to not only the order in which the cycles are administered, but also to the entire treatment regimen for the patient. For example, "sequential dosing regimen" may include the complete dosing regimen for the patient including one or more cycles of an anti-CS1 agent, followed by one or more cycles of either pomalidomide or a combination comprising pomalidomide and one or more anti-CS1 agent.

For the purposes of the present invention, the concurrent administration of an anti-CS1 agent with pomalidomide, or the sequential administration of an anti-CS1 agent followed by pomalidomide, may be administered after a sufficient period of time after a patients prior therapy has passed, which may be at least about 3 weeks, about 4 weeks, about 5 weeks, about 6 weeks, about 7 weeks, about 8 weeks, about 9 weeks, about 10 weeks, about 11 weeks, about 12 weeks, or more weeks after the patients prior therapy has ended and/or after the physician has determined the prior therapy had failed.

The phrase "clinical benefit" or "benefit" refers to a condition where a patient achieves a complete response; partial response; stable disease; or as otherwise described herein.

In another aspect of the present invention, the concurrent administration of an anti-CS1 agent with pomalidomide, or the sequential administration of an anti-CS1 agent followed by pomalidomide, may be administered in further combination with one or more immunomodulatory agents, co-stimulatory pathway modulators.

The phrase "immunomodulatory agent" generally refers to an agent that either increases or decreases the function of the immune system, and/or as defined elsewhere herein, and includes co-stimulatory pathway modulators, Ipilimumab; ORENCIA®; Belatacept; CD28 antagonists, CD80 antagonists, CD86 antagonists, PD1 antagonists, PDL1 antagonists, CTLA-4 antagonists, and MR antagonists, among others disclosed herein. In addition, IMiDs are also generally referred to as immunomodulatory agents and includes, but is not limited to thalidomide (THALOMID®), lenalidomide (REVLIMID®), and pomalidomide (POMALYST®).

The phrase "anti-CS1 agent" generally refers to an agent that binds to CS1, may modulate and/or inhibit CS1 activity, may activate NK cells, and may be an anti-CS1 antibody, including Elotuzumab.

The phrase "anti-PD1 agent" generally refers to an agent that binds to PD1, may modulate and/or inhibit PD1 activity, may inhibit one of its ligands (PDL1, PDL2, etc.) to bind to the PD1 receptor, and may be an anti-PD1 antibody, including nivolumab and pembrolizumab.

In another embodiment of the present invention, the combination between an anti-CS1 agent, an IMiD and dexamethasone, may further comprise an anti-PD1 agent. In specific embodiments, the present invention encompasses the following combinations: an anti-CS1 agent+pomalidomide+dexamethasone+an anti-PD1 agent; an anti-CS1 agent+pomalidomide+low-dose dexamethasone+an anti-PD1 agent; an anti-CS1 agent+pomalidomide+high-dose dexamethasone+an anti-PD1 agent; an anti-CS1 agent+pomalidomide+dexamethasone tablets+an anti-PD1 agent; wherein said anti-PD1 agent is an anti-PD1 agent disclosed herein, including nivolumab or pembrolizumab.

The phrase "co-stimulatory pathway modulator", generally refers to an agent that functions by increasing or decreasing the function of the immune system by modulating the co-stimulatory pathway. In one aspect of the present invention, a co-stimulatory pathway modulator is an immunostimulant or T-cell activator, and may also encompass any agent that is capable of disrupting the ability of CD28 antigen to bind to its cognate ligand, to inhibit the ability of CTLA-4 to bind to its cognate ligand, to augment T cell responses via the co-stimulatory pathway, to disrupt the ability of B7 to bind to CD28 and/or CTLA-4, to disrupt the ability of B7 to activate the co-stimulatory pathway, to disrupt the ability of CD80 to bind to CD28 and/or CTLA-4, to disrupt the ability of CD80 to activate the co-stimulatory pathway, to disrupt the ability of CD86 to bind to CD28 and/or CTLA-4, to disrupt the ability of CD86 to activate the co-stimulatory pathway, and to disrupt the co-stimulatory pathway, in general from being activated. This necessarily includes small molecule inhibitors of CD28, CD80, CD86, CTLA-4, among other members of the co-stimulatory pathway; antibodies directed to CD28, CD80, CD86, CTLA-4, among other members of the co-stimulatory pathway; antisense molecules directed against CD28, CD80, CD86, CTLA-4, among other members of the co-stimulatory pathway; adnectins directed against CD28, CD80, CD86, CTLA-4, among other members of the co-stimulatory pathway, RNAi inhibitors (both single and double stranded) of CD28, CD80, CD86, CTLA-4, among other members of the co-stimulatory pathway, among other anti-CTLA-4 antagonists.

Anti-CTLA-4 antagonist agents for use in the methods of the invention, include, without limitation, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, MDX-010 (Ipilimumab), tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, modulators of the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: PCT Publication No. WO 98/42752; U.S. Pat. Nos. 6,682,736 and 6,207,156; Hurwitz et al., *Proc. Natl. Acad. Sci. USA,* 95(17):10067-10071 (1998); Camacho et al., *J. Clin. Oncology,* 22(145):Abstract No. 2505 (2004) (antibody CP-675206); Mokyr et al., *Cancer Res.,* 58:5301-5304 (1998), and U.S. Pat. Nos. 5,977,318, 6,682,736, 7,109,003, and 7,132,281. Each of these references is specifically incorporated herein by reference for purposes of description of CTLA-4 antibodies. A preferred clinical CTLA-4 antibody is human monoclonal antibody 10D1 (also referred to as MDX-010 and Ipilimumab and available from Medarex, Inc., Bloomsbury, N.J.), disclosed in PCT Publication No. WO 01/14424.

As is known in the art, Elotuzumab refers to an anti-CS1 antibody, and is a humanized antibody anti-CS1monoclonal antibody that enhances natural killer cell mediated antibody dependent cellular cytotoxicity of CS1 expressing myeloma cells. Elotuzumab can also be referred to as BMS-901608, or by its CAS Registry No. 915296-00-3, and is disclosed as antibody HuLuc63 in PCT Publication No. WO 2004/100898, incorporated herein by reference in its entirety and for all purposes. Specifically, Elotuzumab describes a humanized monoclonal antibody or antigen-binding portion thereof that specifically binds to CS-1, comprising a light chain variable region and a heavy chain variable region having a light chain variable region comprised of SEQ ID NO:1, and comprising a heavy chain region comprised of SEQ ID NO:2, or antigen binding fragments and variants thereof. Elotuzumab may also be described as an antibody comprising a heavy chain CDR1 having amino acids 31-35 of SEQ ID NO:2: a heavy chain CDR2 having amino acids 50-66 of SEQ ID NO:2; and a heavy chain CDR3 having amino acids 99-108 of SEQ ID NO:2; in addition to a light chain CDR1 having amino acids 24-34 of SEQ ID NO:1; a light chain CDR2 having amino acids 50-56 of SEQ ID NO:1; and a light chain CDR3 having amino acids 89-97 of SEQ ID NO:1. Pharmaceutical compositions of Elotuzumab include all pharmaceutically acceptable compositions comprising Elotuzumab and one or more diluents, vehicles and/or excipients. Elotuzumab may be administered by I.V. at a dose of about 1 mg/kg, 10 mg/kg, about 20 mg/kg, or between about 10 to about 20 mg/kg.

```
Light chain variable region for Elotuzumab:
                                        (SEQ ID NO: 1)
DIQMTQSPSSLSASVGDRVTITCKASQDVGIAVAWYQQKPGKVPKLLIYW
ASTRHTGVPDRFSGSGSGTDFTLTISSLQPEDVATYYCQQYSSYPYTFGQ
GTKVEIK Heavy chain variable region for Elotuzumab:
                                        (SEQ ID NO: 2)
EVQLVESGGGLVQPGGSLRLSCAASGFDFSRYWMSWVRQAPGKGLEWIGE
INPDSSTINYAPSLKDKFIISRDNAKNSLYLQMNSLRAEDTAVYYCARPD
GNYWYFDVWGQGTLVTVSS
```

As is known in the art, pomalidomide is also referred to as (RS)-4-amino-2-(2,6-dioxo-piperidin-3-yl)-isoindole-1,3-dione and describes a compound having the following structure (I):

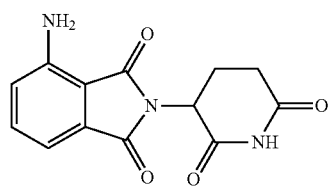

(I)

Compound (I) has a CAS Registry Number of 19171-19-8, has an empirical formula of $C_{13}H_{11}N_3O_4$; a gram molecular weight is 273.24, has a chiral carbon atom which exists as a racemic mixture of the R(+) and S(−) enantiomers. and is described in U.S. Pat. No. 5,635,517, published Jun. 3, 1997, incorporated herein by reference in its entirety and for all purposes. Use of the term "(RS)-4-amino-2-(2,6-dioxo-piperidin-3-yl)-isoindole-1,3-dione" encompasses (unless otherwise indicated) solvates (including hydrates) and polymorphic forms of the compound (I) or its salts (such as the acid addition salt of (I) described in U.S. Pat. No. 8,158,653, granted Apr. 17, 2012, incorporated herein by reference in its entirety and for all purposes). Pharmaceutical compositions of (RS)-4-amino-2-(2,6-dioxo-piperidin-3-yl)-isoindole-1,3-dione include all pharmaceutically acceptable compositions comprising (RS)-4-amino-2-(2,6-dioxo-piperidin-3-yl)-isoindole-1,3-dione and one or more diluents, vehicles and/or excipients, such as those compositions described in U.S. Pat. Nos. 6,316,471, 6,476,052, 8,158,653, 8,198,26, 8,673,939, 8,735,428, and 8,828,427, incorporated herein by reference in their entirety and for all purposes. One example of a pharmaceutical composition comprising (RS)-4-amino-2-(2,6-dioxo-piperidin-3-yl)-isoindole-1,3-dione is POMALYST® (Celgene Corporation). POMALYST® comprises (RS)-4-amino-2-(2,6-dioxo-piperidin-3-yl)-isoindole-1,3-dione as the active ingredient, also referred to as pomalidomide, and the following inactive ingredients: mannitol, pregelatinized starch and sodium stearyl fumarate. POMALYST® is available in 1 mg, 2 mg, 3 mg and 4 mg capsules for oral administration. The 1 mg capsule shell contains gelatin, titanium dioxide, FD&C blue 2, yellow iron oxide, white ink and black ink. The 2 mg capsule shell contains gelatin, titanium dioxide, FD&C blue 2, yellow iron oxide, FD&C red 3 and white ink. The 3 mg capsule shell contains gelatin, titanium dioxide, FD&C blue 2, yellow iron oxide and white ink. The 4 mg capsule shell contains gelatin, titanium dioxide, FD&C blue 1, FD&C blue 2 and white ink.

As noted elsewhere herein, the administration of an anti-CS1 agent and/or pomalidomide, may be administered either alone or in combination with a peptide antigen (e.g., gp100). A non-limiting example of a peptide antigen would be a gp100 peptide comprising, or alternatively consisting of, the sequence selected from the group consisting of: IMDQVPFSV (SEQ ID NO:3), and YLEPGPVTV (SEQ ID NO:4). Such a peptide may be administered orally, or preferably at 1 mg emulsified in incomplete Freund's adjuvant (IFA) injected s.c. in one extremity, and 1 mg of either the same or a different peptide emulsified in IFA may be injected in another extremity.

Preferred disorders for which the combination therapy of the present invention may be useful in treating patients includes, but are not limited to: myeloma. multiple myeloma, relapsed multiple myeloma, refractory multiple myeloma, smoldering multiple myeloma, high risk multiple myeloma, advanced multiple myeloma, multiple myeloma that is resistant to lenalidomide, multiple myeloma that has progressed after treatment with lenalidomide, multiple myeloma that is resistant to thalidomide, and multiple myeloma that has progressed after treatment with thalidomide.

Additional disorders for which the combination therapy of the present invention may be useful in treating patients include, but are not limited to: multiple myeloma, melanoma, primary melanoma, unresectable stage III or IV malignant melanoma, lung cancer, non-small cell lung cancer, small cell lung cancer, prostate cancer; solid tumors, pancreatic cancer, prostatic neoplasms, breast cancer, neuroblastoma, kidney cancer, ovarian cancer, sarcoma, bone cancer, testicular cancer, hematopoietic cancers, leukemia, lymphoma, multiple myeloma, and myelodysplastic syndromes.

Further disorders for which the combination therapy of the present invention may be useful in treating include, but are not limited to the following: glioma, gastrointestinal cancer, renal cancer, ovarian cancer, liver cancer, colorectal cancer, endometrial cancer, kidney cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, Philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

The terms "treating", "treatment" and "therapy" as used herein refer to curative therapy, prophylactic therapy, preventative therapy, and mitigating disease therapy.

The phrase "more aggressive dosing regimen" or "increased dosing frequency regimen", as used herein refers to a dosing regimen that necessarily exceeds the basal and/or prescribed dosing regimen of either the anti-CS1 agent arm of the dosing regimen, either due to an increased dosing frequency (about once a week, about bi-weekly, about once daily, about twice daily, etc.), increased or escalated dose (in the case of the anti-CS1 antibody: about 11, about 12, about 13, about 14, about 15, about 16, about 17, about 18, about 19, about 20, about 21, about 22, about 23, about 24, about 25, about 26, about 27, about 28, about 29, about 30, about 35, about 40 mg/kg, or by changing the route of administration which may result in an increased, bio-available level of said anti-CS1 agent and/or pomalidomide.

It is to be understood this invention is not limited to particular methods, reagents, compounds, compositions, or biological systems, which can, of course, vary. It is also to be understood that the terminology used herein is for the purpose of describing particular aspects only, and is not intended to be limiting.

As used in this specification and the appended claims, the singular forms "a", "an", and "the" include plural referents unless the content clearly dictates otherwise. Thus, for example, reference to "a peptide" includes a combination of two or more peptides, and the like.

"About" as used herein when referring to a measurable value such as an amount, a temporal duration, and the like, is meant to encompass variations of ±20% or ±10%, preferably ±5%, or ±1%, or as little as ±0.1% from the specified value, as such variations are appropriate to perform the disclosed methods, unless otherwise specified herein.

As used herein, the terms CS1, SLAMF7, SLAM Family Member 7, CD2 Subset, CRACC, CD2-Like Receptor-Activating Cytotoxic Cells, 19A24 Protein, 19A, CD2-Like Receptor Activating Cytotoxic Cells, CD319, Novel LY9

(Lymphocyte Antigen 9) Like Protein, Membrane Protein FOAP-12, CD319 Antigen, Protein 19A, APEX-1, FOAP12, and Novel Ly93 are used interchangeably, and include variants, isoforms, species homologs of human CS1, and analogs having at least one common epitope with CS1.

CS1 is a cell surface glycoprotein that is highly expressed on Multiple Myeloma cells. CS1 is characterized by two extracellular immunoglobulin (Ig)-like domains and an intracellular signaling domain with immune receptor tyrosine-based switch motifs (Tai, Y.-T. et al., *Blood*, 113(18): 4309-4318 (Apr. 30, 2009); Bhat, R. et al., *J. Leukoc. Biol.*, 79:417-424 (2006); Fischer, A. et al., *Curr. Opin. Immunol.*, 19:348-353 (2007); Boles, K. S. et al., *Immunogenetics*, 52:302-307 (2001); Lee, J. K. et al., *J. Immunol.*, 179:4672-4678 (2007); and Veillette, A., *Immunol. Rev.*, 214:22-34 (2006)). CS1 is expressed at high levels in normal and malignant plasma cells, but not normal organs, solid tumors, or CD34$^+$ stem cells. Only a small subset of resting lymphocytes, including NK cells and a subset of CD8$^+$ T cells, express detectable but low levels of CS1 (His, E. D. et al., *Clin. Cancer Res.*, 14:2775-2784 (2008) and Murphy, J. J. et al., *Biochem. J.*, 361:431-436 (2002)).

CS1 was isolated and cloned by Boles et al. (*Immunogenetics*, 52(3-4):302-307 (2001)). The complete CS1 sequence can be found under GENBANK® Accession No. NM_021181.3 and is as follows:

```
                                          (SEQ ID NO: 5)
MAGSPTCLTLIYILWQLTGSAASGPVKELVGSVGGAVTFPLKSKVKQVDS

IVWTFNTTPLVTIQPEGGTIIVTQNRNRERVDFPDGGYSLKLSKLKKNDS

GIYYVGIYSSSLQQPSTQEYVLHVYEHLSKPKVTMGLQSNKNGTCVTNLT

CCMEHGEEDVIYTWKALGQAANESHNGSILPISWRWGESDMTFICVARNP

VSRNFSSPILARKLCEGAADDPDSSMVLLCLLLVPLLLSLFVLGLFLWFL

KRERQEEYIEEKKRVDICRETPNICPHSGENTEYDTIPHTNRTILKEDPA

NTVYSTVEIPKKMENPHSLLTMPDTPRLFAYENV
```

Specific therapeutic dosing regimens for any given patient may be established based upon the specific disease for which the patient has been diagnosed, or in conjunction with the stage of the patient's disease. For example, if a patient is diagnosed with a less-aggressive cancer, or a cancer that is in its early stages, the patient may have an increased likelihood of achieving a clinical benefit and/or immune-related response to a concurrent administration of an anti-CS1 agent followed by pomalidomide and/or a sequential administration of an anti-CS1 agent followed by pomalidomide. Alternatively, if a patient is diagnosed with a more-aggressive cancer, or a cancer that is in its later stages, the patient may have a decreased likelihood of achieving a clinical benefit and/or immune-related response to said concurrent and/or sequential administration, and thus may suggest that either higher doses of said anti-CS1 agent and/or said pomalidomide therapy should be administered or more aggressive dosing regimens or either agent or combination therapy may be warranted. In one aspect, an increased dosing level of a anti-CS1 antibody, such as Elotuzumab, would be about 10%, 20%, 30%, 40%, 50%, 60%, 70%, 80%, 90%, or 95% more than the typical anti-CS1 agent dose for a particular indication or individual (e.g., about 0.3 mg/kg, about 1 mg/kg, about 3 mg/kg, about 10 mg/kg, about 15 mg/kg, about 20 mg/kg, about 25 mg/kg, about 30 mg/kg), or about 1.5×, 2×, 2.5×, 3×, 3.5×, 4×, 4.5×, 5×, 6×, 7×, 8×, 9×, or 10× more anti-CS1 agent than the typical dose for a particular indication or for individual. In another aspect, an increased dosing level of pomalidomide would be about 10%, 20%, 30%, 40%, 50%, 60%, 70%, 80%, 90%, or 95% more than the typical pomalidomide dose for a particular indication or individual (e.g., about 1 mg, about 2 mg, about 3 mg, about 4 mg, about 5 mg, about 6 mg), or about 1.5×, 2×, 2.5×, 3×, 3.5×, 4×, 4.5×, 5×, 6×, 7×, 8×, 9×, or 10× more pomalidomide than the typical dose for a particular indication or for individual.

In another aspect, the synergistic combination may permit using a lower dose of either pomalidomide and/or an anti-CS1 antibody, relative to the typical prescribed doses. For example, a decreased dosing level of an anti-CS1 antibody, such as Elotuzumab, would be about 10%, 20%, 30%, 40%, 50%, 60%, 70%, 80%, 90%, or 95% less than the typical anti-CS1 agent dose for a particular indication or individual (e.g., about 0.3 mg/kg, about 1 mg/kg, about 3 mg/kg, or about 10 mg/kg), or about 1.5×, 2×, 2.5×, 3×, 3.5×, 4×, 4.5×, 5×, 6×, 7×, 8×, 9×, or 10× less anti-CS1 agent than the typical dose for a particular indication or for individual. In another aspect, a decreased dosing level of pomalidomide would be about 10%, 20%, 30%, 40%, 50%, 60%, 70%, 80%, 90%, or 95% less than the typical pomalidomide dose for a particular indication or individual (e.g., about 0.1 mg/kg, 0.5 mg/kg, 1 mg, about 2 mg, or about 3 mg), or about 1.5×, 2×, 2.5×, 3×, 3.5×, 4×, 4.5×, 5×, 6×, 7×, 8×, 9×, or 10× less pomalidomide than the typical dose for a particular indication or for individual.

Alternatively, in the event a patient fails to achieve a favorable response to the combination of an anti-CS1 antibody (e.g., Elotuzumab) and pomalidomide, and optionally including dexamethasone, the present invention encompasses the addition of a proteosome inhibitor such as bortezomib or another proteosome inhibitor, such as Carfilzomib, Ixazomib, or Oprozomib. If bortezomib, the recommended dose is 1.3 mg/m$^2$ administered as a 3 to 5 second bolus IV.

A therapeutically effective amount of an anti-CS1 agent and/or pomalidomide, can be orally administered if it is a small molecule modulator, for example, or preferably injected into the patient, for example, if it is a biologic agent. The actual dosage employed can be varied depending upon the requirements of the patient and the severity of the condition being treated. Determination of the proper starting dosage for a particular situation is within the skill of the art, though the assignment of a treatment regimen will benefit from taking into consideration the indication and the stage of the disease. Nonetheless, it will be understood that the specific dose level and frequency of dosing for any particular patient can be varied and will depend upon a variety of factors including the activity of the specific compound employed, the metabolic stability and length of action of that compound, the species, age, body weight, general health, sex and diet of the patient, the mode and time of administration, rate of excretion, drug combination, and severity of the particular condition. Preferred patients for treatment include animals, most preferably mammalian species such as humans, and domestic animals such as dogs, cats, and the like, patient to cancer.

As used herein, the terms "induction" and "induction phase" are used interchangeably and refer to the first phase of treatment in the clinical trial. For example, during induction, subjects may receive intravenous doses of an pomalidomide in combination with an anti-CS1 antibody.

As used herein, the terms "maintenance" and "maintenance phase" are used interchangeably and refer to the second phase of treatment in the clinical trial. For example, during maintenance, subjects may receive an agonistic CD137 in combination with an anti-CS1 antibody. In certain embodiments, treatment is continued as long as clinical benefit is observed or until unmanageable toxicity or disease progression occurs.

As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., pomalidomide and/or anti-CS1 antibody).

As used herein, a "body surface area (BSA)-based dose" refers to a dose (e.g., of pomalidomide and/or anti-CS1 antibody) that is adjusted to the body-surface area (BSA) of the individual patient. A BSA-based dose may be provided as mg/kg body weight. Various calculations have been published to arrive at the BSA without direct measurement, the most widely used of which is the Du Bois formula (see Du Bois, D. et al., Arch. Intern. Med., 17(6):863-871 (June 1916); and Verbraecken, J. et al., Metabolism—Clinical and Experimental, 55(4):515-514 (April 2006)). Other exemplary BSA formulas include the Mosteller formula (Mosteller, R D., N Engl. J. Med., 317:1098 (1987)), the Haycock formula (Haycock, G. B. et al., J. Pediatr., 93:62-66 (1978)), the Gehan and George formula (Gehan, E. A. et al., Cancer Chemother. Rep., 54:225-235 (1970)), the Boyd formula (Current, J. D., The Internet Journal of Anesthesiology, 2(2) (1998); and Boyd, E., University of Minnesota, The Institute of Child Welfare, Monograph Series, No. 10, Oxford University Press, London (1935)), the Fujimoto formula (Fujimoto, S. et al., Nippon Eiseigaku Zasshi, 5:443-450 (1968)), the Takahira formula (Fujimoto, S. et al., Nippon Eiseigaku Zasshi, 5:443-450 (1968)), and the Schlich formula (Schlich, E. et al., Ernährungs Umschau, 57:178-183 (2010)).

The terms "combination" and "combinations" as used herein refer to combination of an anti-CS1 antibody with pomalidomide, the combination of an anti-CS1 antibody with pomalidomide and dexamethasone, the concurrent administration of an anti-CS1 agent and pomalidomide optionally with dexamethasone; or to the sequential administration of an anti-CS1 agent with pomalidomide optionally with dexamethasone; or to a more complex, combination, which may include for example, the combination of either an anti-CS1 agent and/or pomalidomide with another agent, such as an immunotherapeutic agent or co-stimulatory pathway modulator, preferably an agonist (i.e., immunostimulant), PROVENGE®, a tubulin stabilizing agent (e.g., pacitaxol, epothilone, taxane, etc.), Bevacizumab, IXEMPRA®, Dacarbazine, PARAPLATIN®, Docetaxel, one or more peptide vaccines, MDX-1379 Melanoma Peptide Vaccine, one or more gp100 peptide vaccine, fowlpox-PSA-TRICOM™ vaccine, vaccinia-PSA-TRICOM™ vaccine, MART-1 antigen, sargramostim, ticilimumab, Combination Androgen Ablative Therapy; the combination with a co-stimulatory pathway modulator; the combination with a tubulin stabilizing agent (e.g., pacitaxol, epothilone, taxane, etc.); the combination with IXEMPRA®, the combination with Dacarbazine, the combination with PARAPLATIN®, the combination of Ipilimumab with Docetaxel, the combination with one or more peptide vaccines, the combination with MDX-1379 Melanoma Peptide Vaccine, the combination with one or more gp100 peptide vaccine, the combination with fowlpox-PSA-TRICOM™ vaccine, the combination with vaccinia-PSA-TRICOM™ vaccine, the combination with MART-1 antigen, the combination with sargramostim, the combination with ticilimumab, and/or the combination with Combination Androgen Ablative Therapy. The combinations of the present invention may also be used in conjunction with other well known therapies that are selected for their particular usefulness against the condition that is being treated. Such combinations may provide therapeutic options to those patients who present with more aggressive indications.

In another embodiment of the present invention, the combination between pomalidomide and/or anti-CS1 agent, and at least one other agent may comprise the following: agatolimod, belatacept, blinatumomab, CD40 ligand, anti-B7-1 antibody, anti-B7-2 antibody, anti-B7-H4 antibody, AG4263, eritoran, anti-CD137 monoclonal antibodies, anti-OX40 antibody, ISF-154, and SGN-70.

In another embodiment of the present invention, the combination between pomalidomide and/or anti-CS1 agent, and at least one other agent may comprise a chemotherapeutic agent.

A variety of chemotherapeutics are known in the art, some of which are described herein. One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromatase inhibitors, bifunctional alkylating agents, etc.

In another embodiment of the present invention, the chemotherapeutic agent may comprise microtubule-stabilizing agents, such as ixabepilone (IXEMPRA®) and paclitaxel (TAXOL®), which commonly are used for the treatment of many types of cancer and represent an attractive class of agents to combine with CTLA-4 blockade.

The phrase "microtubulin modulating agent" is meant to refer to agents that either stabilize microtubulin or destabilize microtubulin synthesis and/or polymerization.

One microtubulin modulating agent is paclitaxel (marketed as TAXOL®), which is known to cause mitotic abnormalities and arrest, and promotes microtubule assembly into calcium-stable aggregated structures resulting in inhibition of cell replication.

Epothilones mimic the biological effects of TAXOL®, (Bollag et al., Cancer Res., 55:2325-2333 (1995), and in competition studies act as competitive inhibitors of TAXOL® binding to microtubules. However, epothilones enjoy a significant advantage over TAXOL® in that epothilones exhibit a much lower drop in potency compared to TAXOL® against a multiple drug-resistant cell line (Bollag et al. (1995)). Furthermore, epothilones are considerably less efficiently exported from the cells by P-glycoprotein than is TAXOL® (Gerth et al. (1996)). Additional examples of epothilones are provided in co-owned, PCT Application No. PCT/US2009/030291, filed Jan. 7, 2009, which is hereby incorporated by reference herein in its entirety for all purposes.

Ixabepilone is a semi-synthetic lactam analogue of patupilone that binds to tubulin and promotes tubulin polymerization and microtubule stabilization, thereby arresting cells in the G2/M phase of the cell cycle and inducing tumor cell apoptosis.

Additional examples of microtubule modulating agents useful in combination with immunotherapy include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E),7R*,10S*, 11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in U.S. Pat. No. 6,262,094, issued Jul. 17, 2001), [1S-[1R*, 3R*(E),7R*,10S*,11R*,12R*,16S*]]-3-[2-[2-(aminomethyl)-4-thiazolyl]-1-methylethenyl]-7,11-dihydroxy-8,8, 10,12,16-pentamethyl-4-17-dioxabicyclo[14.1.0]-heptadecane-5,9-dione (disclosed in U.S. patent application Ser. No. 09/506,481 filed on Feb. 17, 2000, and Examples 7 and 8 herein), and derivatives thereof; and other microtubule-disruptor agents. Additional antineoplastic agents include, discodermolide (see Service, Science, 274:2009 (1996)) estramustine, nocodazole, MAP4, and the like. Examples of such agents are also described in the scientific and patent literature, see, e.g., Bulinski, *J. Cell Sci.*, 110: 3055-3064 (1997); Panda, *Proc. Natl. Acad. Sci. USA*, 94:10560-10564 (1997); Muhlradt, *Cancer Res.*, 57:3344-3346 (1997); Nicolaou, *Nature*, 387:268-272 (1997); Vasquez, *Mol. Biol. Cell.*, 8:973-985 (1997); and Panda, *J. Biol. Chem.*, 271:29807-29812 (1996).

The following sets forth preferred therapeutic combinations and exemplary dosages for use in the methods of the present invention.

| Therapeutic Combination(s) | Dosage mg/kg (per dose) |
|---|---|
| Anti-CS1 antibody + | 1-20 mg/kg |
| Pomalidomide | 1-4 mg Oral |
| Anti-CS1 antibody + | 10 mg/kg |
| Pomalidomide | 4 mg Oral |
| Anti-CS1 antibody+ | 10 mg/kg |
| Pomalidomide + | 4 mg Oral |
| Dexamethasone | 28 mg Oral |
| Anti-CS1 antibody + | 10 mg/kg |
| Pomalidomide + | 4 mg Oral |
| Dexamethasone | 40 mg Oral |
| Anti-CS1 antibody + | 10 mg/kg |
| Pomalidomide + | 4 mg/kg Oral |
| Dexamethasone | 8 mg IV |

While this table provides exemplary dosage ranges of the anti-CS1, pomalidomide, and dexamethasone, when formulating the pharmaceutical compositions of the invention the clinician may utilize preferred dosages as warranted by the condition of the patient being treated. For example, elotuzumab may preferably be administered at about 10 mg/kg every 3 weeks. Pomalidomide may preferably be administered at about 1 mg, 2 mg, 3 mg, or 4 mg, every three weeks. Dexamethasone may be administered 28 mg or 40 mg orally, or 8 mg via IV.

The anti-CS1 antibody may preferably be administered at about 0.1-20 mg/kg, or the maximum tolerated dose. In an embodiment of the invention, a dosage of anti-CS1 antibody is administered about every three weeks. Alternatively, the anti-CS1 antibody may be administered by an escalating dosage regimen including administering a first dosage of anti-CS1 antibody at about 1 mg/kg, a second dosage of anti-CS1 antibody at about 3 mg/kg, and a third dosage of anti-CS1 antibody at about 10 mg/kg.

In another specific embodiment, the escalating dosage regimen includes administering a first dosage of anti-CS1 antibody at about 3 mg/kg and a second dosage of anti-CS1 antibody at about 10 mg/kg.

Pomalidomide may preferably be administered at about 1-4 mg, or the maximum tolerated dose. In an embodiment of the invention, a dosage of pomalidomide is administered daily. Alternatively, pomalidomide may be administered by an escalating dosage regimen including administering a first dosage of pomalidomide at about 1 mg, a second dosage of pomalidomide at about 2 mg, a third dosage of pomalidomide at about 3 mg, and a fourth or subsequent dosages pomalidomide at about 4 mg.

In another specific embodiment, the escalating dosage regimen includes administering a first dosage of pomalidomide at about 1 mg and a second dosage of pomalidomide at about 3 mg.

In another specific embodiment, the escalating dosage regimen includes administering a first dosage of pomalidomide at about 3 mg and a second dosage of pomalidomide at about 4 mg.

Further, the present invention provides an escalating dosage regimen, which includes administering an increasing dosage of anti-CS1 antibody about every six weeks.

In one embodiment, the anti-CS1 antibody is administered on (1) day 1, week 1, (2) day 1, week 2, (3) day 1, week 3, (4) day 1, week 4, (5) day 1, week 5, (6) day 1, week 6, (7) day 1, week 7, and (8) day 1, week 8, of the induction phase. In another embodiment, pomalidomide is administered on (1) day 1, week 1, (2) day 1, week 4, and (3) day 1, week 7 of the induction phase. In another embodiment, the anti-CS1 antibody is administered on (1) day 1, week 10 and (2) day 1, week 15 of the maintenance phase. In another embodiment, pomalidomide is administered on (1) day 1, week 10 of the maintenance phase. In another embodiment, the maintenance phase is repeated for at least 1, 2, 3, 4, 5, 6, 7, 8, 9, 10, 11, 12, 13, 14, 15, 16, 17, 18, 19, or 20 or more cycles.

The actual dosage employed may be varied depending upon the requirements of the patient and the severity of the condition being treated. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

In practicing the many aspects of the invention herein, biological samples can be selected preferably from blood, blood cells (red blood cells or white blood cells). Cells from a sample can be used, or a lysate of a cell sample can be used. In certain embodiments, the biological sample comprises blood cells.

Pharmaceutical compositions for use in the present invention can include compositions comprising one or a combination of co-stimulatory pathway modulators in an effective amount to achieve the intended purpose. A therapeutically effective dose refers to that amount of active ingredient which ameliorates the symptoms or condition. Therapeutic efficacy and toxicity in humans can be predicted by standard pharmaceutical procedures in cell cultures or experimental animals, for example, the ED50 (the dose therapeutically effective in 50% of the population) and LD50 (the dose lethal to 50% of the population).

A "therapeutically effective amount" of an anti-CS1 agent may range anywhere from 1 to 14 fold or more higher than the typical dose depending upon the patients indication and severity of disease. Accordingly, therapeutically relevant doses of an anti-CS1 agent for any disorder disclosed herein can be, for example, about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 225, 250, or 300 fold higher than the prescribed or standard dose. Alternatively, therapeutically relevant doses of an anti-CS1 agent can be, for example, about 1.0×, about 0.9×, 0.8×, 0.7×, 0.6×, 0.5×, 0.4×, 0.3×, 0.2×, 0.1×, 0.09×, 0.08×, 0.07×, 0.06×, 0.05×, 0.04×, 0.03×, 0.02×, or 0.01× higher than the prescribed dose.

A "therapeutically effective amount" of an anti-CS1 agent may range anywhere from 1 to 14 fold or more lower than the typical dose depending upon the patients indication and severity of disease. Accordingly, therapeutically relevant doses of an anti-CS1 agent for any disorder disclosed herein can be, for example, about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 225, 250, or 300 fold lower than the prescribed or standard dose. Alternatively, therapeutically relevant doses of an anti-CS1 agent can be, for example, about 1.0×, about 0.9×, 0.8×, 0.7×, 0.6×, 0.5×, 0.4×, 0.3×, 0.2×, 0.1×, 0.09×, 0.08×, 0.07×, 0.06×, 0.05×, 0.04×, 0.03×, 0.02×, or 0.01× lower than the prescribed dose.

A "therapeutically effective amount" of pomalidomide may range anywhere from 1 to 14 fold or more higher than the typical dose depending upon the patients indication and severity of disease. Accordingly, therapeutically relevant doses of pomalidomide for any disorder disclosed herein can be, for example, about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 225, 250, or 300 fold higher than the prescribed or standard dose. Alternatively, therapeutically relevant doses of pomalidomide can be, for example, about 1.0×, about 0.9×, 0.8×, 0.7×, 0.6×, 0.5×, 0.4×, 0.3×, 0.2×, 0.1×, 0.09×, 0.08×, 0.07×, 0.06×, 0.05×, 0.04×, 0.03×, 0.02×, or 0.01× higher than the prescribed dose.

A "therapeutically effective amount" of pomalidomide may range anywhere from 1 to 14 fold or more lower than the typical dose depending upon the patients indication and severity of disease. Accordingly, therapeutically relevant doses of pomalidomide for any disorder disclosed herein can be, for example, about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 225, 250, or 300 fold lower than the prescribed or standard dose. Alternatively, therapeutically relevant doses of pomalidomide can be, for example, about 1.0×, about 0.9×, 0.8×, 0.7×, 0.6×, 0.5×, 0.4×, 0.3×, 0.2×, 0.1×, 0.09×, 0.08×, 0.07×, 0.06×, 0.05×, 0.04×, 0.03×, 0.02×, or 0.01× lower than the prescribed dose.

For combinations encompassing the addition of dexamethasone, it would be within the skill of the prescribing physician to provide a recommended dose for treatment. Suggested doses for low-dose dexamethasone include: 28 mg once daily, and when administered as part of a 1 month cycle, administering low-dose dexamethasone on days 1, 8, 15, 22 (for cycles 1 & 2); on days 1 & 15 (cycles 3-18); and day 1 (cycle 19 & beyond). Suggested doses for high-dose dexamethasone include: 40 mg once daily, and when administered as part of a 1 month cycle, administering low-dose dexamethasone on days 8 and 22 (for cycles 3 to 18); and on days 8, 15, and 22 (cycles 19 and beyond). Suggested doses for IV dexamethasone include: 8 mg IV once daily, and when administered as part of a 1 month cycle, administering IV dexamethasone on days 1, 8 15 and 22 (for cycles 1 and 2); on days 1 and 15 (cycles 3 to 18) and on day 1 (cycles 19 and beyond).

Disorders for which the sequential dosing regimen may be useful in treating includes one or more of the following disorders: melanoma, prostate cancer, and lung cancer, for example, also include leukemias, including, for example, chronic myeloid leukemia (CML), acute lymphoblastic leukemia, and Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia, chronic lymphocytic leukemia, mastocytosis and any symptom associated with mastocytosis. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia. Various additional cancers are also included within the scope of protein tyrosine kinase-associated disorders including, for example, the following: carcinoma, including that of the bladder, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma. In certain preferred embodiments, the disorder is leukemia, breast cancer, prostate cancer, lung cancer, colon cancer, melanoma, or solid tumors. In certain preferred embodiments, the leukemia is chronic myeloid leukemia (CML), Ph+ ALL, AML, imatinib-resistant CML, imatinib-intolerant CML, accelerated CML, lymphoid blast phase CML.

The terms "cancer", "cancerous", or "malignant" refer to or describe the physiological condition in mammals, or other organisms, that is typically characterized by unregulated cell growth. Examples of cancer include, for example, solid tumors, melanoma, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

A "solid tumor" includes, for example, sarcoma, melanoma, colon carcinoma, breast carcinoma, prostate carcinoma, or other solid tumor cancer.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

Provided herein are methods for treating cancer (e.g., hematological cancers, including Multiple Myeloma) in a patient comprising administering to the patient an anti-CS1 antibody and an agonistic CD137. Preferably, the combination therapy exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (Corbett, T. H. et al., *Cancer Treat. Rep.*, 66:1187 (1982)). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. Accordingly, in one embodiment, administration of anti-CS1 antibody, pomalidomide with or without dexamethasone, has at least an additive, and in some cases (with dexamethasone) a synergistic effect on treatment compared to administration of either therapy alone.

Alternatively, the combination therapy of an anti-CS1 antibody and an agonistic CD137 may have an additive or superadditive effect on suppressing cancer (e.g., Multiple Myeloma), as compared to monotherapy with either antibody alone. By "additive" is meant a result that is greater in extent than the best separate result achieved by monotherapy with each individual component, while "superadditive" is used to indicate a result that exceeds in extent the sum of such separate results (e.g., synergistic). In one embodiment, the additive effect is measured as, e.g., reduction in paraproteins, reduction in M-protein, reduction of plasmacytosis, reduction of bone lesions over time, increase in overall response rate, or increase in median or overall survival.

Multiple Myeloma disease response or progression, in particular, is typically measured according to the size of reduction (or rise) in paraproteins. However, the degree of plasmacytosis in the bone marrow (increase in percentage of plasma cells in the bone marrow), progression of bone lesions, and the existence of soft tissue plasmacytomas (a malignant plasma cell tumor growing within soft tissue) are also considered (Smith, D. et al., *BMJ*, 346:f3863 (Jun. 26, 2013)). Responses to therapy may include:

---

Complete Response
No detectable paraprotein and disappearance of any soft tissue plasmacytomas and <5% plasma cells in bone marrow.
Very Good Partial Response
Greater than 90% reduction in paraproteins or paraproteins detectable but too low to measure.
Partial Response
Greater than 50% reduction in paraproteins.
No Change or Stable Disease
Not meeting criteria for disease response or progression.
Progressive Disease
At least a 25% increase in paraproteins (increase of at least 5 g/L), development of new bone lesions or plasmacytomas, or hypercalcaemia. (corrected serum calcium >2.65 mmol/L)

---

Patients treated according to the methods disclosed herein preferably experience improvement in at least one sign of Multiple Myeloma. In one embodiment, the patient treated exhibits a complete response (CR), a very good partial response (VGPR), a partial response (PR), or stable disease (SD).

In one embodiment, improvement is measured by a reduction in paraprotein and/or decrease or disappearance of soft tissue plasmacytomas. In another embodiment, lesions can be measured by radiography. In another embodiment, cytology or histology can be used to evaluate responsiveness to a therapy.

In other embodiments, administration of effective amounts of pomalidomide and anti-CS1 antibody, with or without dexamethasone, according to any of the methods provided herein produces at least one therapeutic effect selected from the group consisting of reduction in paraprotein, M-protein reduction, decrease or disappearance of soft tissue plasmacytomas, CR, VGPR, PR, or SD. In still other embodiments, the methods of treatment produce a comparable clinical benefit rate (CBR=CR+PR+SD≥6 months) better than that achieved by pomalidomide or anti-CS1 antibody alone (particular when dexamethasone is added). In other embodiments, the improvement of clinical benefit rate is about 10% 20%, 30%, 40%, 50%, 60%, 70%, 80% or more compared to pomalidomide or anti-CS1 antibody alone (particular when dexamethasone is added).

Antibodies

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, AFFIBODY®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

Antibodies also include known forms of antibodies. For example, the antibody can be a human antibody, a humanized antibody, a bispecific antibody, or a chimeric antibody. The antibody also can be a Fab, Fab'2, ScFv, SMIP, AFFIBODY®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

The concurrent dosing regimen of the present invention may include the use of antibodies as one component of the combination. For example, antibodies that specifically bind to CS-1 polypeptides, preferably Elotuzumab.

The term "antibody" is also used in the broadest sense and specifically covers monoclonal antibodies, polyclonal antibodies, antibody compositions with polyepitopic specificity, bispecific antibodies, diabodies, chimeric, single-chain, and humanized antibodies, as well as antibody fragments (e.g., Fab, F(ab')2, and Fv), so long as they exhibit the desired biological activity. Antibodies can be labeled for use in biological assays (e.g., radioisotope labels, fluorescent labels) to aid in detection of the antibody.

Antibodies can be prepared using, for example, intact polypeptides or fragments containing small peptides of interest, which can be prepared recombinantly for use as the immunizing antigen. The polypeptide or oligopeptide used to immunize an animal can be derived from the translation of RNA or synthesized chemically, and can be conjugated to a carrier protein, if desired. Commonly used carriers that are chemically coupled to peptides include, for example, bovine serum albumin (BSA), keyhole limpet hemocyanin (KLH), and thyroglobulin. The coupled peptide is then used to immunize the animal (e.g., a mouse, a rat, or a rabbit).

The term "antigenic determinant" refers to that portion of a molecule that makes contact with a particular antibody (i.e., an epitope). When a protein or fragment of a protein is used to immunize a host animal, numerous regions of the protein can induce the production of antibodies that bind specifically to a given region or three-dimensional structure on the protein; each of these regions or structures is referred to as an antigenic determinant. An antigenic determinant can compete with the intact antigen (i.e., the immunogen used to elicit the immune response) for binding to an antibody.

The phrase "specifically binds to" refers to a binding reaction that is determinative of the presence of a target in the presence of a heterogeneous population of other biologics. Thus, under designated assay conditions, the specified binding region binds preferentially to a particular target and does not bind in a significant amount to other components present in a test sample. Specific binding to a target under such conditions can require a binding moiety that is selected for its specificity for a particular target. A variety of assay formats can be used to select binding regions that are specifically reactive with a particular analyte. Typically a specific or selective reaction will be at least twice background signal or noise and more typically more than 10 times background.

Anti-CS1 Antibodies

Anti-human-CS1 antibodies (or VH and/or VL domains derived therefrom) suitable for use in the invention can be generated using methods well known in the art. Alternatively, art recognized anti-CS1 antibodies can be used. For example, the monoclonal antibody mAb 162 described in Bouchon et al., J. Immunol., 167:5517-5521 (2001) can be used, the teachings of which are hereby incorporated by reference herein in their entirety, and in particular, those portions directly related to this antibody. Another known CS1 antibody includes the anti-CS1 antibody described in Matthew et al. (U.S. Pat. No. 7,041,499), the teachings of which are hereby incorporated by reference herein in their entirety, and in particular, those portions directly related to this antibody. Other known CS1 antibodies include the anti-CS1 antibody, Luc63 and other antibodies that share the same epitope, including Luc4, Luc12, Luc23, Luc29, Luc32 and Luc37, the anti-CS1 antibody Luc90 and other antibodies that share the same epitope, including Luc34, Luc69 and LucX, and the anti-CS1 antibodies Luc2, Luc3, Luc15, Luc22, Luc35, Luc38, Luc39, Luc56, Luc60, LucX.1, LucX.2, and PDL-241, described in Williams et al. (U.S. Pat. No. 7,709,610), the teachings of which are hereby incorporated by reference herein in their entirety, and in particular, those portions directly related to these antibodies. Antibodies that compete with any of these art-recognized antibodies for binding to CS1 also can be used.

An exemplary anti-CS1 antibody is elotuzumab (also referred to as BMS-901608 and HuLuc63) comprising heavy and light chains having the sequences shown in SEQ ID NOs:17 and 18, respectively, or antigen binding fragments and variants thereof. Elotuzumab is a humanized IgG anti-CS-1 monoclonal antibody described in PCT Publication Nos. WO 2004/100898, WO 2005/10238, WO 2008/019376, WO 2008/019378, WO 2008/019379, WO 2010/051391, WO 2011/053321, and WO 2011/053322, the teachings of which are hereby incorporated by reference. Elotuzumab is known to mediate ADCC through NK cells (van Rhee, F. et al., *Mol. Cancer Ther.*, 8(9):2616-2624 (2009)).

In other embodiments, the antibody comprises the heavy and light chain CDRs or variable regions of elotuzumab. Accordingly, in one embodiment, the antibody comprises the CDR1, CDR2, and CDR3 domains of the VH of elotuzumab having the sequence set forth in SEQ ID NO:2, and the CDR1, CDR2 and CDR3 domains of the VL of elotuzumab having the sequences set forth in SEQ ID NO:1. In another embodiment, the antibody comprises heavy chain CDR1 having amino acids 31-35 of SEQ ID NO:2: a heavy chain CDR2 having amino acids 50-66 of SEQ ID NO:2; and a heavy chain CDR3 having amino acids 99-108 of SEQ ID NO:2; in addition to a light chain CDR1 having amino acids 24-34 of SEQ ID NO:1; a light chain CDR2 having amino acids 50-56 of SEQ ID NO:1; and a light chain CDR3 having amino acids 89-97 of SEQ ID NO:1. In another embodiment, the antibody comprises VH and/or VL regions having the amino acid sequences set forth in SEQ ID NO: 2 and/or SEQ ID NO: 1, respectively. In another embodiment, the antibody competes for binding with and/or binds to the same epitope on CS1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO:2 or SEQ ID NO:1).

Kits

For use in the diagnostic and therapeutic applications described or suggested above, kits are also provided by the invention. Such kits can, for example, comprise a carrier means being compartmentalized to receive in close confinement one or more container means such as vials, tubes, and the like, each of the container means comprising one of the separate elements to be used in the method. For example, one of the container means can comprise one or more vials containing a pharmaceutically acceptable amount of an anti-CS1 antibody, and/or dexamethasone, with pomalidomide being administered separately; or an anti-CS1 antibody, and dexamethasone and pomalidomide being administered separately (oral or in the case of dexamethasone, IV in some cases).

The kit of the invention will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific therapy or non-therapeutic application, and can also indicate directions for either in vivo or in vitro use, such as those described above.

In addition, the kits can include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips, and the like), optical media (e.g., CD ROM), and the like. Such media can include addresses to internet sites that provide such instructional materials.

The kit can also comprise, for example, a means for obtaining a biological sample from an individual. Means for obtaining biological samples from individuals are well known in the art, e.g., catheters, syringes, and the like, and are not discussed herein in detail.

Also provided herein are kits which include a pharmaceutical composition containing pomalidomide, and an anti-CS1 antibody, such as elotuzumab, and/or dexamethasone, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a hematological cancer, such as Multiple Myeloma). The kit also can include a syringe.

Optionally, the kits include multiple packages of the single-dose pharmaceutical compositions each containing an effective amount of pomalidomide, an anti-CS1 antibody, and dexamethasone, for a single (separate) administration in accordance with the methods provided above. Instruments or devices necessary for administering the pharmaceutical composition(s) also may be included in the kits. For instance, a kit may provide one or more pre-filled syringes containing an amount of the anti-CS1 antibody and/or dexamethasone.

In one embodiment, the present invention provides a kit for treating a cancer (e.g., a hematological cancer, such as Multiple Myeloma) in a human patient, the kit comprising:
(a) a dose of an pomalidomide;
(b) a dose of an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1; and
(c) instructions for using pomalidomide and anti-CS1 antibody in the methods described herein.

In one embodiment, the present invention provides a kit for treating a cancer (e.g., a hematological cancer, such as Multiple Myeloma) in a human patient, the kit comprising:
(a) a dose of an pomalidomide;
(b) a dose of an anti-CS1 antibody comprising the CDR1, CDR2 and CDR3 domains in a heavy chain variable region comprising the sequence set forth in SEQ ID NO:2, and the CDR1, CDR2 and CDR3 domains in a light chain variable region comprising the sequence set forth in SEQ ID NO:1;
(c) a dose of dexamethasone (oral or IV); and
(c) instructions for using pomalidomide anti-CS1 antibody, and dexamethasone, in the methods described herein.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The following representative Examples contain important additional information, exemplification and guidance which can be adapted to the practice of this invention in its various embodiments and the equivalents thereof. These examples are intended to help illustrate the invention, and are not intended to, nor should they be construed to, limit its scope.

REFERENCES

1. Hsi, E. D. et al., "A potential new therapeutic antibody target for the treatment of multiple myeloma", *Clin. Cancer Res.*, 14:2775-2784 (2008).
2. Tai, Y. T. et al., "Anti-CS1 humanized monoclonal antibody HuLuc63 inhibits myeloma cell adhesion and induces antibody-dependent cellular cytotoxicity in the bone marrow milieu", *Blood,* 112:1329-1337 (2008).
3. Balasa, B. et al., "Elotuzumab enhances natural killer cell activation and myeloma cell killing through interleukin-2 and TNF-a pathways", *Cancer Immunol. Immunother.,* 64:61-73 (2015).
4. DeVita V T, Lawrence T S, and Rosenberg S A. Cancer: Principles and Practice of Oncology 9th edition. Chapter 136; pp 1999-1999. Wolters Kluwer/Lippincott, Williams, and Wilkins 2011.
5. International Myeloma Foundation. Concise Review of the Disease and Treatment Options 2008/2009 Edition.
6. Pratt, Guy. Histone deacetylase inhibitors in multiple myeloma. *The Lancet Oncology,* Volume 14, Issue 11, 1038-1039
7. Ludwig H, Beksac M, Blade J, et al. Current multiple myeloma treatment strategies with novel agents: a European perspective. *The Oncologist.* 2010; 15:6-25.
8. Jemal A, Marray T, Samuels A, Tiwari R C, Ghafoor, A, Thun M J. Cancer Statistics. *C A Cancer J Clin* 2005; 55: 10-50.
9. Kim J R, Horton N C, Mathew S O, Mathew P A. CS1 (SLAMF7) inhibits production of proinflammatory cytokines by activated monocytes. *Inflamm Res.* 2013 August; 62(8):765-72.
10. Cruz-Munoz M E, Dong Z, Shi X, Zhang S, Veillette A. Influence of CRACC, a SLAM family receptor coupled to the adaptor EAT-2, on natural killer cell function. *Nat Immunol.* 2009 March; 10(3):297-305. doi: 10.1038/ni.1693. Epub 2009 Jan. 18
11. PDL BioPharma, Inc.; RTR9 Research Technical Report: HuLuc63 binding to immune subsets in whole blood and bone marrow samples from multiple myeloma patients. Document Control No. 930045543.
12. Guo H, Cruz-Munoz M-E, Wu N, et al. *Immune cell inhibition by* SLAMF7 is mediated by mechanism requiring Src kinases, CD45 and SHIP-1 defective in multiple myeloma cells. *Mol Cell Biol.* 2015 January; 35(1):41-51.
13. Pérez-Quintero LA1, Roncagalli R, Guo H, et. al. EAT-2, a SAP-like adaptor, controls N K cell activation through phospholipase Cγ, Ca++, and Erk, leading to granule polarization. *J Exp Med.* 2014 Apr. 7; 211(4):727-42.
14. Xie Z, Gunaratne J, Cheong L L, et al. Plasma membrane proteomics identifies biomarkers associated with MMSET overexpression in T(4; 14) multiple myeloma. *Oncotarget.* 2013 July; 4(7):1008-18.
15. Glavey S, Reagan M, Manier S, et al. Dissecting the Mechanisms of Activity of SLAMF7 and the Targeting Antibody Elotuzumab in Multiple Myeloma. *Blood* 2014 124:3431; published ahead of print Dec. 5, 2014
16. Collins S M, Bakan C E, Swartzel G D, et. al. Elotuzumab directly enhances N K cell cytotoxicity against myeloma via CS1 ligation: evidence for augmented N K cell function complementing ADCC. *Cancer Immunol Immunother.* 2013 December; 62(12):1841-9.
17. Dornan D, Spleiss O, Yeh R F, Duchateau-Nguyen G, et al. Effect of FCGR2A and FCGR3A variants on CLL outcome. *Blood.* 2010 Nov. 18; 116(20):4212-22.
18. Weng W K, Levy R. Two immunoglobulin G fragment C receptor polymorphisms independently predict response to rituximab in patients with follicular lymphoma. *J Clin Oncol.* 2003 Nov. 1; 21(21):3940-7. Epub 2003 Sep. 15.
19. Hatjiharissi E, Xu L, Santos D D, Hunter Z R, et al. Increased natural killer cell expression of CD16, augmented binding and ADCC activity to rituximab among individuals expressing the FcgammaRIIIa-158 V/V and V/F polymorphism. *Blood.* 2007 Oct. 1; 110(7):2561-4. Epub 2007 May 2.
20. Tuscano J M, Dutia M, Chee K, Brunson A, et. al. Lenalidomide plus rituximab can produce durable clinical responses in patients with relapsed or refractory, indolent non-Hodgkin lymphoma. *Br J Haematol.* 2014 May; 165(3):375-81.
21. Investigator Brochure for Elotuzumab, BMS 901608, Version No.: 11, 2015
22. Jakubowiak A J, Benson D M, Bensinger W, et. al. Phase I Trial of Anti-CS1 Monoclonal Antibody Elotuzumab in Combination With Bortezomib in the Treatment of Relapsed/Refractory Multiple Myeloma. *J Clin Oncol.* 2012; 30(16):1960-1965.
23. Lonial S, Vij R, Harousseau J L, et al. Elotuzumab in combination with lenalidomide and low-dose dexamethasone in relapsed or refractory multiple myeloma. *J Clin Oncol.* 2012; 30(16):1953-1959.
24. Clinical Study Report HuLuc63-1701: Phase 1, multicenter, openlabel, dose escalation study of elotuzumab (humanized anti-CS1 monoclonal IgG1 antibody) in subjects with advanced multiple myeloma. Bristol-Myers Squibb Company; 2011. Document Control No. 930049616.
25. Richardson P D, Sonneveld P, Schuster M W et al. Bortezomib or highdose dexamethasone for relapsed multiple myeloma. *N Engl J Med* 2005; 352(24):2487-2498.
26. Richardson P G, Siegel D, Baz R, et al. Phase 1 study of pomalidomide MTD, safety, and efficacy in patients with refractory multiple myeloma who have received lenalidomide and bortezomib. *Blood.* 2013; 121(11):1961-1967.
27. Richardson P G, Siegel D S, Vij R, et al. Pomalidomide alone or in combination with lowdose dexamethasone in relapsed and refractory multiple myeloma: a randomized phase 2 study. *Blood.* 2014 Mar. 20; 123(12):1826-32
28. Lacy M Q, Allred J B, Gertz M A, et al. Pomalidomide plus low-dose dexamethasone in myeloma refractory to both bortezomib and lenalidomide: comparison of 2 dosing strategies in dual-refractory disease. *Blood.* 2011 Sep. 15; 118(11):2970-5
29. Martha Q. Lacy, M D, Betsy R. LaPlant, M S, Kristina M Laumann, B A, et al. Pomalidomide Plus Low-Dose Dexamethasone (Pom/Dex) in Relapsed Lenalidomide Refractory Myeloma: Long Term Follow up and Comparison of 2 Mg Vs 4 Mg Doses, ASH Abstract 4780, 2014
30. Katja Weisel, Meletios A Dimopoulos, Antonio Palumbo, et al. (Abstract, European Hematology Association, June 2015, P286). Analysis Of Patients With Refractory Or Relapsed And Refractory Multiple Myeloma And Renal Impairment Treated With Pomalidomide+Low-Dose Dexamethasone In The Phase 3b STRATUS Trial (MM-010)

31. Cruz-Munoz M E, Dong Z, Shi X, Zhang S, Veillette A. Influence of CRACC, a SLAM family receptor coupled to the adaptor EAT-2, on natural killer cell function. *Nat Immunol*. 2009 March; 10(3):297-305. doi: 10.1038/ni.1693. Epub 2009 Jan. 18.
32. Tai et al. Anti-CS1 humanized monoclonal antibody HuLuc63 inhibits myeloma cell adhesion and induces antibody-dependent cellular cytotoxicity in the bone marrow milieu. *Blood*. Aug. 15, 2008; 112(4): 1329-1337.
33. von Lilienfeld-Toal M1, Frank S, et al. Reduced immune effector cell NKG2D expression and increased levels of soluble NKG2D ligands in multiple myeloma may not be causally linked. *Cancer Immunol Immunother.* 2010 June; 59(6):829-39. doi: 10.1007/s00262-009-0807-3. Epub 2009 Dec. 19
34. Jinushi M, Vanneman M, Munshi N C, Tai Y T, Prabhala R H, Ritz J, Neuberg D, Anderson K C, Carrasco D R, Dranoff G. MHC class I chain-related protein A antibodies and shedding are associated with the progression of multiple myeloma. Proc *Natl Acad Sci USA*. 2008 Jan. 29; 105(4):1285-90.
35. David Dingli, Grzegorz S. Nowakowski, Angela Dispenzieri et. al. Flow cytometric detection of circulating myeloma cells before transplantation in patients with multiple myeloma: a simple risk stratification system. *Blood*. Apr. 15, 2006; 107(8): 3384-3388.
36. Steven Gross, Brad Foulk, Jaymala Patel, Mark Connelly, Marielena Mata. Automated Enumeration and Characterization of Circulating Multiple Myeloma Cells in Blood. Oral and Poster Abstracts, ASH. Session 651. Myeloma—Biology and Pathophysiology, excluding Therapy: Poster I
37. PDL BioPharma, Inc.; RTR12 Research Technical Report: HuLuc63 Cross-reactivity in human and non-human tissues using immunohistochemistry. Document Control No. 930046207
38. PDL BioPharma, Inc.; RTR21 Research Technical Report: HuLuc63 binding to immune subsets in whole blood samples of non-human primates. Document Control No. 930046209.
39. Glavey S, Reagan M, Manier S, et al. Dissecting the Mechanisms of Activity of SLAMF7 and the Targeting Antibody Elotuzumab in Multiple Myeloma. *Blood* 2014 124:3431; published ahead of print Dec. 5, 2014.
40. Paul G. Richardson, M D, Sundar Jagannath, M D, Philippe Moreau, M D et al. Final Results for the Phase 1b/2 Study of Elotuzumab in Combination with Lenalidomide and Dexamethasone in Patients with Relapsed/Refractory Multiple Myeloma. *American Society of Hematology Abstract*, 2014.
41. Lonial S, Jagannath S, Moreau P, et al. Phase (Ph) I/II study of elotuzumab (Elo) plus lenalidomide/dexamethasone (Len/dex) in relapsed/refractory multiple myeloma (RR MM): Updated Ph II results and Ph I/II long-term safety. *J Clin Oncol* 31, 2013 (suppl; abstr 8542)
42. Lonial S, Dimopoulos M, Palumbo A, et al. Elotuzumab Therapy for Relapsed or Refractory Multiple Myeloma. *N Engl J Med* 2015 Jun. 2. PMID: 26035255.
43. Rajkumar S V, Blood E, Vesole D, et al. Phase III clinical trial of thalidomide plus dexamethasone compared with dexamethasone alone in newly diagnosed multiple myeloma: A clinical trial coordinated by the Eastern Cooperative Oncology group. *J Clin Oncol* 2006; 24(3): 431-436
44. Rajkumar S V et al. Consensus recommendations for the uniform reporting of clinical trials: report of the International Myeloma Workshop Consensus Panel 1. *Blood*. 2011 May 5; 117(18):4691-5. doi: 10.1182/blood-2010-10-299487
45. Greipp P R, San Miguel J F, Brian G M, Durie J J, Crowley B B, Blade J, Boccadoro J, Child A, Avet-Loiseau H, Kyle R A, Laheuerta J J, Ludwig H, Morgan G, Powles R, Shimizu K, Shustik C, Sonneveld P, Tosi P, Turesson I, Westin J. International Staging System for Multiple Myeloma. *J Clin Oncology* 2005 23:3412-3420.
46. Durie B G, Harousseau J L, Miguel J S, Blade J, Barlogie B, Anderson K et al. International uniform response criteria for multiple myeloma. *Leukemia* 2006; 20: 2220.
47. Anderson K C, Kyle R A, Rajkumar S V, et al. *Leukemia* 2008; 231-239.
48. San Miguel J, Weisel K, Moreau P, Lacy M et al. Pomalidomide plus low-dose dexamethasone versus high-dose dexamethasone alone for patients with relapsed and refractory multiple myeloma (MM-003): a randomised, open-label, phase 3 trial. *Lancet Oncol*. 2013 October; 14(11):1055-66.
49. Meletios A. Dimopoulos, Martha Q Lacy, et al. Pomalidomide in Combination with Low-Dose Dexamethasone: Demonstrates a Significant Progression Free Survival and Overall Survival Advantage, in Relapsed/Refractory M M: A Phase 3, Multicenter, Randomized, Open-Label Study Blood (ASH Annual Meeting Abstracts), November 2012; 120: LBA-6.
50. Gorgun et al., Lenalidomide Enhances Immune Checkpoint Blockade-Induced Immune Response in Multiple Myeloma, *Clin Cancer Res*. 2015 Oct. 15; 21(20):4607-18.
51. Badros A., Kocoglu M., Ma N., Rapoport A., Lederer E., Philip S., Lesho P. D. C., Hardy N., Yared J., Goloubeva O., Singh Z. A phase II study of anti PD-1 antibody pembrolizumab, pomalidomide and dexamethasone in patients with relapsed/refractory multiple myeloma (RRMM) *Blood*. 2015; 126:506.

BRIEF DESCRIPTION OF THE SEQUENCE LISTING

Incorporated herein by reference in its entirety is a Sequence Listing entitled, "12585.US.PCT_ST25", comprising SEQ ID NO:1 through SEQ ID NO:5, which includes the nucleic acid and/or amino acid sequences disclosed herein. The Sequence Listing has been submitted herewith in ASCII text format via EFS. The Sequence Listing was first created on Jun. 17, 2015, and is 6 KB in size.

EXAMPLES

Example 1—Methods for Assessing the Therapeutic Effect of Combining an Anti-CS1 Antibody with Pomalidomide in an OMP-2 Multiple Myeloma Xenofraft Tumor Mouse Model—Study #1 OPM2-15

In vivo mouse studies have demonstrated that elotuzumab administered intraperitoneally (IP) inhibits tumor growth of human myeloma xenografts (Hsi et al., *Clin. Cancer Res.*, 14:2775-2784 (2008); and Tai et al., *Blood*, 112:1329-1337 (2008) in a dose-dependent fashion (Tai et al. (2008)). The anti-tumor activity of elotuzumab in xenograft models can be enhanced by co-administration with the small molecules, bortezomib (reversible inhibitor of the chymotrypsin-like activity of the 26S proteasome in mammalian cells) and lenalidomide (analogue of thalidomide with immunomodulatory, anti-angiogenic, and anti-neoplastic properties) (Balasa et al., *Cancer Immunol. Immunother.*, 64:61-73 (2015). In addition to lenalidomide, a second Imid, pomalidomide, is approved for MM treatment. Due to its direct anti-tumor activity dexamethasone is also used to treat MM, often in combination with other agents including lenalidomide. In this study the efficacy of pomalidomide treatment, both alone and in combination with elotuzumab and/or elotuzumab and dexamethasone, utilizing the OPM2 xenograft was assessed.

Pomalidomide treatment suppressed tumor growth in a dose-dependent fashion. Furthermore, the combination of pomalidomide and elotuzumab treatment was more efficacious than treatment with either of the agents alone.

Finally, the triple combination of elotuzumab, pomalidomide, and dexamethasone elicited complete tumor regressions in 8 of 16 the treated mice, and partial tumor regressions in 5 of 16 treated mice.

Methods

In Vivo Antitumor Activity

Animals: All mice were obtained from Taconic Biosciences (Germantown, N.Y.), and maintained in ammonia-free environment in a defined and pathogen-free colony. All animal procedures were approved by the Bristol-Myers Squibb (BMS) Institutional Animal Care and Use Committee. The animal care and use program at BMS has been fully accredited by the Association for Assessment and Accreditation of Laboratory Animal Care International (AAALAC).

Animal Models: The human tumor xenograft OPM2 was grown in IcrTac scid mice (ICRPrkdcscid). Treated animals were checked daily for treatment related toxicity/mortality. Each group of animals was weighed before the initiation of treatment (Wt1) and then weighed again following the last treatment dose (Wt2). The difference in body weight (Wt2-Wt1) provides a measure of treatment-related toxicity. Additional weights were recorded at each measurement date to monitor toxicity.

Tumor response was determined by measurement of tumors with a caliper twice a week, until the tumors reached a predetermined "target" size of 1 gm. Tumor weights (mg) were estimated from the formula: Tumor weight=(length×width2)/2.

Tumor response end-point was expressed in terms of tumor cell kill and tumor growth inhibition. Tumor growth delay was defined as the difference in time (days) required for the treated tumors (T) to reach a predetermined target size compared to those in the control group (C). For this purpose tumor weight of a group was expressed as medium tumor weight (MTW).

Tumor cell kill was expressed in terms of log cell kill (LCK), represented by the equation LCK=T-C/(3.32×TVDT) where tumor volume doubling time (TVDT) was first calculated with the formula: TVDT=Median time (days) for control tumor weight to reach target size−Median time (days) for control tumor weight to reach half the target size. To estimate tumor growth inhibition, tumor response was expressed in terms of percent tumor growth inhibition (% TGI) and calculated as follows: % Tumor Growth Inhibition={1−[(Tt−To)/(Ct−Co)]}×100, where Ct=Median control tumor size at end of treatment, Co=Median control tumor size at treatment initiation, Tt=Median tumor size of treated group at end of treatment, and To=Median tumor size of treated group at treatment initiation.

Definition of antitumor activity was dependent on the mode of drug action of the study agent in the tumor model under evaluation, i.e., cytotoxic versus cytostatic action. For cytotoxic effect, significant activity was defined as the attainment of tumor growth delay equivalent to >0.5 LCK or 1.7×TVDT. For cytostatic action, activity was defined as attainment of growth inhibition >70% TGI from one tumor volume doubling until the end of treatment.

Preparation of Tumor Cells: OPM2 cells were initially thawed on Jul. 28, 2014. Cells were previously tested for adventitious agents by polymerase chain reaction (PCR) and were negative. Cells were maintained RPMI (RPMI; Gibco, Cat. #11875-079) supplemented with 10% fetal bovine serum (FBS; Gibco, Cat. #26140-079). Cells displayed a doubling time of 48 hours. Approximately three times a week, cells contained in a single T150 flask were divided and expanded to two T150 flasks at a 1:2 dilution until sufficient number of cells were obtained for tumor implantation in 100 mice, 240 mice and 245 mice respectively. The cells were harvested while in log phase growth, washed and resuspended in HBSS to provide subcutaneous (SC) injections of 1×107 cells into the flank of each study animal.

Tumor Implantation: For Study #1, 240 mice were given a subcutaneous injection of 0.1 ml OPM2 cells at 1×108/ml with a 25 gauge needle on day 0. Tumors grew to the pre-determined size window, 48-200 mg (tumors outside the range were excluded) and animals were evenly distributed to various treatment and control groups with n=8 on day 16. For Study #2, 245 mice were given a subcutaneous injection of 0.1 ml OPM2 cells at 1×108/ml with a 25 gauge needle on day 0. Tumors grew to the pre-determined size window, 48-200 mg (tumors outside the range were excluded) and animals were evenly distributed to various treatment and control groups with n=8 on day 12.

Compound Preparation and Administration: For both studies Elotuzumab (ELO, BMS-901608) was prepared from a 25 mg/ml stock in phosphate buffered saline (PBS) for IP administration. Dosing regimen for elotuzumab was 2QW×5 or bi-weekly for 5 weeks for a total of 10 doses. Dexamethasone (DEX, MJ-006209; Bell Medical, Cat. #APP0165-30) was prepared from a 4 mg/ml stock in $H_2O$ for IP administration. Dosing regimen for dexamethasone was QD×7. A 10 mg/ml stock solution of Pomalidomide (POM, BMT-227758; Selleck Chem, Cat. #51567P0M) was prepared in 10% DMSO weekly and aliquoted for the required number of doses each week. Each dose was thawed and diluted daily in normal saline for PO administration. Dosing regimen for pomalidomide was QD×5; 16, 23 in Study #1 and QD×5; 12, 19 in Study #2. Specifically, on day 14 (post-tumor implantation for pomalidomide dose titration experiment), day 16 (post-tumor implantation for the first elotuzumab/pomalidomide/dexamethasone combination study, OPM2-15), or day 12 (post-tumor implantation for the second elotuzumab/pomalidomide/dexamethasone combination study, OPM2-16), each animal was treated as described. Treatment of each animal was based on individual body weight and the volume of all compounds administered was 0.01 ml/gm of mice. Dosing was discontinued if tumors reached target size prior to the completion of the dosing regimen.

Study Termination: Treatment groups were terminated when median tumor weight reached target size of 1 gm for two consecutive measurements. If the median tumor weight never reached target size, the treatment group was terminated when the remaining animals had stagnant tumor change for a period of >10 TVDT.

Statistical analysis: Statistical significance was determined using the non-parametric Mann-Whitney U Test, GraphPad Prism Version 4.00 for Windows (GraphPad Software, San Diego, Calif.).

Results

To assess the effect of pomalidomide treatment on the growth of the OPM2 xenograft, scid mice with established tumors were treated orally with pomalidomide at doses of 0.5 mg/kg, 5 mg/kg and 50 mg/kg. The data in FIG. 1 and Table 1 show treatment with pomalidomide inhibited tumor growth in a dose-dependent fashion. TGI values of 45%, 63.1%, and 87.1% were observed for the 0.5 mg/kg dose, the 5 mg/kg dose, and the 50 mg/kg dose, respectively (Table 1). From this experiment the suboptimal 5 mg/kg dose was chosen as the dose to use in the combination studies (Study #1, OPM2-15 and Study #2, OPM2-16).

TABLE 1

EFFICACY DOSE TITRATION OF POMALIDOMIDE IN OPM2 XENOGRAFT

| Treatment Group | Dose (mg/kg QD × 5; 14.21) | Median Days to target size | TGI[a] | LCK[b] | CR[c] | PR[d] | Weight Change % |
|---|---|---|---|---|---|---|---|
| 1 | Untreated Control | 23 | N/A | N/A | 0/8 | 0/8 | 4.7 |
| 2 | 50 | 33 | 87.1 | 1.0[e] | 0/8 | 1/8 | 4.7 |
| 3 | 5 | 29 | 63.1 | 0.59[f] | 0/8 | 0/8 | 3.2 |
| 4 | 0.5 | 25 | 45 | 0.19[g] | 0/8 | 0/8 | 9.3 |

Source ELN[6]
[a]Tumor growth inhibition
[b]Log cell kill
[c]Complete regression
[d]Partial regression
[e]P value versus untreated control: 0.0003
[f]P value versus untreated control: 0.0006
[g]P value versus untreated control: 0.0022

In the next set of studies (Study #1 OPM2-15), the combination treatments of elotuzumab, pomalidomide and dexamethasone on tumor growth were assessed. Scid mice with established OPM2 xenograft tumors were either untreated, treated with elotuzumab alone, treated with pomalidomide alone, treated with dexamethasone alone, treated with elotuzumab plus pomalidomide, treated with elotuzumab plus dexamethasone, treated with pomalidomide plus dexamethasone, or treated with elotuzumab plus pomalidomide plus dexamethasone. The data in FIG. 2 show tumor growth curves for all groups in Study #1 (OPM2-15) presented as means+/−standard deviation, and the data in FIG. 3 represent measured tumor volumes of all individual animals in each treatment group for Study #1. When compared to untreated mice, treatment with elotuzumab, pomalidomide or dexamethasone as single agents had TGI values of 70.3%, 52%, and 50.4%, respectively (Table 2). The combination of pomalidomide and elotuzumab demonstrated better efficacy than either of the agents alone (TGI=89.6%, Table 2). In addition, combination of pomalidomide and dexamethasone also demonstrated better efficacy than either of the agents alone (TGI=99.2%, Table 2). The triple combination of elotuzumab, pomalidomide, and dexamethasone elicited complete tumor regressions in 2 of the 8 of treated mice, and partial tumor regressions in 5 of the 8 treated mice (Table 2).

TABLE 2

ELOTUZUMAB EFFICACY IN COMBINATION WITH POMALIDOMIDE AND DEXAMETHASONE (STUDY #1, OPM2-15)

| Treatment Group | Dose (mg/kg) | Median Days to Target Size | TGI | LCK | CR | PR | % Weight Change | Max % Weight Loss[a] |
|---|---|---|---|---|---|---|---|---|
| Untreated Control | N/A | 25.9 | N/A | N/A | 0/8 | 0/8 | 1.3 | N/A |
| Elotuzumab (ELO) | 0.5[b] | 35.0 | 70.3 | 0.61 | 0/8 | 0/8 | 2.3 | −2.2 |
| Pomalidomide (POM) | 5[c] | 29.8 | 52 | 0.26 | 0/8 | 0/8 | −1.1 | −1.1 |
| Dexamethasone (DEX) | 5[d] | 28.0 | 50.4 | 0.14 | 0/8 | 0/8 | −4.0 | −5.7 |
| ELO + POM | 0.5 + 5 | 42.8 | 89.6 | 1.13[e] | 0/8 | 2/8 | −1.5 | −6.7 |
| ELO + DEX | 0.5 + 5 | 37.0 | 78.5 | 0.74[f] | 0/8 | 0/8 | 4.6 | −4.3 |
| POM + DEX | 5 + 5 | 40.5 | 99.2 | 0.98 | 0/8 | 1/8 | −8.0 | −8.0 |
| ELO + PMO + DEX | 0.5 + 5 + 5 | >100[g] | 106.7 | >4.97[h] | 2/8 | 5/8 | 2.7 | −7.2 |

Source ELN[7]
[a]Maximum weight loss recorded for that treatment group at any point during the study
[b]Elotuzumab dosing regimen is 2QW × 5; 16, twice a week for 5 weeks a total of 10 doses
[c]Dexamethasone dosing regimen is QD × 7; 16
[d]Pomalidomide dosing regimen is QD × 5; 16, 23
[e]P values: 0.0207 for ELO + POM vs. ELO and 0.03823 for ELO + POM vs. POM
[f]P values: 0.5969 for ELO + DEX vs. ELO and 0.0104 for ELO + DEX vs. DEX
[g]Study ended at day 100 with only 3/8 tumors reaching target size
[h]P values: 0.0002 for ELO + POM + DEX vs. POM + DEX Example 2—Methods for Assessing the Therapeutic Effect of Combining an Anti-CS1 Antibody with Pomalidomide in an OMP-2 Multiple Myeloma Xenofraft Tumor Mouse Model—Study #2 OPM2-16

The synergistic results observed in Study #1 OPM2-15 that is described in Example 1 were repeated. The materials and methods used in this set of experiments were identical to those described in Example 1 unless specified otherwise.

Results

The data presented in FIGS. 4A-B show tumor growth curves for all groups in Study #2 (OPM2-16) presented as means+/−standard deviation, and the data in FIGS. 5A-H represent measured tumor volumes of all individual animals in each treatment group for Study #2. In this study (OPM2-16), when compared to untreated mice, treatment with elotuzumab, pomalidomide, or dexamethasone as single agents had TGI values of 57.7%, 41.4%, and 62.8%, respectively (Table 3). The combination of pomalidomide and elotuzumab demonstrated better efficacy than either of the agents alone (TGI=72.5%, Table 3). In addition, combination of pomalidomide and dexamethasone also demonstrated better efficacy than either of the agents alone (TGI=88.3%, Table 3). Importantly, the triple combination of elotuzumab, pomalidomide, and dexamethasone elicited complete tumor regressions in 6 of the 8 of treated mice (Table 3).

In all of the studies, the treatments appeared well tolerated with no significant changes in body weights (Table 1, Table 2, Table 3) or overt signs of clinical toxicity observed indicating that the combinations were safe.

effect on tumor growth, but the combination of dexamethasone and pomalidomide treatment inhibited tumor growth better than either of the single agents alone. However, only the triple combination (elotuzumab plus pomalidomide plus dexamethasone) was synergistic and resulted in partial or complete tumor regressions. All of the treatments appeared well tolerated, with no significant changes in body weights or overt signs of clinical toxicity observed indicating that the combinations were safe at least on a superficial level.

Example 3—An Open Label, Randomized Phase 2 Trial Investigating the Combination of Pomalidomide/Dexamethasone with or without Elotuzumab in Relapsed and Refractory Multiple Myeloma Research Hypothesis The addition of elotuzumab to pomalidomide and dexamethasone (investigational combination therapy) will increase the progression free survival (PFS) in subjects with relapsed and refractory multiple myeloma Objectives The primary objective is to compare progression free survival (PFS) between treatment arms.

The secondary objective is to compare objective response rate between treatment arms as well as to compare overall survival between treatment arms.

Additional exploratory objectives are to evaluate the following: the safety and tolerability of the investigational combination therapy; the time to response and duration of response; the pharmacokinetics and immunogenicity of

TABLE 3

ELOTUZUMAB EFFICACY IN COMBINATION WITH POMALIDOMIDE AND DEXAMETHASONE IN OPM2 XENOGRAFT (STUDY #2 OPM2-16)

| Treatment Group | Dose (mg/kg) | Median Days to Target Size | TGI | LCK | CR | PR | % Weight Change | Max % Weight Loss[a] |
|---|---|---|---|---|---|---|---|---|
| Untreated Control | N/A | 19.1 | N/A | N/A | 0/8 | 0/8 | 15.0 | N/A |
| Elotuzumab (ELO) | 0.5[b] | 24.0 | 57.7 | 0.47 | 0/8 | 0/8 | 7.1 | N/A |
| Pomalidomide (POM) | 5[c] | 22.5 | 41.4 | 0.33 | 0/8 | 0/8 | 6.5 | −1.1 |
| Dexamethasone (DEX) | 5[d] | 25.7 | 62.8 | 0.63 | 0/8 | 0/8 | −9.0 | −9.0 |
| ELO + POM | 0.5 + 5 | 28.4 | 72.5 | 0.88[e] | 0/8 | 0/8 | 2.7 | −2.8 |
| ELO + DEX | 0.5 + 5 | 31.0 | 72.4 | 1.13[f] | 0/8 | 0/8 | 8.0 | −10.5 |
| POM + DEX | 5 + 5 | 34.4 | 88.3 | 1.47 | 0/8 | 0/8 | 1.9 | −9.4 |
| ELO + PMO + DEX | 0.5 + 5 + 5 | >75[g] | 105.4 | >5.3[h] | 6/8 | 0/8 | 4.6 | −10.1 |

Source ELN[8]
[a]Represents the maximum weight loss recorded for that treatment group at any point during the study
[b]Elotuzumab dosing regimen is 2QW × 5; 12, twice a week for 5 weeks a total of 10 doses
[c]Pomalidomide dosing regimen is QD × 5; 12, 19
[d]Dexamethasone dosing regimen is QD × 7; 12
[e]P values: 0.0404 for ELO + POM vs. ELO and 0.0047 for ELO + POM vs. POM
[f]P values: 0.258 for ELO + DEX vs. ELO and 0.0379 for ELO + DEX vs. DEX
[g]Study ended at day 75 with only 2/8 tumors reaching target size
[h]P values: 0.0002 for ELO + PMO + DEX vs. POM + DEX Conclusion Treatment of scid mice bearing OPM2 xenografts with elotuzumab at 0.5 mg/kg or pomalidomide at 5 mg/kg as single agents inhibited tumor growth, however the combination of elotuzumab and pomalidomide treatment inhibited tumor growth better than either of the single agents alone. Treatment with dexamethasone at 5 mg/kg had little or no elotuzumab in presence of pomalidomide and dexamethasone; the relationship between changes in soluble SLAMF7 (sSLAMF7) from baseline and response; the relationship between baseline measurements of sSLAMF7 and PFS; the changes from baseline of SLAMF7 expression on MM cell and NK cells at time of progression; the relationship between baseline levels of SLAMF7 expression on MM cells and NK cells and response to treatment; the relationship between circulating Multiple Myeloma cells (CMMCs) at baseline and while on therapy; the association between cytogenetic risk and response; the relationship between M-protein and Minimal Residual Disease (MRD) status; and the patient-reported outcomes in disease-related symptoms using MDASI-MM and EQ-5D.

Study Design and Duration

This study is a phase 2 multi-center, open-label, randomized study designed to evaluate the clinical benefit of the investigational combination therapy of elotuzumab, pomalidomide, and dexamethasone (E-Pd; the elotuzumab arm) when compared to pomalidomide and dexamethasone (Pd; the control arm) in subjects with relapsed and refractory multiple myeloma (rrMM).

Subjects will be randomized 1:1 to receive either pomalidomide/dexamethasone (Pd) or elotuzumab/pomalidomide/dexamethasone (E-Pd). The randomization will be stratified by: (i) number of lines of prior therapy (2-3 versus ≥4); and (ii) ISS stage at study entry (I-II versus III).

Dosing

The dose selection of 10 mg/kg and 20 mg/kg of elotuzumab for this study is based on data from the phase 1 and 2 studies that have been conducted assessing pharmacokinetics (PK), safety, and preliminary efficacy of elotuzumab. The weekly dosing in the 1st 2 cycles serves as a loading dose in order to reach and exceed the target levels predicted based on preclinical models.

Simulations based on the PK analysis suggest the trough serum concentrations of elotuzumab in most (>90%) subjects treated with 10 and 20 mg/kg doses are above the target levels predicted based on preclinical models. Similarly, model based simulations suggested that the mean trough concentrations were maintained above the target levels from preclinical models with 20 mg/kg monthly elotuzumab dosing. Following elotuzumab dosing of 10 and 20 mg/kg in combination with lenalidomide, the observed steady-state Cmin values consistently remained above 70 μg/mL, the minimum efficacious trough concentrations (Lonial et. al., J Clin Oncol. 30(16):1953-1959. (2012)). Elotuzumab dosing also resulted in complete saturation of SLAMF7 on bone marrow plasma cells at doses ≥10 mg/kg (see FIG. 7). Given the lack of difference in efficacy, safety, PK and SLAMF7 saturation between 10 and 20 mg/kg, the 10 mg/kg weekly for the first 2 cycles followed by 20 mg/kg monthly thereafter, was selected to improve patient convenience and compliance.

A schema for this study is provided in FIG. 6. Briefly, an overview of the arms, doses, mode of administration, and duration of treatment is as follows:

Control Arm
Pomalidomide: 4 mg PO QD Days 1-21 of each cycle
Dexamethasone:
    Subjects ≤75 years old: 40 mg PO Days (1, 8, 15 and 22) of each cycle
    Subjects >75 years old: 20 mg PO Days (1, 8, 15 and 22) of each cycle
Elotuzumab Arm
Elotuzumab:
    Cycle 1-2: 10 mg/kg IV Days 1, 8, 15 and 22 of each cycle
    Cycle 3 and beyond: 20 mg/kg IV Day 1 of each cycle
Pomalidomide: 4 mg PO QD Days 1-21 of each cycle
Dexamethasone: Days 1, 8, 15 and 22 of each cycle
    Subjects ≤75 years old: weeks with elotuzumab dosing: 28 mg PO+8 mg IV and 40 mg PO on non-elotuzumab dosing weeks
    Subjects >75 years old: weeks with elotuzumab dosing: 8 mg PO+8 mg IV and 20 mg PO on non-elotuzumab dosing weeks A cycle is defined as 28 days. Treatment with study drug continues until disease progression, unacceptable toxicity (adverse event related to study drug), or subject meets other criteria for discontinuation of study drug.

Study Population

Subjects who are diagnosed with relapsed and refractory multiple myeloma defined as: (i) Must have received ≥2 prior lines of therapy (See Appendix 1) which must have included at least 2 consecutive cycles of lenalidomide and a proteosome inhibitor alone or in combination; (ii) Documented refractory or relapsed and refractory (R/R) multiple myeloma; (iii) Refractory (progressed on or within 60 days of treatment) to their last treatment; and (iv) Subjects must have failed treatment with a proteosome inhibitor and lenalidomide in one of the following ways:

a. "Refractory" to proteosome inhibitor and lenalidomide, and to their last treatment.

b. "Relapsed and refractory"=patients had achieved at least a partial response to previous treatment with proteosome inhibitor or lenalidomide, or both, but progressed within 6 months, and were refractory to their last treatment Study Assessments Tumor response assessment by modified IMWG criteria (see Table X below) will be evaluated during the trial for all randomized subjects. The primary endpoint of PFS will be based on the investigator's assessment.

TABLE 4

DEFINITIONS OF RESPONSE AND PROGRESSION CRITERIA (MODIFIED FROM IMWG)

| Response Subcategory | Response Criteria[a] |
| --- | --- |
| Stringent Complete Response (sCR) | CR, as defined below, plus the following: Normal FLC ratio[b] and absence of clonal cells[c] in bone marrow by immunohistochemistry or immunofluorescence. |
| Complete Response (CR)[b] | Negative immunofixation of serum and urine and disappearance of any soft tissue plasmacytomas, and <5% plasma cells in bone marrow. |
| Very Good Partial Response (VGPR)[b] | Serum and urine M-protein detectable by immunofixation but not on electrophoresis or ≥90% reduction in serum M-protein level plus urine M-protein level <100 mg per 24 hour. |
| Partial Response (PR) | ≥50% reduction of serum M-protein and reduction in 24-hour urinary M-protein by ≥90% or to <200 mg per 24 hour. If serum and urine M-protein are unmeasurable, a ≥50% decrease in the difference between involved and uninvolved FLC levels is required in place of the M-protein criteria. In addition to the above criteria, if present at baseline, ≥50% reduction in the size of soft tissue plasmacytomas is also required |

TABLE 4-continued

DEFINITIONS OF RESPONSE AND PROGRESSION CRITERIA (MODIFIED FROM IMWG)

| Response Subcategory | Response Criteria[a] |
|---|---|
| Minor (Minimal) Response (MR) | 25-49% reduction of serum M-protein and reduction in 24-hour urine M-protein by 50-89%, which still exceeds 200 mg per 24 hours. In addition, if present at baseline, 25-49% reduction in the size of soft tissue plasmacytomas is also required. No increase in the size or number of lytic bone lesions (development of compression fracture does not exclude response). |
| Stable Disease (SD) | Not meeting criteria for CR, VGPR, PR, MR, or progression. |
| Progressive disease | Any of the following: Increase of 25% from lowest response value in any one or more of the following: 1. Serum M-component (absolute increase must be ≥0.5 g/dL)[d] and/or 2. Urine M-component (absolute increase must be ≥200 mg per 24 h) and/or 3. Only in patients without measurable serum and urine M-protein levels: the difference between involved and uninvolved FLC levels (absolute increase must be >10 mg/dL) 4. Bone marrow plasma cell percentage (absolute % must be ≥10%) Definite development of new bone lesions or soft tissue plasmacytomas or definite increase in the size of existing bone lesions or soft tissue plasmacytomas Development of hypercalcemia (corrected serum calcium >11.5 mg/100 mL) that can be attributed solely to the plasma cell proliferative disorder |

[a]All response categories require 2 consecutive assessments made at any time before the institution of any new therapy; all categories also require no known evidence of progressive or new bone lesions if radiographic studies were performed. Radiographic studies are not required to satisfy these response requirements. Bone marrow assessments need not be confirmed.
[b]Note clarification to IMWG criteria for coding CR and VGPR in patients in whom the only measurable disease is by serum FLC levels: CR in such patients is defined as a normal FLC ratio of 0.26-1.65 in addition to CR criteria listed above. VGPR in such patients is defined as a >90% decrease in the difference between involved and uninvolved FLC levels.
[c]Presence or absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]For progressive disease, serum M-component increase of ≥1 g/dL is sufficient to define progression if starting M-component is ≥5 g/dL Statistical Considerations Sample Size. The primary objective of the study is to compare the progression-free survival between the treatment arms in all randomized subjects. The number of events and power of this study were calculated assuming an exponential distribution for PFS in each arm.

The study will require at least 71 PFS events (progressions or deaths) for a two-sided experiment-wise $\alpha=0.2$ stratified log-rank test, to show a statistically significant difference in PFS between the treatment arms with 85% power when the true hazard ratio of the experimental arm to the control arm is 0.57. This is equivalent to demonstrating an improvement in median PFS from 4.0 months in the Pd arm to a median PFS of 7.0 months in the E-Pd arm. A total of 105 subjects are to be randomized.

Assuming approximately 10% of subjects may be lost to follow-up for the primary endpoint data, an additional 9 subjects will be randomized in the study. It is estimated that it would take approximately 9 months for full accrual of 114 subjects (assuming a fixed accrual rate of 13 subjects per month).

Objective response rate (ORR) is a secondary endpoint for this study. Analysis of response rate will be conducted on all randomized subjects. With a sample size of 114 subjects, there will be at least 90% power to detect a 23% improvement in response rate (to 58%), using a two-sided 0.2 level test, in the E-Pd arm compared with a response rate of 35% in the Pd arm.

Overall Survival (OS) is a secondary objective for this study. The analysis of OS will be conducted on all randomized subjects. The final analysis of OS will be conducted after 78 deaths have been observed from 114 subjects. This is expected to occur 18 months (1.5 years) from the time of the final PFS analysis. With 78 events the study will have 75% power using a two-sided stratified log-rank test at an $\alpha=0.2$ level, to show a statistically significant difference when the true hazard ratio is 0.64. This is equivalent to demonstrating a 56% improvement in median OS, i.e., 19.8 months in the E-Pd arm compared to the median OS in the Pd arm of 12.7 months.

East version 5.4 was used for sample size/power computation.

Elotuzumab Intravenous Infusion

Elotuzumab can cause infusion reactions. Infusion reactions were reported in approximately 10% of patients treated with elotuzumab, lenalidomide and dexamethasone in Study CA204004 and in 7% of patients treated with elotuzumab, bortezomib and dexamethasone in Study CA204009. All reports of infusion reaction were ≤Grade 3. Grade 3 infusion reactions occurred in 1% of patients in Study CA204004 and in no patients in Study CA204009. The most common symptoms of an infusion reaction included fever, chills and hypertension. In Study CA204004, 5% of patients required interruption of the administration of elotuzumab due to infusion reaction for a median of 25 minutes and 1% of patients discontinued due to infusion reactions. In Study CA204009, 20% of patients required interruption of the administration of elotuzumab for a median of 40 minutes and none discontinued due to infusion reactions. Of the patients who experienced an infusion reaction, 70% (23/33) in Study CA204004 and 80% (4/5) in Study CA204009 had them during the first dose.

Premedication consisting of dexamethasone, H1 blocker, H2 blocker, and acetaminophen should be administered prior to elotuzumab infusion.

Elotuzumab Infusion Rate

The maximum infusion rate of 2 ml/min was initially explored in the phase 1 and 2 elotuzumab clinical trials. However, the phase 2 portion of the CA204003 (1703) and the CA204009 studies allowed an infusion rate escalation in subjects without infusion reactions for a minimum of 4 cycles of study therapy at 2 ml/min. The infusion rates are allowed to increase by 1 ml/min per cycle, up to 5 ml/min.

Preliminary safety data of the 5 ml/minute infusion rate are based on an analysis of subjects who escalated the elotuzumab infusion to 5 ml/minute in the CA204003 (1703) and CA204009 studies. In the phase 2 portion of the CA204003 (1703) study, 33% of all study infusions and 42.5% of subjects received infusions at 5 ml/min. In subjects who were administered infusions ≤2 ml/min, there were 7 grade 1-2 infusion reactions, and 1 grade 3-4 infusion reaction. In those subjects who received elotuzumab infusions at rates >2 ml/min, there was 1 grade 1-2 infusion reactions (nausea) and no grade 3-4 infusion reactions. In the randomized phase 2 CA204009 study, 27% of all subjects and 9% of all infusions on the investigational arm received infusions at 5 ml/min. For subjects reaching infusion rates >2 ml/min, there were no infusion reactions of any grade.

Preliminary data are available for an ongoing study CA204112 with elotuzumab administration in <1 hour (5 ml/min) combined with lenalidomide/dexamethasone in newly diagnosed and relapsed/refractory myeloma. In this trial, the infusion rate was escalated to 5 ml/min by the third elotuzumab dose. Using this escalation strategy, 67 of 69 subjects treated reached the maximum infusion rate of 5 ml/min, which accounted for >80% of infusions (621 out of 764 infusions), with no increased frequency of infusion reactions.

A similar infusion rate escalation paradigm will be adopted for subjects who have not experienced ≥grade 2 infusion reactions with prior elotuzumab infusions. The maximum infusion rate will be 5 ml/min.

Rationale for Pomalidomide

Previous clinical trials have demonstrated the safety of combining elotuzumab with two other immunomodulatory drugs (IMiDs) similar to pomalidomide. Phase 1, 2 and 3 trials demonstrated that elotuzumab safely combines with thalidomide and lenalidomide. Adverse reactions in these studies were similar to results of historical trials of either thalidomide or lenalidomide alone with the exception of infusion reactions caused by elotuzumab, which are mitigated with a premedication regimen. Since lenalidomide and pomalidomide are in the same class of drugs, and have a similar safety and pharmacokinetic profile, elotuzumab is expected to elicit a similar safety profile as did the lenalidomide—elotuzumab combinations. Pomalidomide is a standard of care agent approved for the population selected for this clinical trial.

Pomalidomide, in combination with dexamethasone, was evaluated in a Phase 1/2 study (Richardson et al., *Blood,* 121(11):1961-1967 (2013)).

Thirty-eight subjects with relapsed and refractory MM were enrolled into the Phase 1 portion, which evaluated four dose levels of pomalidomide (2, 3, 4, 5 mg) given daily on Days 1-21 of each 28-day cycle with an option to add dexamethasone 40 mg/week after 4 cycles for lack of response or disease progression. The median age was 67 years with subjects having a median of 6 prior MM regimens which included lenalidomide and bortezomib. There were 4 DLTs (Grade 4 neutropenia) at 5 mg, so the MTD and Phase 2 dose was 4 mg/day. The most common treatment-emergent Grade 3/4 AEs were neutropenia (53%), anemia (21%), thrombocytopenia (18%), and fatigue (16%). Among the 38 subjects enrolled (including 22 subjects who had dexamethasone added), 42% achieved ≥MR or better, 21% achieved ≥PR, and 3% achieved CR. While this study suggested that higher response rates occurred in subjects receiving the higher pomalidomide dose (Richardson et al., *Blood,* 123(12):1826-1832 (2014)), another study demonstrated comparable response rates, durable responses, and overall toxicity between pomalidomide at doses of 2 or 4 mg per day (for 28/28 days) along with 40 mg weekly dexamethasone in patients who had failed both lenalidomide and bortezomib (Lacy et al., *Blood,* 118(11):2970-2975 (2011)). A recent follow-up showed that subjects treated with pomalidomide at 2 mg/day versus 4 mg/day achieved an ORR (≥PR) of 29% versus 35% in the 4 mg/day subjects and a median duration of response of 14.1 versus 14.5 months, and a median PFS of 5.5 versus 6.9 months, respectively (Lacy et al., ASH Abstract 4780 (2014)).

The effect of pomalidomide is seen in patients with renal insufficiency. In the STRATUS single arm, open-label Phase 3b trial of pomalidomide and low-dose DEX in relapsed/refractory MM patients with renal insufficiency (creatinine clearance<60 mL/min) or without renal insufficiency (creatinine clearance>60 mL/min), there was comparable ORR (33% for both groups), median PFS (3.7 versus 4.7 months), duration of response (6.7 versus 8.4 months), and tolerability between both groups (Weisel et al., Abstract, European Hematology Association, P286 (June 2015)). Analysis of Patients with Refractory or Relapsed and Refractory Multiple Myeloma and Renal Impairment Treated with Pomalidomide+Low-Dose Dexamethasone in the Phase 3b STRATUS Trial (MM-010) ((Weisel et al., Abstract, European Hematology Association, P286 (June 2015)).

The U.S. FDA granted accelerated approval for pomalidomide on the basis of the Phase 2 study (MM-002), which randomized subjects with relapsed and refractory disease after at least 2 prior regimens, including lenalidomide and bortezomib and who had progressed within 60 days of their last therapy, to receive either pomalidomide alone (4 mg/day on days 1-21 of a 28-day cycle; n=108) or in combination with 40 mg/week dexamethasone (n=113) (Richardson et al., *Blood,* 123(12):1826-1832 (2014)). Subjects in both arms were comparably refractory to lenalidomide (~79%), bortezomib (~71%) or both (~62%), and 95% had >2 prior therapy regimens. With a median follow-up of 14.2 months, the median PFS was 4.2 and 2.7 months (HR=0.68, P=0.003), ORR (≥PR) was 33% versus 18% (P=0.013), median response duration was 8.3 versus 10.7 months, and median OS was 16.5 versus 13.6 months, respectively for the pomalidomide+dexamethasone arm compared to the pomalidomide alone arm. The most common hematologic Grade 3/4 AEs were neutropenia (41% versus 48%), anemia (22% versus 24%), and thrombocytopenia (19% versus 22%). The most common nonhematologic AE was pneumonia (22% versus 15%) and fatigue (14% versus 11%) in the pomalidomide+dexamethasone arm compared to the pomalidomide alone arm, respectively. The frequency of febrile neutropenia was low (3% versus 5%), as was the incidence of DVT (2% versus 3%). There were no grade 3 or 4 events of peripheral neuropathy reported.

The EMA granted approval for pomalidomide in Europe based on the phase 3 study (MM-003/NIMBUS trial) which evaluated the combination of pomalidomide with low-dose dexamethasone versus high-dose dexamethasone in refractory or relapsed and refractory MM subjects. A total of 455 patients were randomly assigned in a 2:1 ratio to receive pomalidomide plus low-dose dexamethasone (N=302) or high-dose dexamethasone (N=153).

Pomalidomide was dosed at 4 mg orally on Days 1-21 of each 28-day cycle and dexamethasone was given at a low dose of 40 mg/day on days 1, 8, 15, and 22 or at a high dose of 40 mg/day on days 1-4, 9-12, and 17-20. Treatment continued until disease progression or unacceptable toxicity. The primary endpoint of the study was progression-free survival (PFS). The median PFS with pomalidomide plus low-dose dexamethasone was 4.0 months (95% CI 3.6-4.7) versus 1.9 months (1.9-2.2) with high-dose dexamethasone (HR 0.48 [95% CI 0.39-0.60]; p<0.0001). The median OS was also significantly longer (12.7 months [95% CI 10.4-15.5] versus 8.1 months [6.9-10.8]; HR 0.74 [0.56-0.97]; p=0.0285). The objective response rate after a median follow-up of 10.0 months was 31% in the pomalidomide plus low-dose dexamethasone group versus 10% in the high-dose dexamethasone group (odds ratio [OR] 4.22 [2.35-7.58]; p<0.0001).

In the pomalidomide plus low-dose dexamethasone and high-dose dexamethasone arms, respectively, the most common grade 3-4 hematological adverse events were neutropenia (48% versus 16%), anemia (33% versus 37%), and thrombocytopenia (22% versus 26%). The most common grade 3-4 non-hematological adverse events were pneumonia (13% versus 8%), bone pain (7% versus 5%), and fatigue (5% versus 6%).

The planned dose of pomalidomide in this study will be 4 mg orally on Days 1-21 of each 28-day cycle in combination with low dose dexamethasone (40 mg/day on days 1, 8, 15, and 22, orally) which is the approved dose and schedule for treatment in this population.

Endpoints
Primary Endpoint

PFS will be defined as the time, in months, from randomization to the date of the first documented tumor progression or death due to any cause. Clinical deterioration will not be considered progression. A subject who neither progresses nor dies will be censored on the date of their last tumor assessment. A subject who does not have any post-baseline tumor assessments and who has not died will be censored on the date at which they were randomized.

Secondary Endpoint

Secondary endpoints will include (i) Objective response rate is defined as the proportion of randomized subjects who achieve a best response of partial response (PR) or better using the criteria in Table 4 as per investigator's assessment; and (ii) Overall survival is defined as the time from randomization to the date of death from any cause. If a subject has not died, their survival time will be censored at the date of last contact ("last known alive date"). A subject will be censored at the date of randomization if they were randomized but had no follow-up.

Statistical Analysis
Interim Analysis

Efficacy data including response rate and PFS will be reviewed at the time of the interim analysis.

Final Analysis

The primary objective of this study is to compare PFS between the two randomized arms. A two-sided $\alpha=0.2$ log-rank test, stratified by the number of lines of prior therapy (2-3 versus $\geq 4$) and ISS stage at study entry (I-II versus III) will be used to compare the PFS of subjects randomized to receive E-Pd to that of subjects randomized to Pd. A stratified Cox proportional hazard model for PFS with treatment arm as single covariate will be used to report HR and the corresponding 80% confidence interval (CI). Median PFS will be estimated via the Kaplan-Meier product limit method. Two-sided 80% CI for the median PFS will be computed for each randomized arm by the Brookmeyer and Crowley method. Two-sided 95% CI for the median PFS will also be computed. Kaplan-Meier plots of PFS will be presented.

Objective response rate is a secondary endpoint. A two-sided $\alpha=0.2$ level Cochran-Mantel-Haenszel (CMH) test, stratified using the same factors as in PFS, will be used to compare the response rate between the treatment arms. The response rate, along with its exact two-sided 80% CI, will be computed within each treatment arm. A two-sided, 95% CI for difference of response rate between the treatment arms will also be computed.

OS is a secondary endpoint. OS will be compared between the treatment arms among all randomized subjects using a two-sided, $\alpha=0.2$ level stratified log-rank test (using the same factors as in PFS). Similar analysis as in PFS will be conducted for OS.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method for treating a patient with multiple myeloma comprising administering a combination therapeutic regiment comprising: (i) a therapeutically effective amount of pomalidomide at a dosage of about 4 mg; (ii) a therapeutically effective amount of elotuzumab at a dosage of about 10 mg/kg, and (iii) a therapeutically acceptable amount of dexamethasone either orally at a dose of about 28 mg to 40 mg or via IV at a dose of about 8 mg, wherein said patient has progressed after receiving an initial treatment, and wherein said combination results in regression of said multiple myeloma.

2. The method of claim 1, wherein pomalidomide is administered at a dosage of about 4 mg daily for 21 days, elotuzumab is administered at a dosage of about 10 mg/kg, and dexamethasone is administered either orally at a dose of about 28 mg to 40 mg daily for 21 days, or via IV at a dose of about 8 mg weekly.

3. A method for treating a patient with multiple myeloma comprising administering a combination therapeutic regiment wherein:

pomalidomide is administered at a dosage of 4 mg orally on days 1-21 of each cycle;

elotuzumab is administered at a dosage of 10 mg/kg intravenously (IV) on days 1, 8, 15 and 22 of cycles 1 and 2, and then administered at a dosage of 20 mg/kg IV on day 1 of cycles 3 and beyond; and dexamethasone is administered at a dose of 28 mg orally and 8 mg IV on days of elotuzumab dosing (days 1, 8, 15 and 22 of cycles 1 and 2 and day 1 of cycles 3 and beyond), and at a dose of 40 mg orally per week on weeks without elotuzumab dosing in subjects ≤75 years old, and administered at a dose of 8 mg orally and 8 mg IV on days of elotuzumab dosing (days 1, 8, 15 and 22 of cycles 1 and 2 and day 1 of cycles 3 and beyond), and at a dose of 20 mg orally per week on weeks without elotuzumab dosing in subjects >75 years old, wherein a cycle is defined as 28 days, wherein said patient has progressed after receiving an initial treatment, and wherein said combination results in regression of said multiple myeloma.

* * * * *